US 6,489,112 B1

(12) United States Patent
Hadd et al.

(10) Patent No.: US 6,489,112 B1
(45) Date of Patent: Dec. 3, 2002

(54) METHODS AND APPARATUS FOR TEMPLATE CAPTURE AND NORMALIZATION FOR SUBMICROLITER REACTION

(75) Inventors: Andy Hadd, San Jose, CA (US); Stevan Jovanovich, Livermore, CA (US)

(73) Assignee: Molecular Dynamics, Inc., Sunnyvale, CA (US)

(*) Notice: Subject to any disclaimer, the term of this patent is extended or adjusted under 35 U.S.C. 154(b) by 5 days.

(21) Appl. No.: 09/632,094

(22) Filed: Aug. 2, 2000

Related U.S. Application Data

(63) Continuation-in-part of application No. 09/577,199, filed on May 23, 2000, now Pat. No. 6,423,536.
(60) Provisional application No. 60/146,732, filed on Aug. 2, 1999.

(51) Int. Cl.[7] ............................ C12Q 1/68; C12P 19/34; C12M 1/34; C07H 21/02; C07H 21/04
(52) U.S. Cl. .................. 435/6; 435/91.1; 435/91.2; 435/287.1; 435/287.2; 536/23.1; 536/24.3; 536/24.33
(58) Field of Search .................. 435/6, 91.1, 91.2, 435/183, 287.1, 287.2; 422/68.1; 436/94; 536/23.1, 24.3, 24.33, 25.3

(56) References Cited

U.S. PATENT DOCUMENTS

| | | | | |
|---|---|---|---|---|
| 5,234,809 A | * | 8/1993 | Boom et al. ................... 435/91 |
| 5,455,175 A | | 10/1995 | Wittwer et al. ............. 435/286.1 |
| 5,498,392 A | * | 3/1996 | Wilding et al. ............. 422/68.1 |
| 5,560,811 A | | 10/1996 | Briggs et al. ................. 204/451 |
| 5,720,923 A | | 2/1998 | Haff et al. .................... 422/68.1 |
| 5,785,926 A | | 7/1998 | Seubert et al. ............... 422/100 |
| 5,840,573 A | | 11/1998 | Fields ....................... 435/287.2 |
| 5,846,727 A | * | 12/1998 | Soper et al. ................... 435/6 |
| 5,897,842 A | | 4/1999 | Dunn et al. .................. 422/131 |
| 5,927,547 A | | 7/1999 | Papen et al. ................... 222/57 |
| 6,033,880 A | | 3/2000 | Haff et al. ................... 435/91.1 |
| 6,225,061 B1 | * | 5/2001 | Becker et al. ................... 435/6 |
| 2002/0018998 A1 | * | 2/2002 | Fritz et al. ...................... 435/6 |

FOREIGN PATENT DOCUMENTS

| | | | |
|---|---|---|---|
| DE | 197 46 874 A | 4/1999 | |
| EP | 0 649 853 A | 4/1995 | |
| EP | 0 671 626 A | 9/1995 | |
| EP | WO 97/30062 | * 8/1997 | |
| WO | WO 96/01836 | * 1/1996 | ........... C07H/21/00 |
| WO | WO 97/10331 | 3/1997 | |
| WO | WO 97/40939 | 11/1997 | |

OTHER PUBLICATIONS

Hadd, Andrew G. et al., "Sub–microliter DNA sequencing for capillary array electrophoresis", *Journal of Chromatography A*, vol. 894, No. 1–2, pp. 191–201 (Oct. 2000).

(List continued on next page.)

Primary Examiner—Ethan C. Whibenant
Assistant Examiner—Frank W Lu
(74) Attorney, Agent, or Firm—Fish & Neave; Daniel M. Becker

(57) ABSTRACT

Methods for preparing nanoscale reactions using nucleic acids are presented. Nucleic acids are captured saturably, yet reversibly, on the internal surface of the reaction chamber, typically a capillary. Excess nucleic acid is removed and the reaction is performed directly within the capillary. Alternatively, the saturably bound nucleic acid is eluted, dispensing a metered amount of nucleic acid for subsequent reaction in a separate chamber. Devices for effecting the methods of the invention and a system designed advantageously to utilize the methods for high throughput nucleic acid sequencing reactions are also provided.

20 Claims, 31 Drawing Sheets

OTHER PUBLICATIONS

Swerdlow, H. et al., "Fully automated DNA reaction and analysis in a fluidic capillary instrument", *Analytical Chemistry*, vol. 69, No. 5, pp. 848–855 (Mar. 1997).

Chen et al., "Recovery of DNA Segments from Agarose Gels", *Anal. Biochem. 101*, pp. 339–341, 1980.

Sheikh, Sabina N. et al., "Re–usable DNA template for the polymerase chain reaction (PCR)", *Nucleic Acids Research*, vol. 25(17), pp. 3537–3542, 1997.

Soper, Steven A. et al., "Sanger DNA–Sequencing Reactions performed in a Solid–Phase Nanoreactor Directly Coupled to Capillary Gel electrophoresis", *Analytical Chemistry*, vol. 70(19), pp. 4036–4043, 1998.

"Geneclean—How it works", downloaded from *http://www.bio101.com/newsletter/august98/3.html*, 2 pages.

Vogelstein et al., "Preparative and Analytical Purification of DNA from Agarose", *Proc. Natl. Acad. Sci.,* USA 96, pp. 615–619, 1979.

* cited by examiner

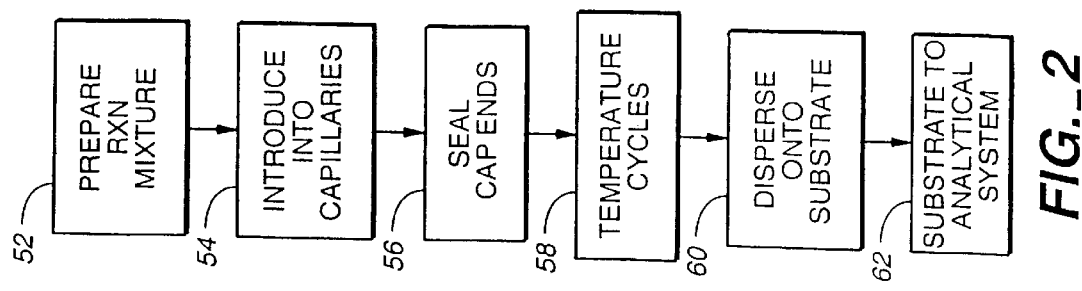
FIG._2
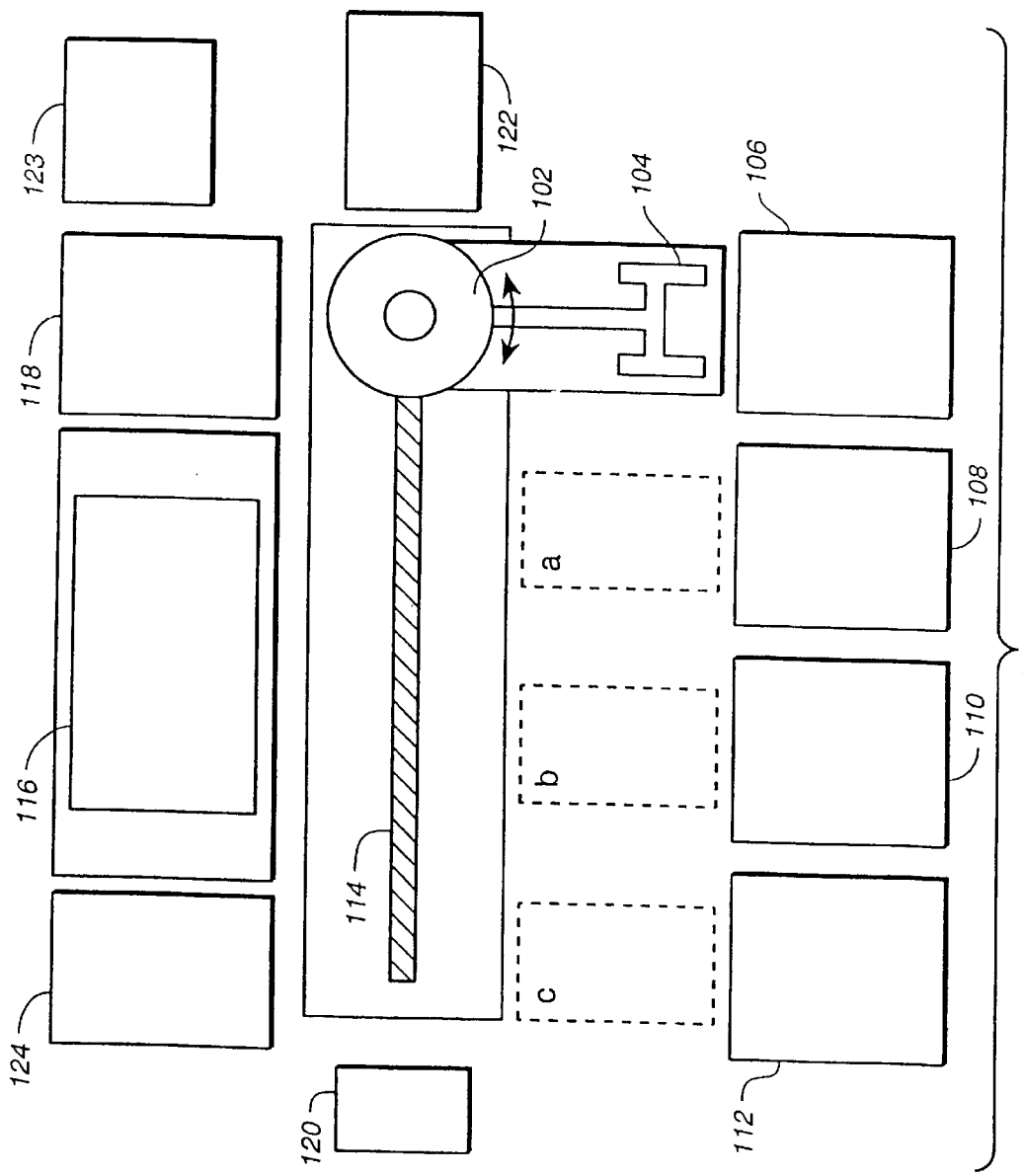
FIG._1

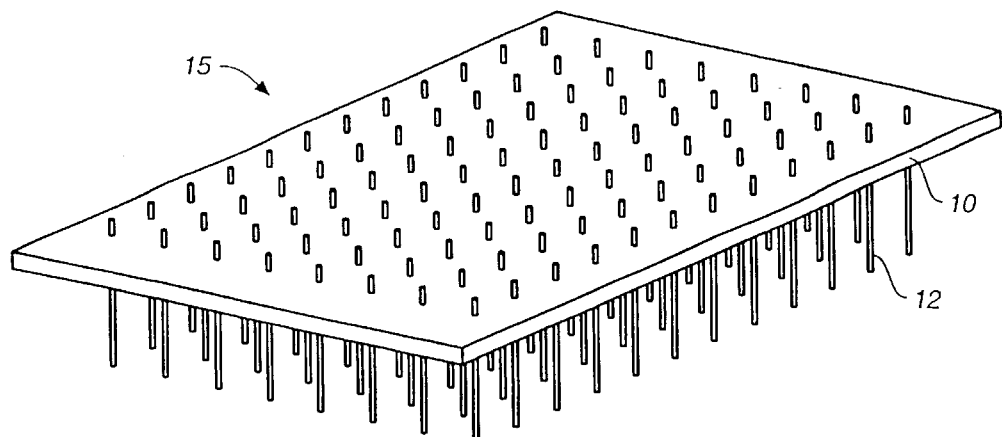
FIG._3A
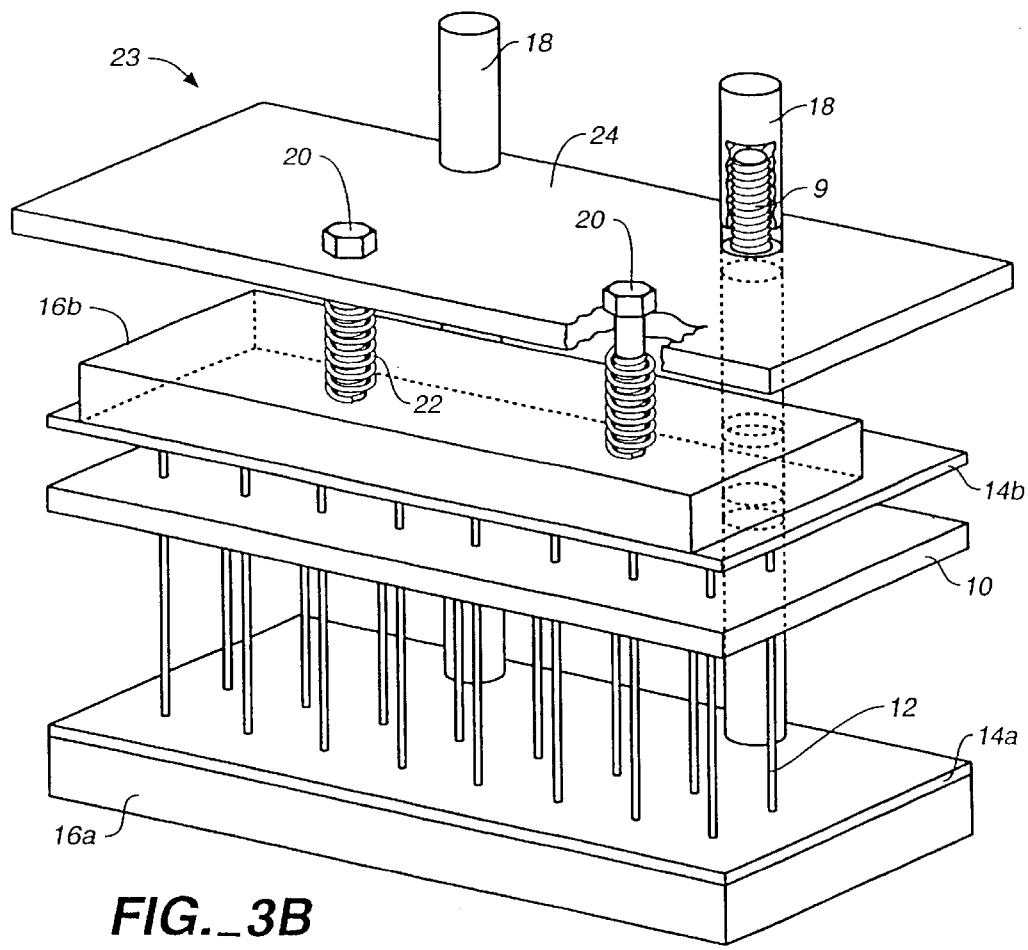
FIG._3B

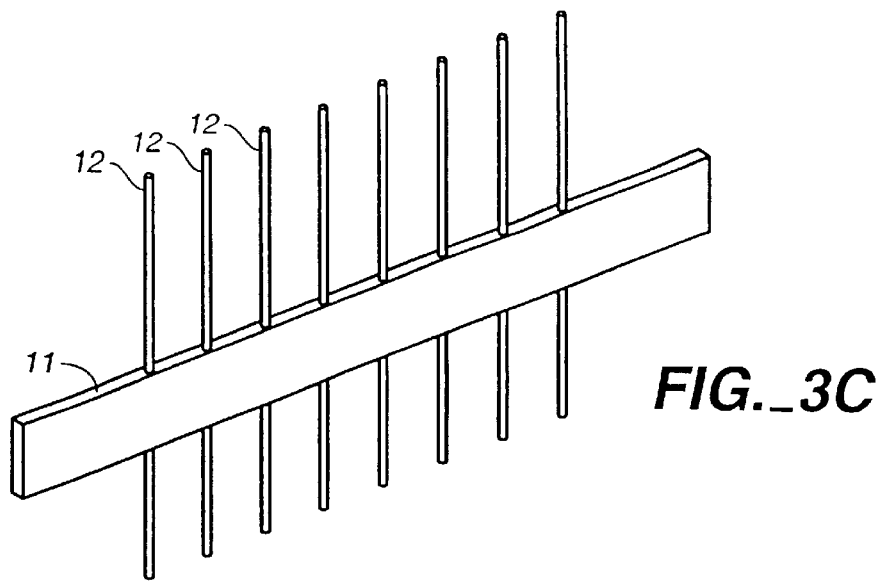
FIG._3C
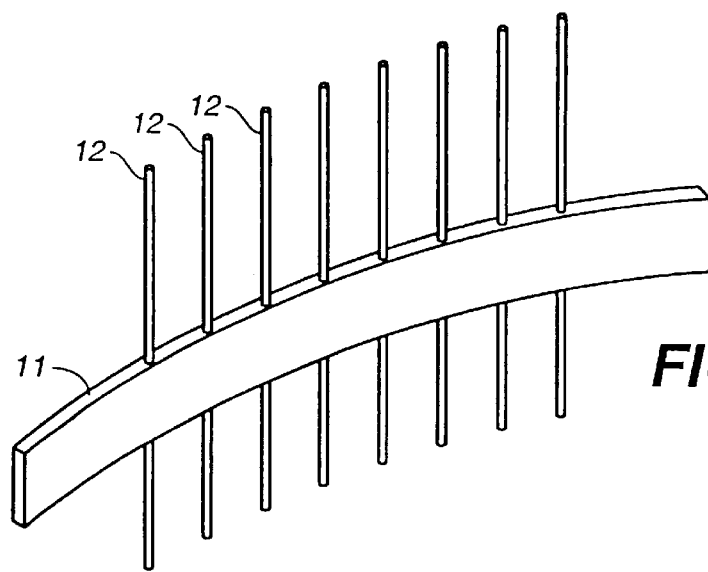
FIG._3D
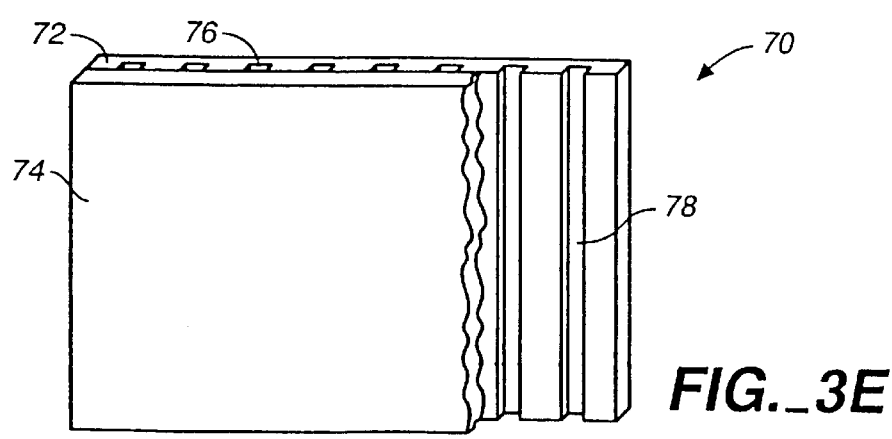
FIG._3E

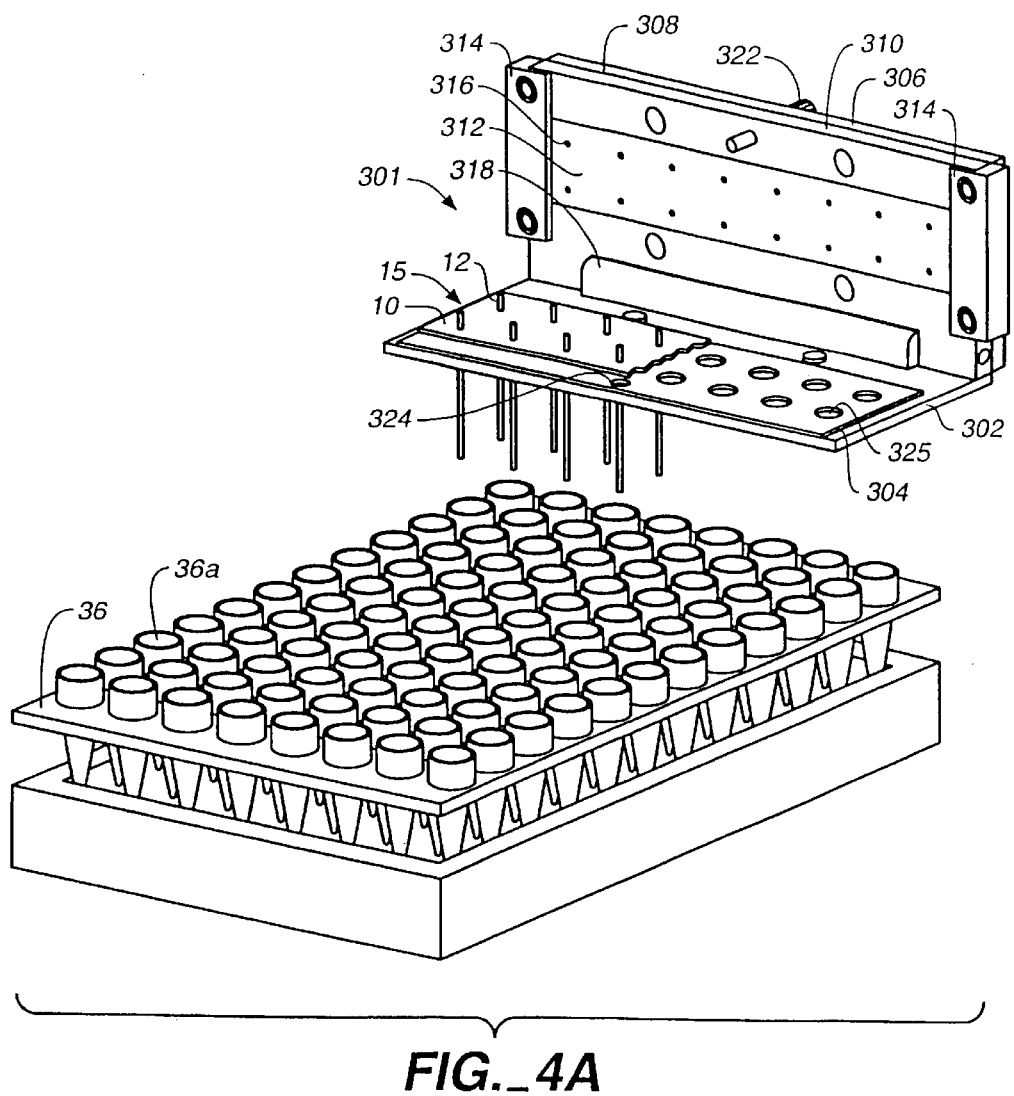
FIG._4A

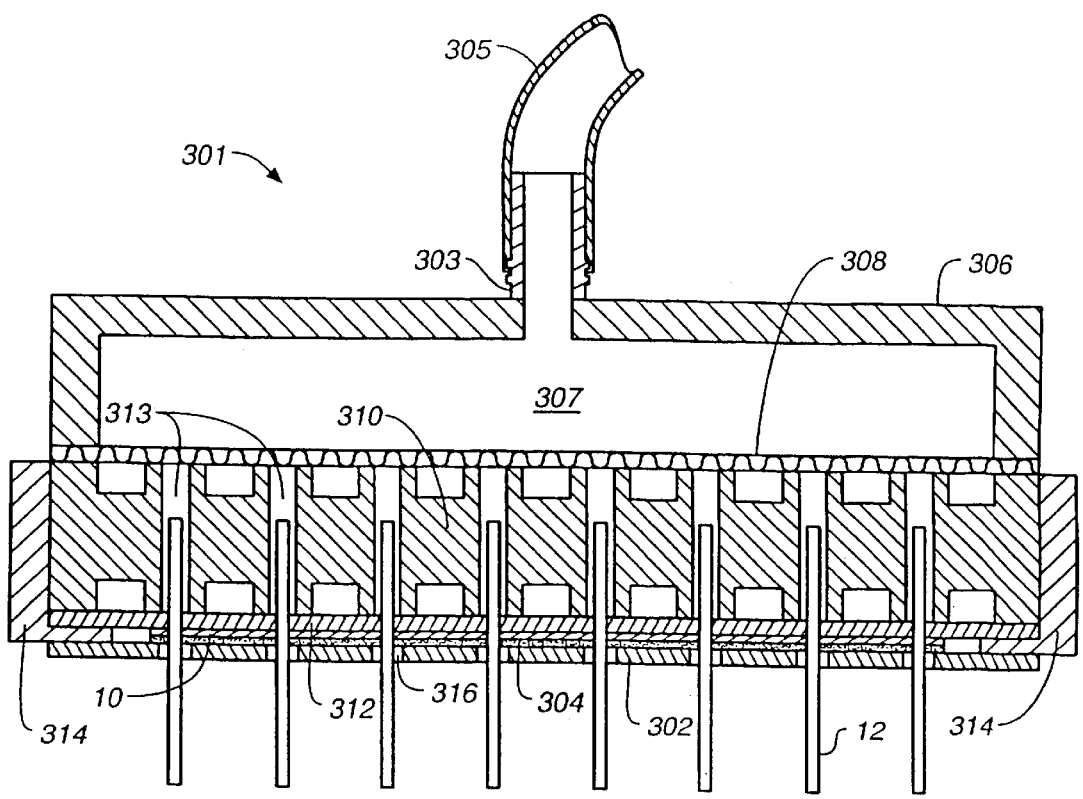
FIG._4B
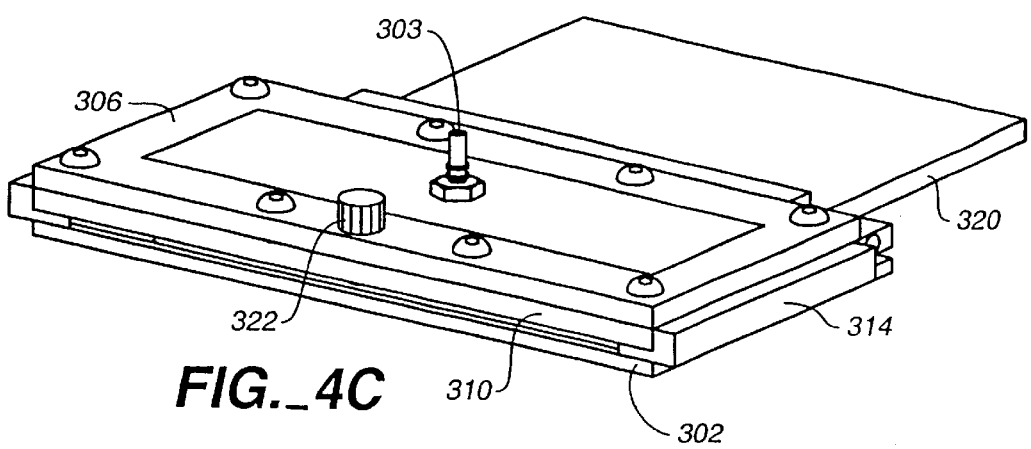
FIG._4C

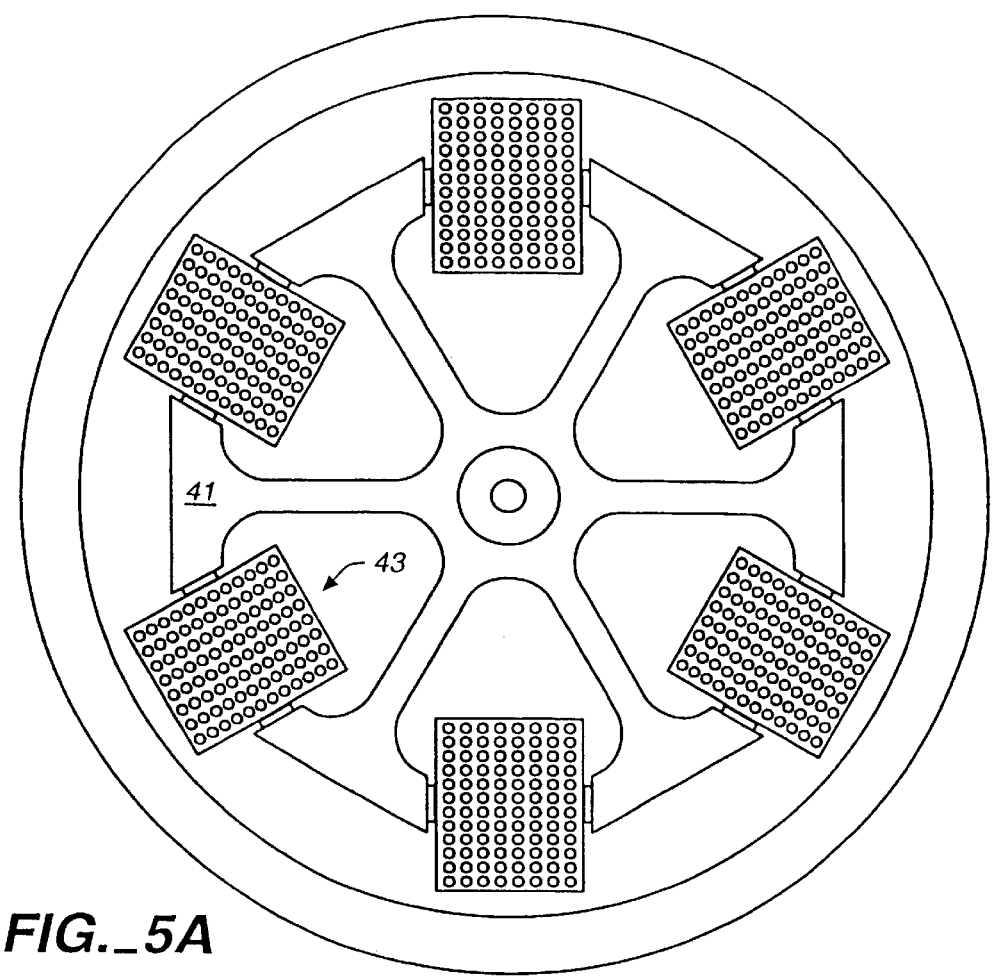
FIG._5A
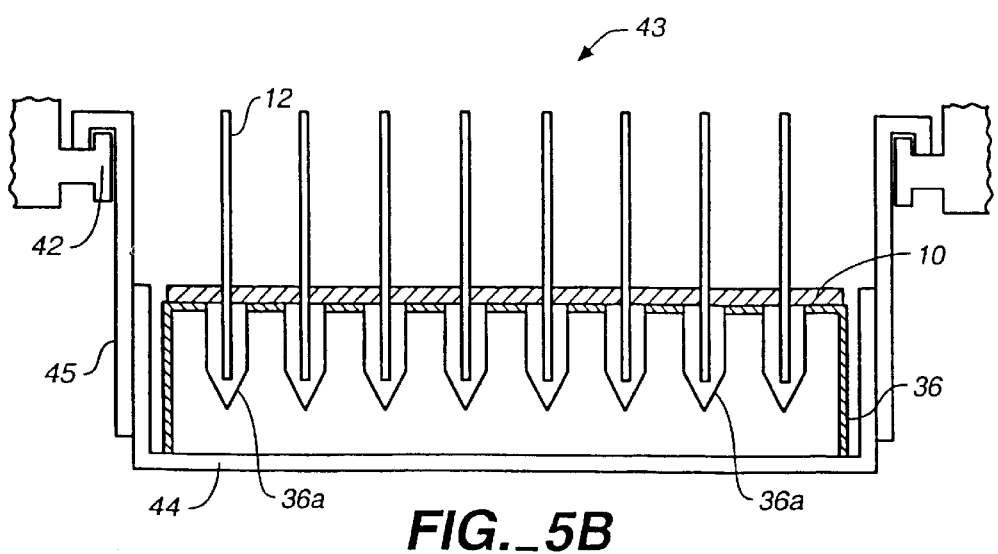
FIG._5B

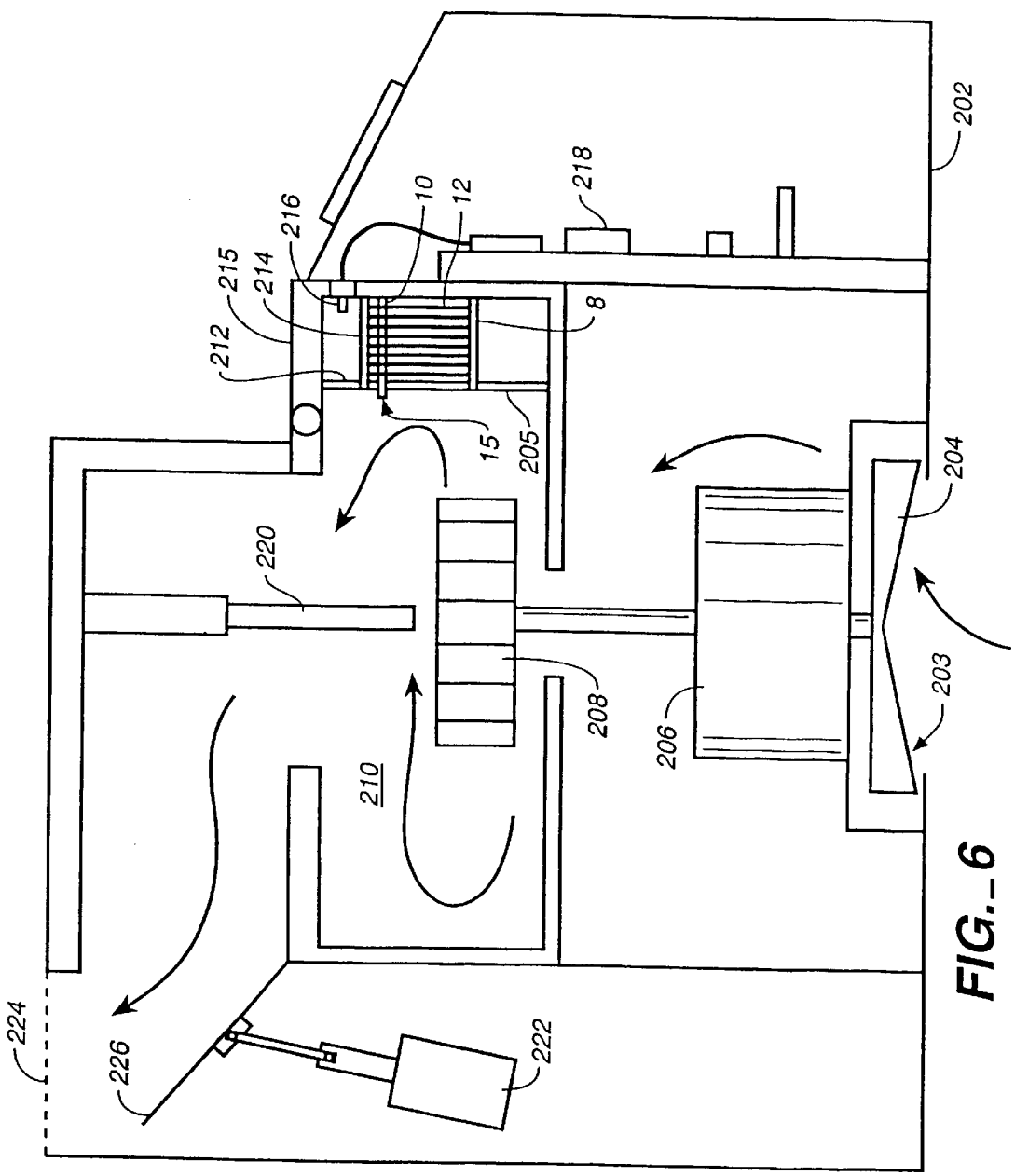
FIG._6

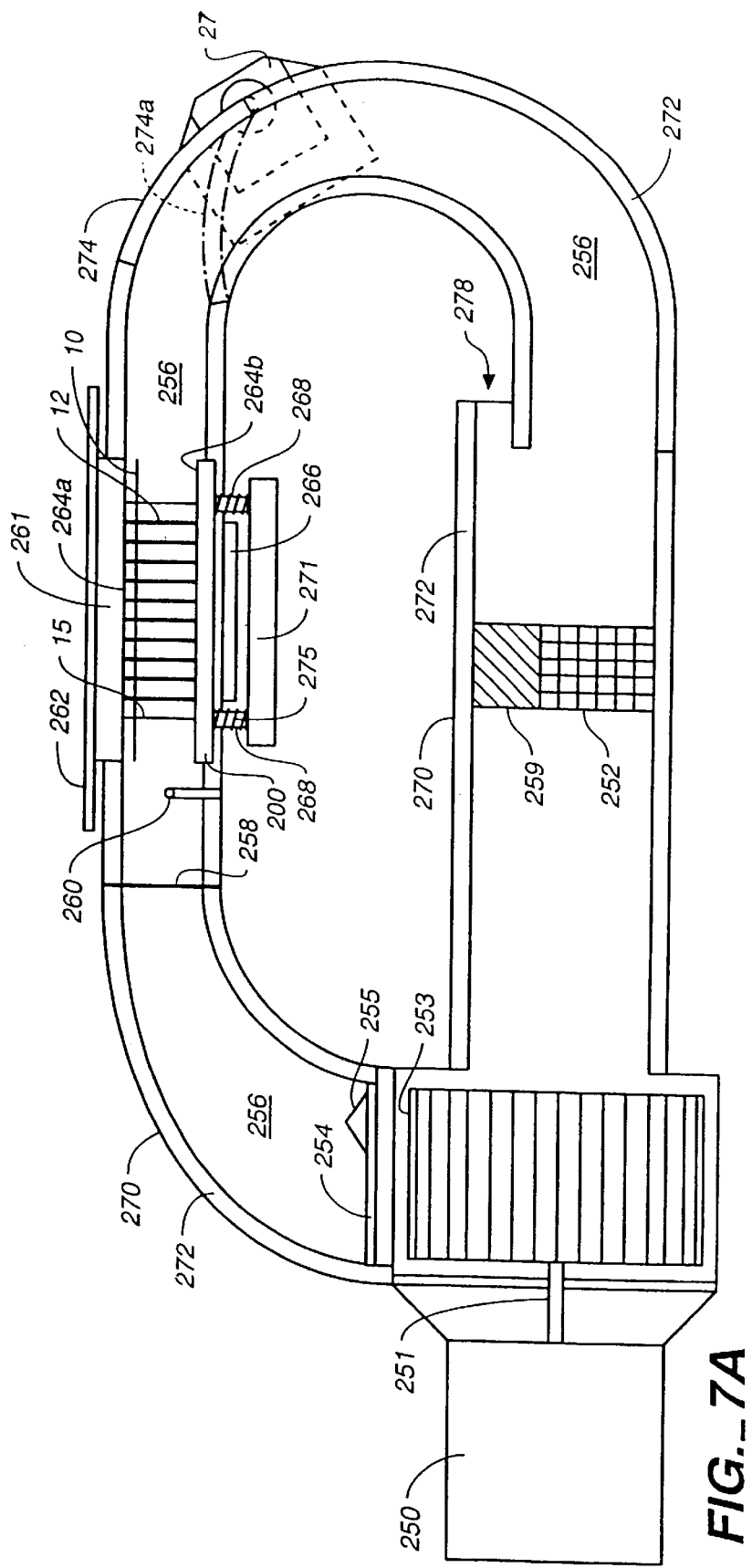
FIG._7A

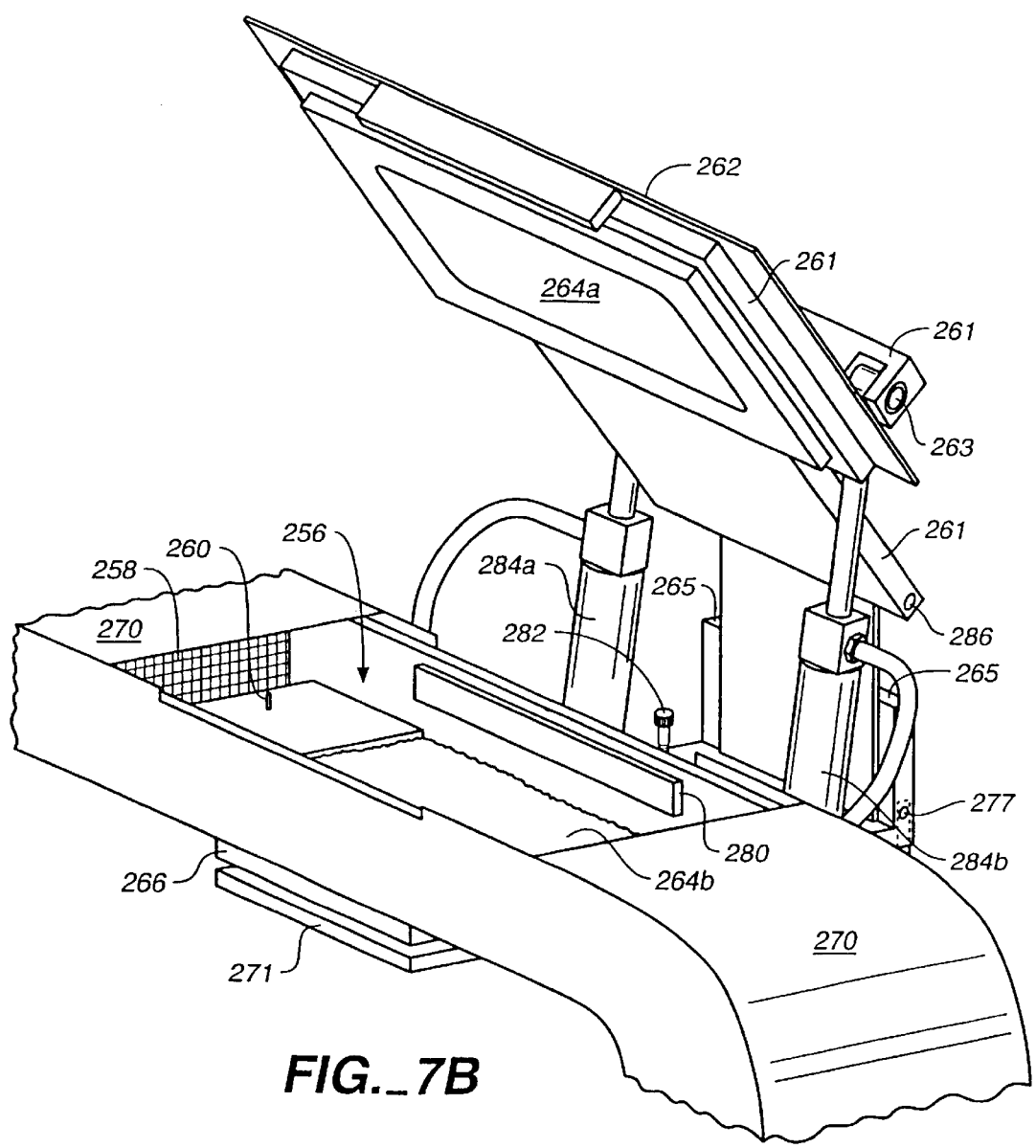
FIG._7B

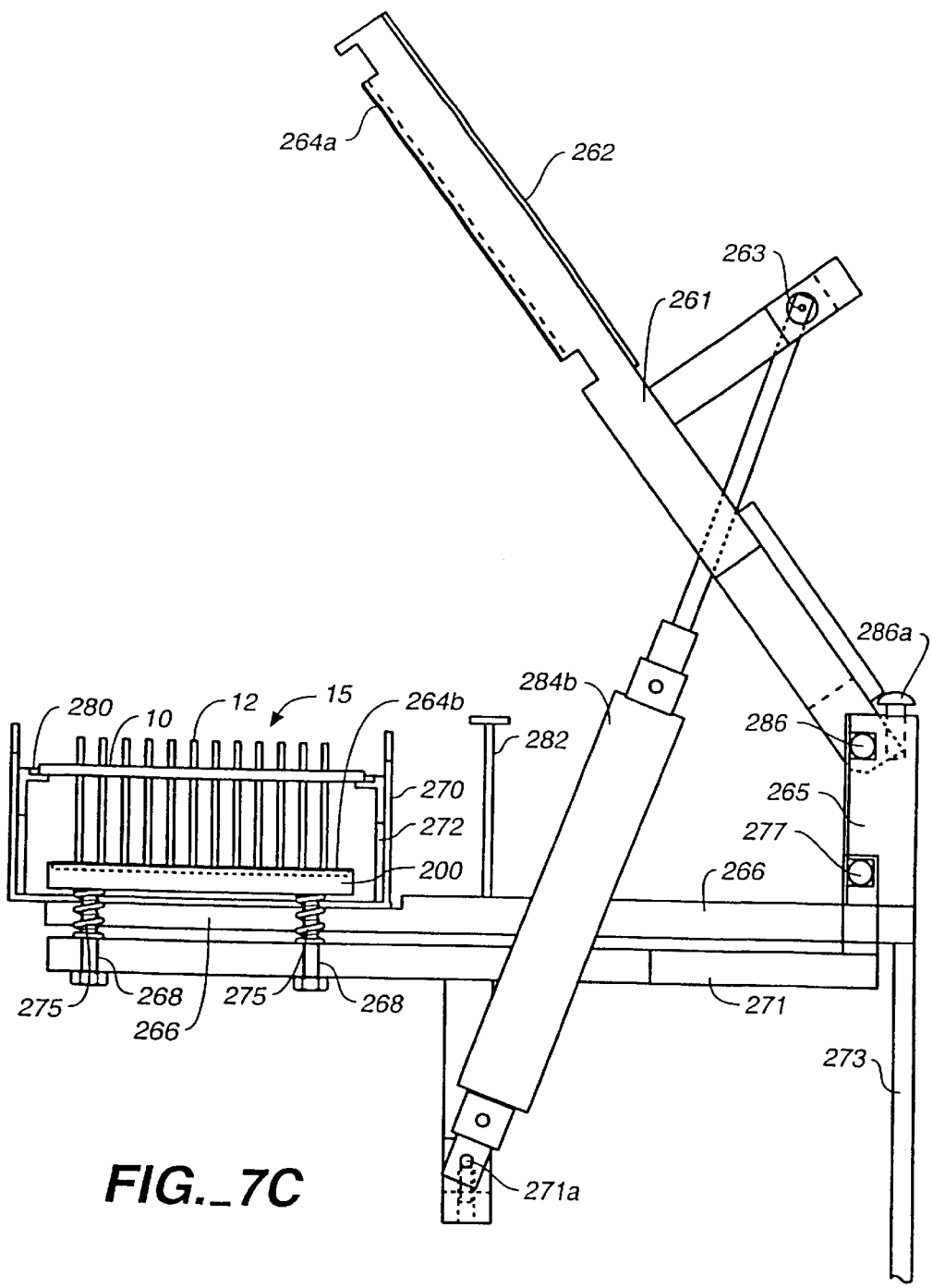
FIG._7C

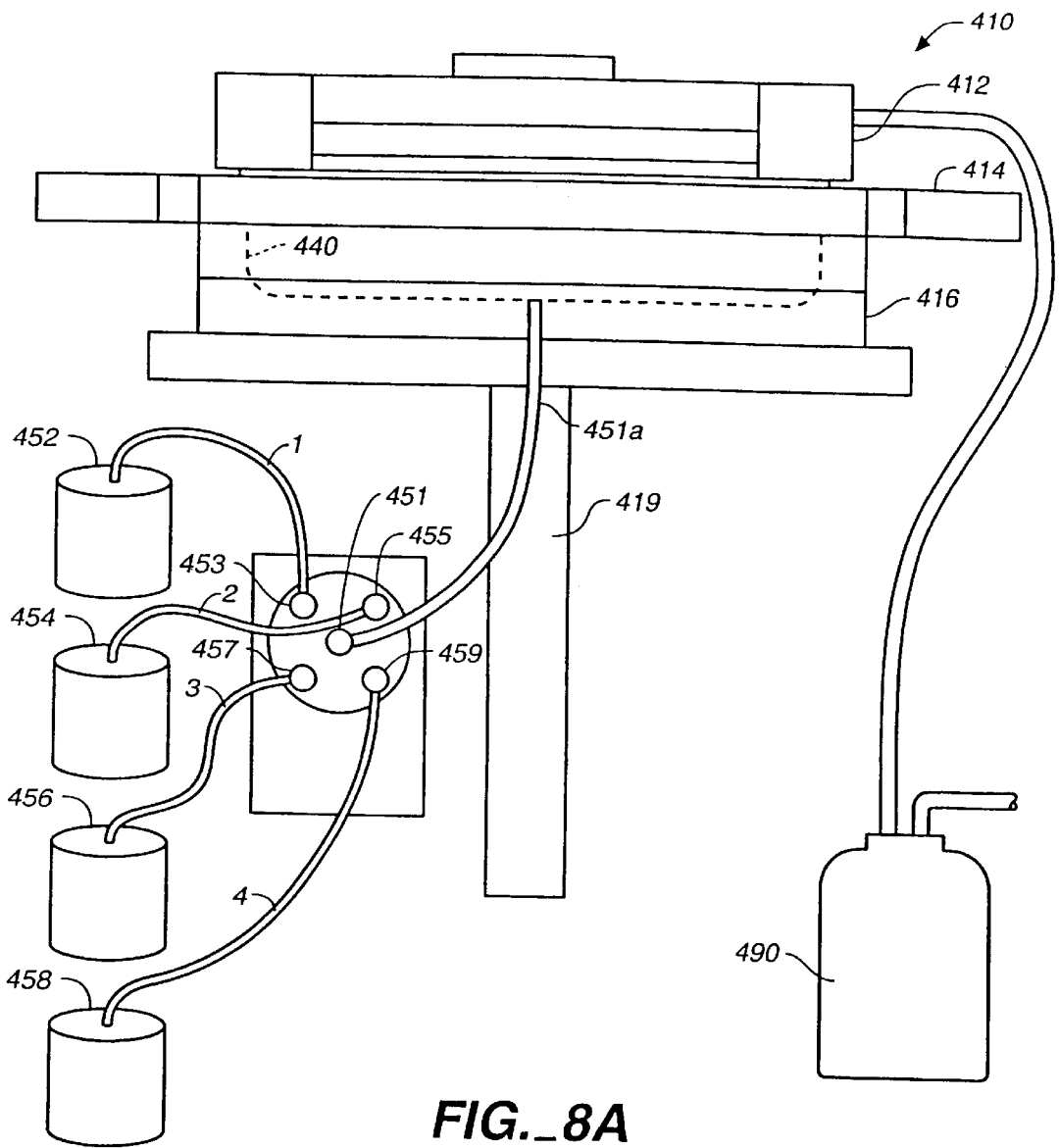
FIG._8A

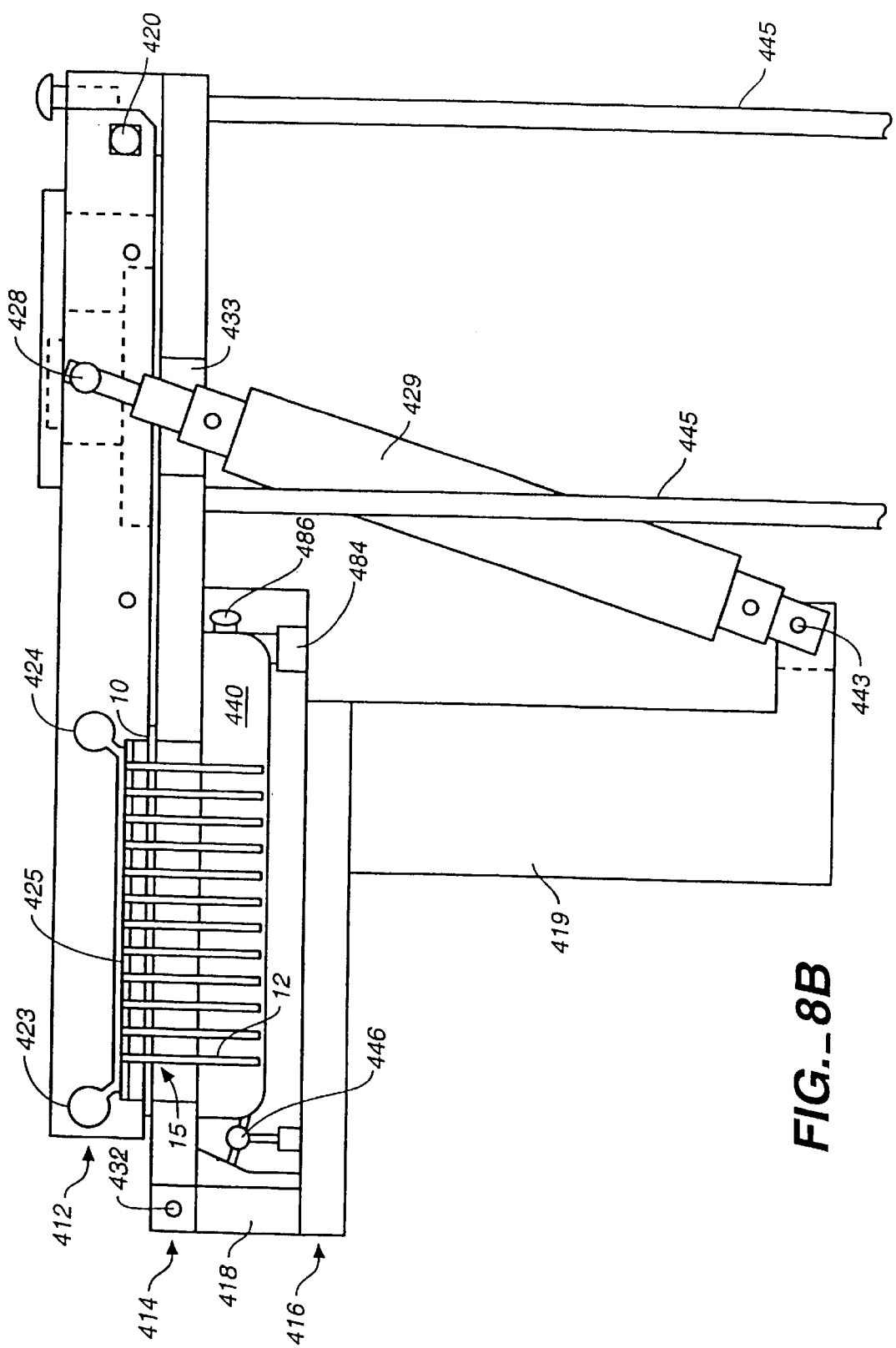
FIG._8B

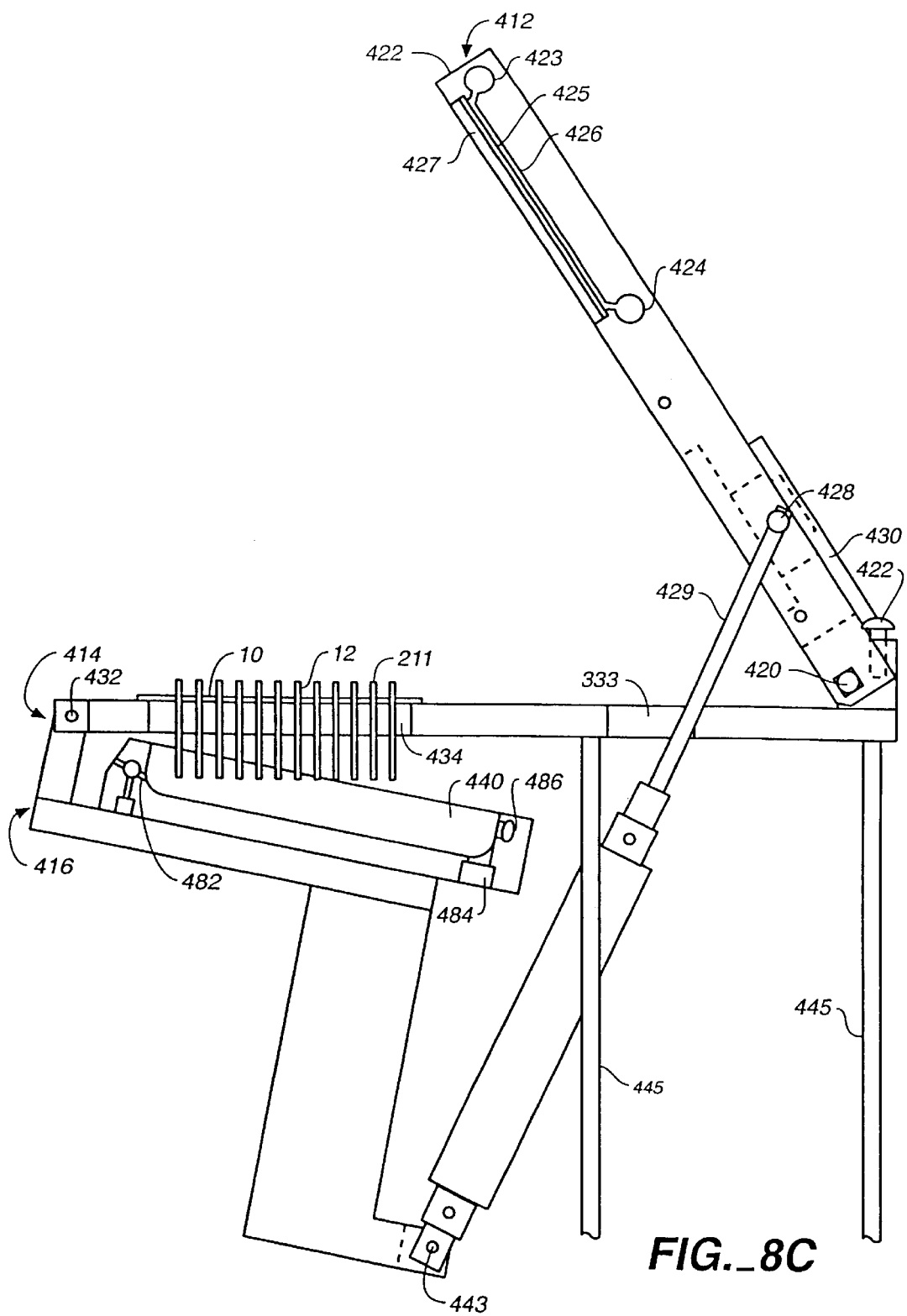
FIG._8C

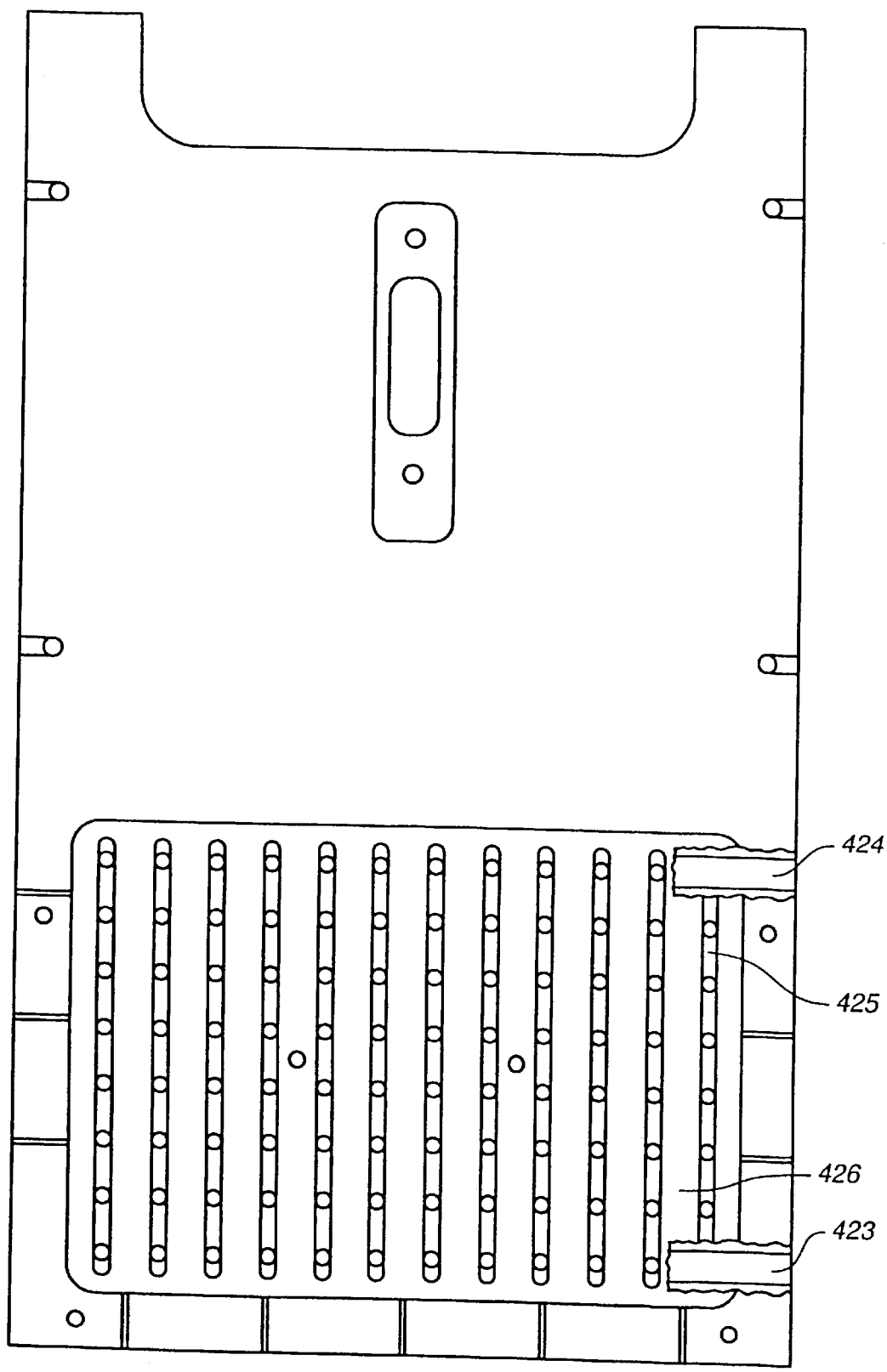
FIG._8D

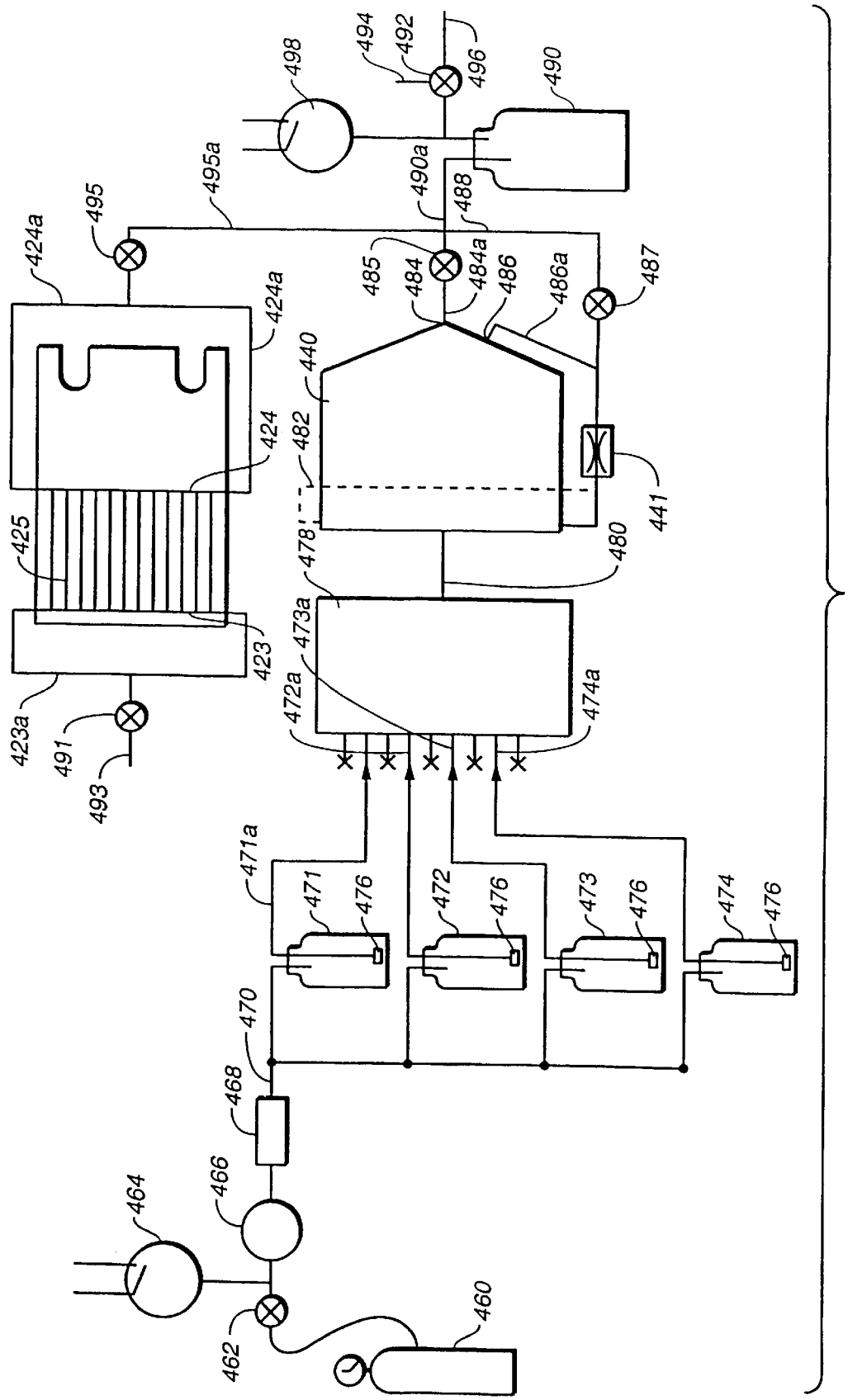
FIG._8E

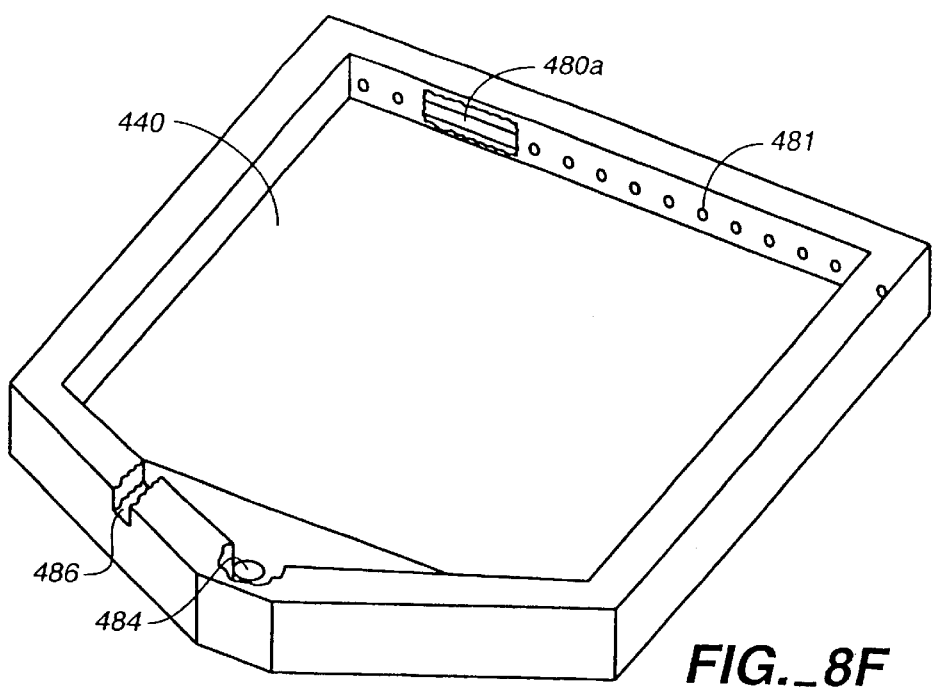
FIG._8F
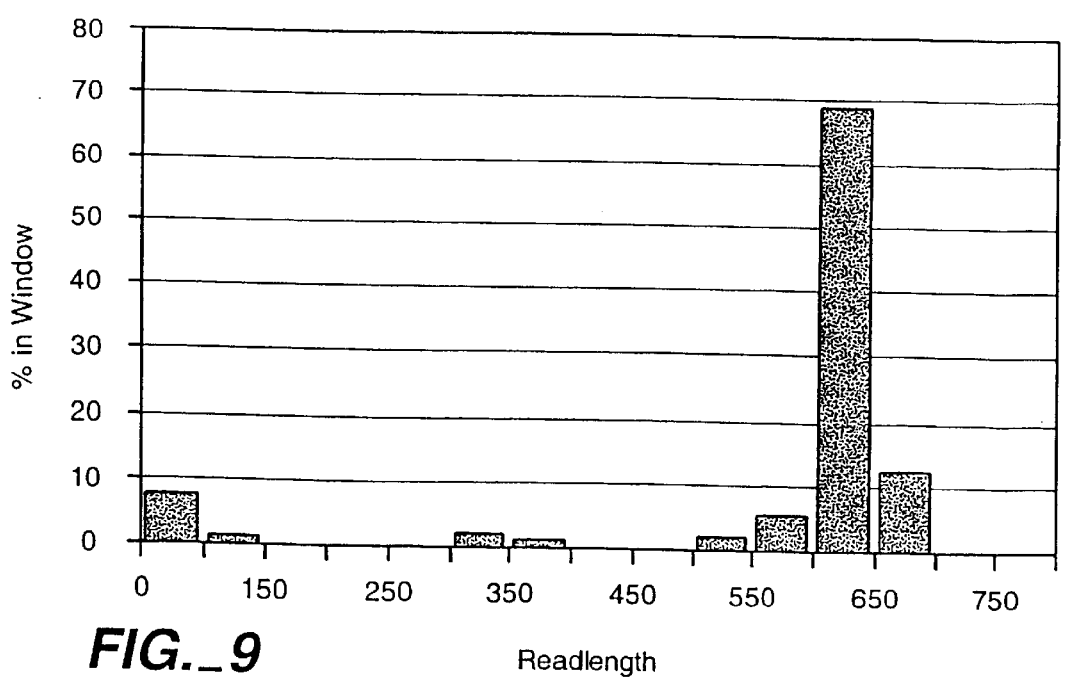
FIG._9

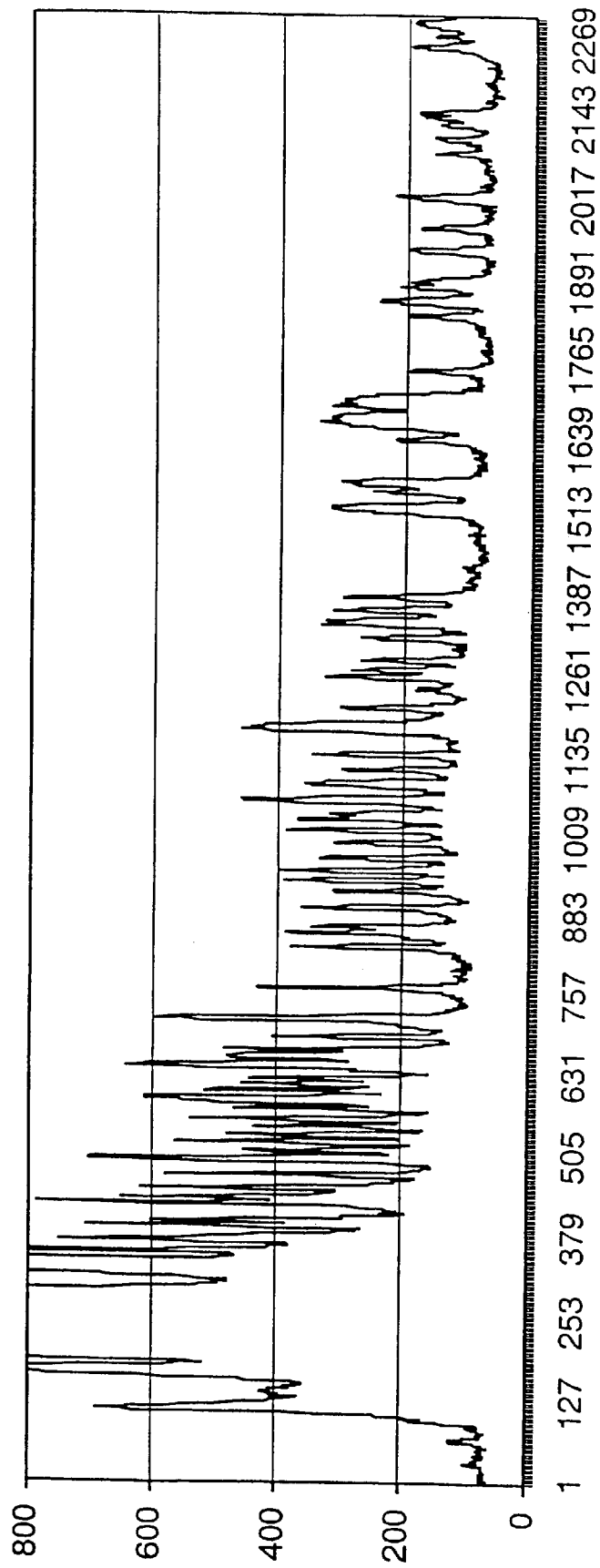
FIG._10

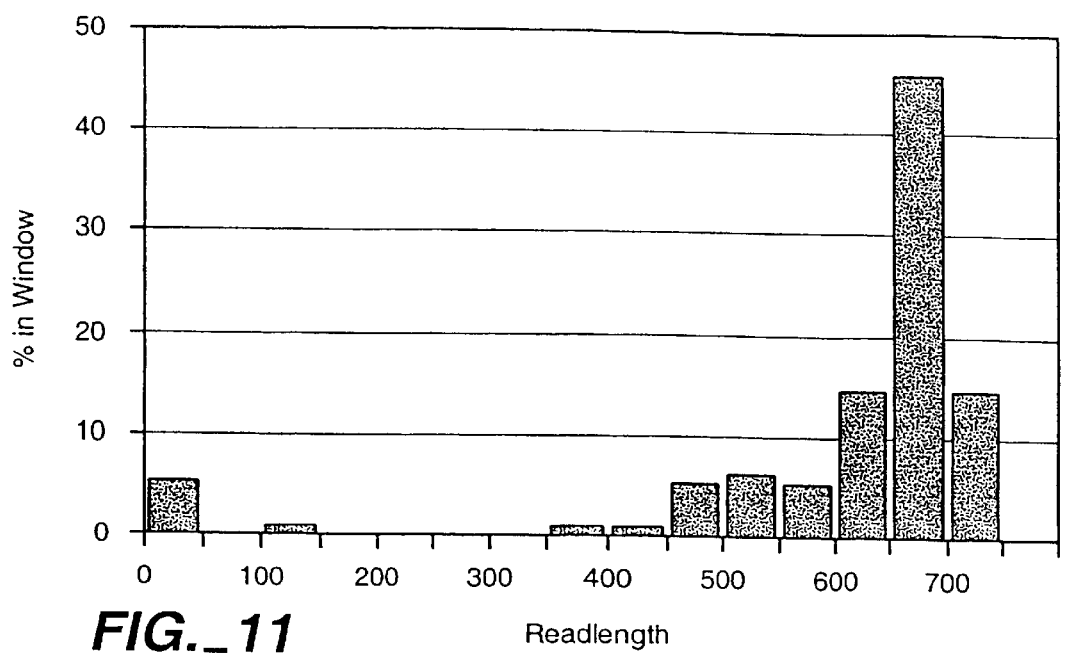
FIG._11
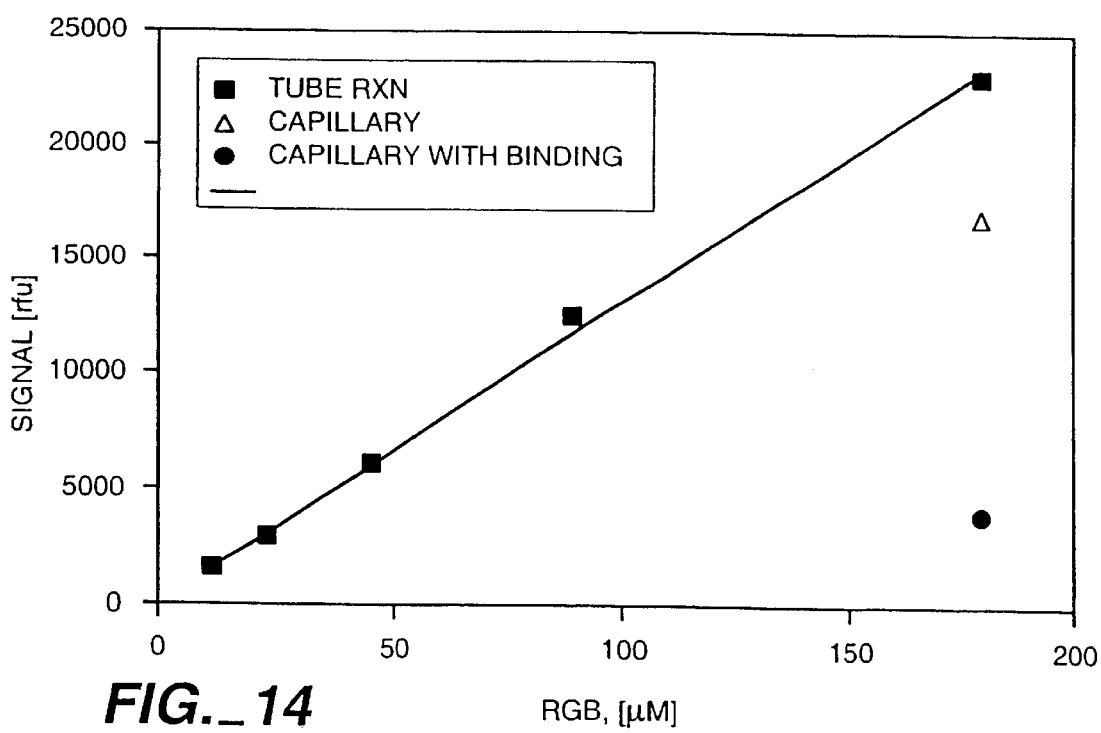
FIG._14

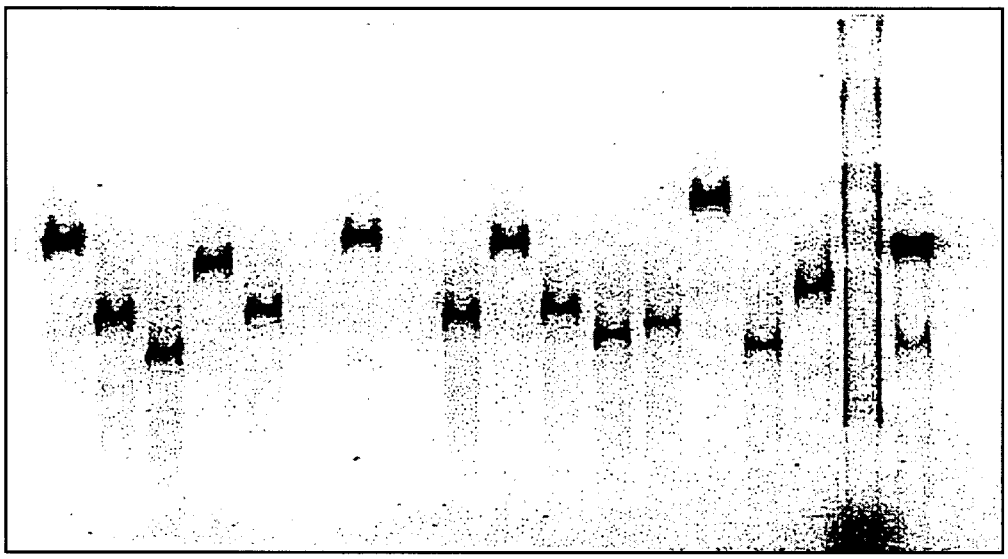
FIG._12A
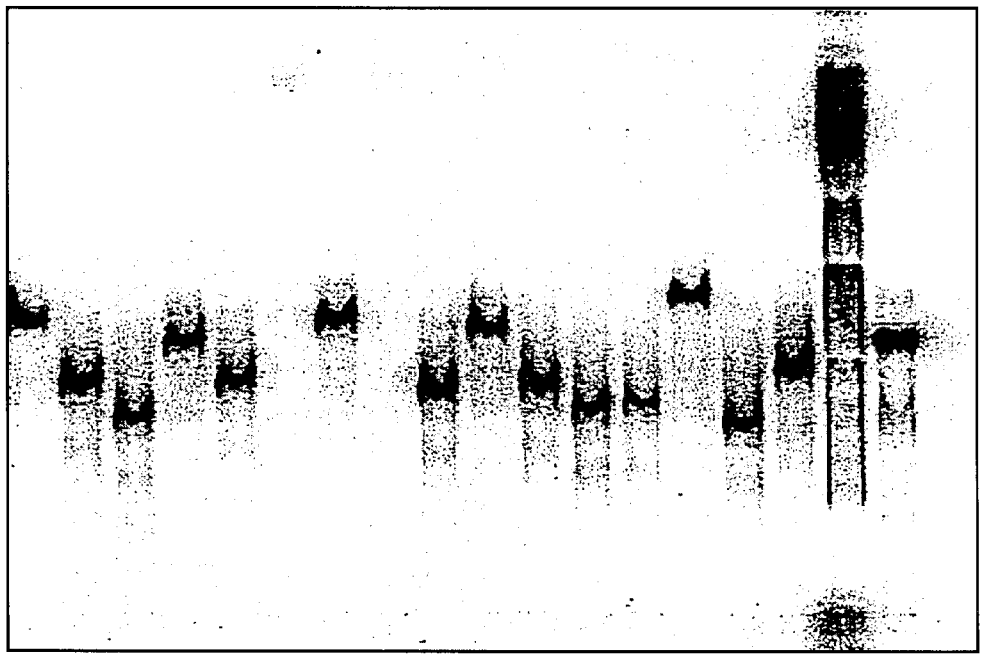
FIG._12B

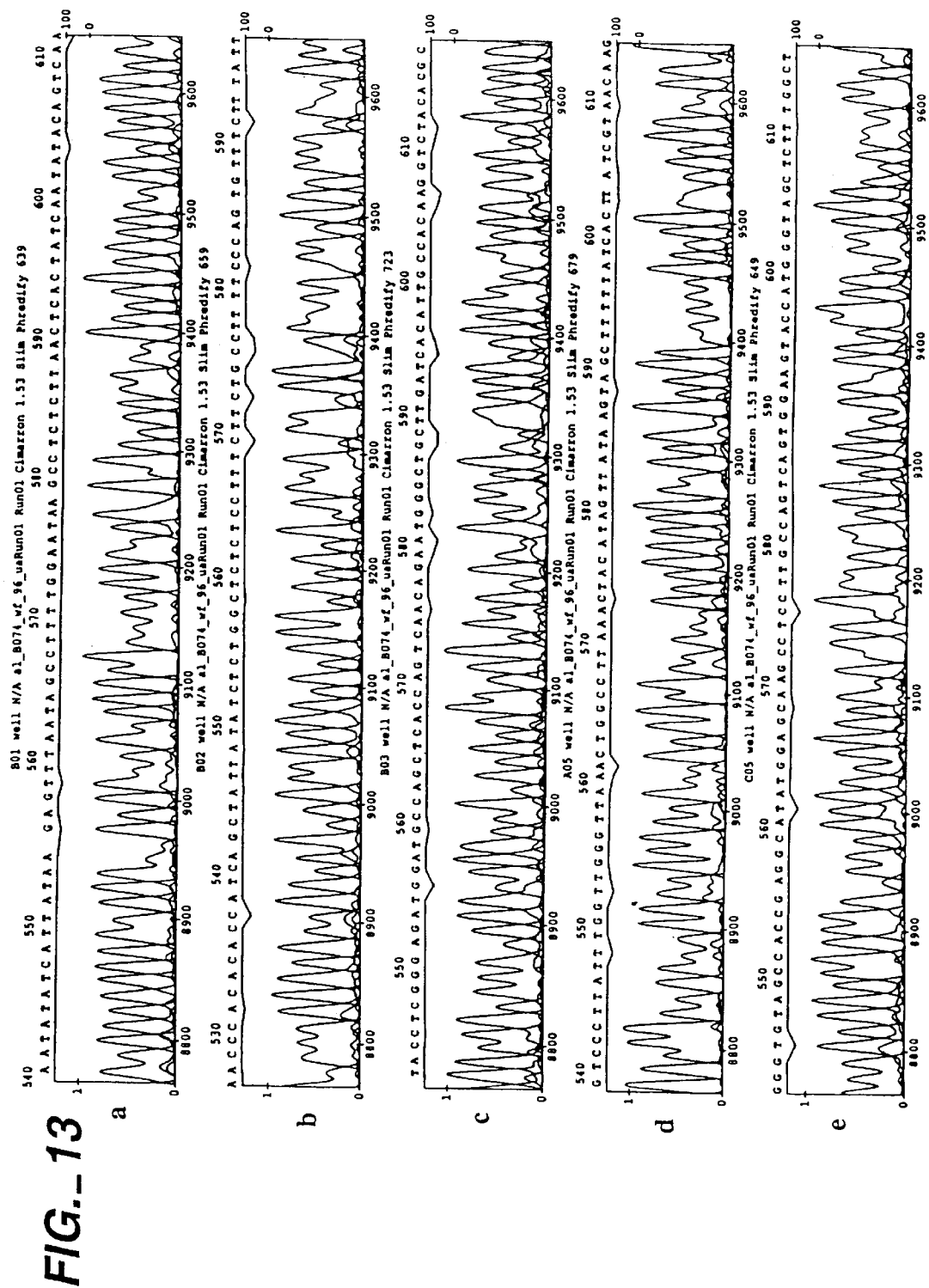
FIG._13

METHODS AND APPARATUS FOR TEMPLATE CAPTURE AND NORMALIZATION FOR SUBMICROLITER REACTION

CROSS-REFERENCE TO RELATED APPLICATIONS

This application claims priority from U.S. Provisional Application Ser. No. 60/146,732, filed August 2, 1999, and CIP U.S. Ser. No. 09/577,199, filed May 23, 2000, now U.S. Pat. No. 6,423,536 B1, the disclosures of which are incorporated herein by reference in their entireties.

STATEMENT REGARDING FEDERALLY SPONSORED RESEARCH

This invention was made with government support. The government has certain rights in the invention.

FIELD OF THE INVENTION

This invention is in the field of biotechnology, and relates to methods and apparatus for preparing and performing small scale reactions, particularly small scale cycling reactions and isothermal reactions that use nucleic acid templates.

BACKGROUND OF THE INVENTION

The original goal of the federally-funded Human Genome Project had been to complete the sequence of the human genome at ten-fold coverage by the year 2005. With dramatic acceleration in pace, a partial draft has recently been presented.

Rather than decreasing, however, the need for rapid, inexpensive DNA sequencing will grow dramatically after the Human Genome Project is completed.

For example, there is growing interest in sequencing the genomes of non-human organisms, including bacteria, plants and animals. More importantly, the burgeoning fields of molecular pathology and pharmacogenomics will require the sequencing of multiple genes from individual patients. Molecular pathology relates to the diagnosis, and often formulation of a prognosis, for human diseases by identifying mutations in particular genes. Pharmacogenomics refers to understanding how allelic differences that exist in all human populations affect the therapeutic response, and susceptibility to side effects, of individuals to drugs. As the need to sequence genes from individual patients grows, so will the demand for point of care sequencing capability. There will need to be a shift from large, centralized, high throughput DNA sequencing facilities that only exist at well-funded academic research centers and genomics companies to small, less complicated, middle-throughput gene sequencing systems that can be installed in the majority of hospitals and clinics. This shift in the market for sequencing technologies will put a premium on reducing the cost of reagents and making the sample processing steps as simple and seamless as possible.

In the late 1970s, Sanger et al. developed an enzymatic chain termination method for DNA sequence analysis that produces a nested set of DNA fragments with a common starting point and random terminations at every nucleotide throughout the sequence. Lloyd Smith, Lee Hood, and others modified the Sanger method to use four fluorescent labels in sequencing reactions enabling single lane separations. This resulted in the creation of the first automated DNA sequencers, which used polyacrylamide slab gels for separations. More recently, fluorescent energy-transfer dyes have been used to make dye sets that enhance signals by 2- to 10-fold and simplify the optical configuration.

Automated fluorescent capillary array electrophoresis (CAE) DNA sequencers appear to be the consensus technology to replace slab gels. Capillary gel electrophoresis speeds up the separation of sequencing products and has the potential to dramatically decrease sample volume requirements. The 96-channel capillary electrophoresis instrument, MegaBACE™, which is commercially available from Molecular Dynamics (Sunnyvale, Calif.), uses a laser-induced fluorescence (LIF) confocal fluorescence scanner to detect up to an average of about 625 bases per capillary (Phred 20 window) in 90 minute runs with cycle times of two hours. Confocal spatial filtering results in a higher signal-to-noise ratio because superfluous reflections and fluorescence from surrounding materials are eliminated before signal detection at the photomultiplier tube (PMT). Accordingly, sensitivity at the level of subattomoles per sequencing band is attainable. Confocal imaging is also particularly important in microchip analysis systems using capillary electrophoresis, where the background fluorescence of a glass or plastic microchip may be much higher than that of fused silica capillaries. Capillary array electrophoresis systems will solve many of the initial throughput needs of the genomic community for DNA analysis. However, present methods for low volume sample preparation still present a significant barrier to increased throughput and reduced cost.

While fluorescent DNA sequencers are improving the throughput of DNA sequence acquisition, they have also moved the throughput bottleneck from sequence acquisition back towards sample preparation. In response, rapid methods for preparing sequencing templates and for transposon-facilitated DNA sequencing have been developed, as have magnetic bead capture methods that eliminate centrifugation. Thermophilic Archae DNA polymerases have been screened and genetically engineered to improve fidelity, ensure stability at high temperatures, extend lengths, and alter affinities for dideoxynucleotides and fluorescent analogs. These improvements have resulted in lower reagent costs, simpler sample preparation, higher data accuracy, and increased read lengths.

The sequencing community has also developed higher throughput methods for preparing DNA templates, polymerase chain reaction (PCR) reactions, and DNA sequencing reactions. Sample preparation has been increasingly multiplexed and automated using 96- and 384-well microtiter, multi-channel pipettors, and laboratory robotic workstations. In general, these workstations mimic the manipulations that a technician would perform and have minimum working volumes of about a microliter, although stand-alone multi-channel pipettors are being used to manipulate smaller volumes.

A typical full-scale sample preparation method for DNA shotgun sequencing on capillary systems begins by lysing phage plaques or bacterial colonies to isolate subcloned DNA. Under some circumstances it may be desirable to PCR-amplify the subcloned DNA insert to exponentially increase its concentration in the sample. Next, exonuclease I (ExoI) and arctic shrimp alkaline phosphatase (SAP) are added to perform an enzymatic cleanup reaction to remove primer and excess dNTPs that interfere with cycle sequencing. ExoI is used to degrade the single-stranded primers to dNMPs without digesting double-stranded products. SAP converts dNTPs to dNPs and reduces the dNTP concentration from 200 $\mu$M, as used for the PCR reaction, to less than 0.1 μM for use with fluorescent sequencing. The reaction is performed at 37° C. and then heated to 65° C. irreversibly denature the ExoI and SAP.

Because PCR amplification can produce excess template DNA for cycle sequencing, the ExoI/SAP treated PCR sample can be diluted five-fold before cycle sequencing. This reduces the concentration of contaminants into a range that causes less interference with capillary electrophoresis analysis. Cycle sequencing reagents are added, typically with fluorescently labeled dye primers or terminators and the reaction is thermal cycled to drive linear amplification of labeled fragments. Finally, after cycling, the samples are post-processed, typically by ethanol precipitation or spin filtration, resuspended in formamide, another denaturant, or water, and the sample is electrokinetically injected into the capillary electrophoresis system.

This workflow has resulted in a dramatic improvement in the performance of the MegaBACE™ system, and similar work flows currently appear to be the methods of choice for other capillary electrophoresis systems as well. Using actual samples from single plaques and colonies of human genomic random subclones or Expressed Sequence Tags (ESTs), this workflow with linear polyacrylamide as a separation matrix has improved the success rate of samples over 200 base pairs from about 60% to 85–90%, and has improved the average read length from about 400 to greater than 600 bases. Furthermore, this method has proven to be quite robust.

While the above sample preparation methods have greatly increased throughout, the cost of reagents remains a major component of the cost of sequencing. Capillary electrophoresis requires only subattomoles of sample, but presently samples are prepared in the picomole range. Reducing the reaction volume will therefore reduce the cost of DNA sequencing and still provide enough material for analysis. However, substantial reductions in reaction volume can only be achieved if satisfactory methods can be developed for manipulating and reacting samples and reagents. Ideally, such a method would be automated and configured to produce multiple samples at one time. Moreover, it would be desirable to integrate such a method as a module capable of interfacing with additional components, such as capillary electrophoresis and a detector for separation and analysis.

Several devices have been designed to aid in the automation of sample preparation. For example, U.S. Pat. No. 5,720,923 describes a system in which small cycling reactions take place in tubes with diameters as small as 1 mm. The tubes are subsequently exposed to thermal cycles produced by thermal blocks to effect the desired reaction. Multiple samples may be processed in a single tube by drawing in small amounts of sample, each of which are separated in the tube by a liquid which will not combine with the sample. Fluid moves through the tubes by means of a pump. These features are incorporated into a system which automatically cleans the tubes, moves sample trays having sample containing wells, and brings the tubes into contact with the wells in the sample trays.

U.S. Pat. No. 5,785,926 discloses a system for transporting small volumes of sample. In this system, at least one capillary tube is used to transport small amounts of sample. A precision linear actuator connected to a computer controlled motor acts as a pneumatic piston to aliquot and dispense liquid using the tube. The sample amount is monitored by an optical sensor that detects the presence of liquid within the capillary segment. The system includes a fluid station containing liquids to be deposited and a positioning device for positioning the transport capillary.

U.S. Pat. No. 5,897,842 discloses a system for automated sample preparation using thermal cycling. In this system a reaction mixture is pumped into a capillary tube. One end of the tube is sealed using pressure from an associated pump while the other end is sealed by pressing the tube against a barrier. The pump also serves to move fluid within the tube. Once the ends are sealed, the tube is exposed to thermal cycles. In this system a robotic transfer device moves the tubes between the sample preparation station where the pump loads the components of the reaction mixture into the tubes and the thermal cycling station.

In the systems discussed above, it is necessary to first mix together a sample, such as DNA template for sequencing, and reagents, prior to introducing the mixture into a reaction chamber. This intermediate mixing step inevitably requires additional reagent and sample handling steps that results in wastage. For example, if separate micropipets are used to dispense sample and reagent into a mixing chamber, small amounts of sample and reagent will be retained in the respective pipets, and reaction mixture will be retained in the mixing chamber. In a high throughput system the cost of this wastage and providing new or properly cleaned pipets and mixing chambers rapidly mounts. Extent of wastage is often exacerbated by the need to dispense relatively large volumes of liquids containing reaction components at low concentration as a strategy to compensate for inaccuracies in dispensing low volumes of higher concentration liquids. Usually, after the reaction mixture is formed, only a small proportion is required for analysis, and the remainder is discarded.

Thus, there exists a need for means by which a biological sample to be analyzed could be introduced into a reaction chamber without the need to first mix the sample with the reagents necessary to effect the reaction.

U.S. Pat. No. 5,846,727 discloses affinity-capture methods wherein template DNA is immobilized inside a glass capillary tube that serves as a reaction chamber for thermal cycling. The capillary is first prepared by immobilizing biotin molecules to the inner surface of the capillary, followed by charging the column with avidin or streptavidin which binds tightly the biotin. Template DNA to be sequenced is covalently linked to a biotin moiety by PCR, and is then exposed to the avidin inside the capillary. This results in immobilization of the template to the capillary wall through a biotin-avidin-biotin linkage. After unbound template is washed away, sequencing reagent is added, and the contents of the capillary are subjected thermal cycling to activate the sequencing reaction. In this manner it is unnecessary to mix template DNA with sequencing reagent prior to loading the capillary.

However, the method just described requires that biotin be linked to the template DNA by PCR, necessitating setting up and carrying out a reaction even before the sequencing reaction. This requisite preliminary step adds to the time and cost associated with acquiring the sequence data. Furthermore, the immobilization of the DNA is effectively irreversible because the biotin-avidin linkage is so strong it can only be broken using agents that denature avidin, a treatment that would also denature any other protein components in a reaction. As a result the template DNA must stay bound to the inner surface of the capillary. Because the DNA is not free in solution, additional time is required for reaction components to diffuse to the walls where they can interact with the DNA. Furthermore, when it is desired to recycle the capillary, it is necessary to remove the template DNA via denaturation of the avidin, washing and then recharging of the avidin in the capillary, all of which add to time and reagent costs.

Thus, there is continued need in the art for methods to introduce molecules into reaction chambers without an initial sample-reagent mixing step, without the need to attach an affinity capture moiety to all the molecules in the sample, and wherein template immobilization is reversible. In this way reagent costs would be minimized and processing speed maximized.

Capillary array electrophoresis systems and capillary electrophoresis microchip analytical systems can detect sub-attomoles of DNA sequencing reaction products. This extraordinary sensitivity comes at the cost of reduced tolerance, compared to slab gels, for deviations from the ideal amount of template DNA in the sequencing reactions. For example, if there is too little template DNA in the sequencing reaction, there will be poor yield of fluorescently labeled primer extension products. This results in weak signal strength when the reaction products are scanned by the laser. This prevents the software that analyzes the chromatogram from adequately performing spectral separation, resulting in shorter than average sequence read lengths; the reaction will have to be repeated or the sequence information will be lost.

Too much template DNA causes problems as well, due to overloading of the capillary. While there is adequate yield of fluorescently labeled reaction product, if the template is in excess, it competes with sequencing products for entry into the capillary during electrokinetic injection. The presence of the large template DNA molecules can result in an overall reduction, or sudden drop in capillary current, which can manifest itself in a variety of ways. Overloading can cause weak signal strength, late appearance of interpretable fluorescence intensity peaks in the chromatogram, and poor resolution of the reaction products because the fluorescence emission is broad and diffuse. All these effects lead to shorter reads and lower sequencing data quality.

The problem of overloading is typically solved by either diluting the sequencing reaction, or carefully titrating the amount of template DNA introduced into the sequencing reaction. While both these solutions are simple in principle, the former requires repeating the analysis of the reaction, and the latter is difficult to implement using conventional means in a high-throughput system. These means include detecting, and comparing to standard concentration curves, the quantity of fluorescent dye that binds DNA in a sample, or measuring the absorbance of ultraviolet light at 260 nm wavelength, which can be converted into an absolute measure of DNA concentration. Thus, there is continued need in the art for methods to titrate the quantity of template DNA for sequencing reactions to be analyzed using high-throughput capillary electrophoresis systems, where minimizing cost and maximizing speed are crucial.

There is an additional need for an automated system that is able to perform small-scale thermal cycling reactions in a highly parallel manner. The system should allow for rapid preparation of cycling reactions with minimal consumption of reagents. The combination of reducing the amount of reagents required for a reaction and reducing the time required for a reaction will greatly reduce the overall cost of reparation of cycling reactions.

SUMMARY OF THE INVENTION

It is, therefore, an object of the present invention to provide novel methods for introducing small amounts of nucleic acid, such as template DNA to be sequenced, into a reaction chamber in a manner that obviates prior mixing of the nucleic acid with reagents to generate a reaction mixture.

It is a further object of the present invention to provide methods useful for introducing small amounts of nucleic acid into a reaction chamber without use of affinity capture moieties attached to the nucleic acid or reaction chamber.

It is a further object of the present invention to provide methods of introducing small amounts of nucleic acid into a reaction chamber without irreversible binding of nucleic acid to the wall of the reaction chamber.

It is yet another object of the present invention to provide methods useful for obtaining predetermined approximate quantities of nucleic acid for use in a reaction, such as template DNA to be sequenced, without the need to determine the concentration of the nucleic acid in the solution from which the DNA was drawn. It is a particular object of the invention to provide methods to titrate the quantity of template DNA for use in sequencing reactions that are to be analyzed using high-throughput capillary array electrophoresis systems, where minimizing cost and maximizing speed are crucial.

It is a further object of the invention to provide an automated system that is able to perform small-scale thermal cycling reactions in a highly parallel manner.

In accordance with this invention, a method is provided by which predetermined, reproducible amounts of nucleic acid are captured from solutions having wide variation in nucleic acid concentration directly, yet reversibly, onto a surface of the reaction chamber, either for submicroliter reaction directly therein or for metered elution into a second chamber for subsequent use. In accordance with other aspects of the invention, apparatus and systems useful for performing the inventive methods are provided.

The present invention is based, in part, upon the novel use of the saturable, yet reversible, binding of nucleic acids to the surface of certain materials. This reproducible, saturable, yet reversible binding is used to control the mass of nucleic acid delivered as template to a subsequent reaction, without a required antecedent determination of the concentration of nucleic acid in the solution from which the nucleic acid is to be captured. In particular embodiments, the internal surface of a capillary is used to effect nucleic acid capture, permitting nucleic acid template to be captured directly in the chamber in which subsequent reaction is to be performed.

Thus, in a first aspect, the invention provides a method of introducing into an enzymatic reaction a predetermined approximate mass of nucleic acid, comprising: saturably capturing, directly onto an interior surface of a chamber in which said enzymatic reaction is to be performed, a predetermined approximate mass of nucleic acid from an excess thereof, and then removing the excess.

The methods of the present invention are articularly useful in submicroliter DNA sequencing reactions. Thus, in another aspect, the invention provides a method of performing a DNA sequencing reaction, comprising: immobilizing template DNA directly on a substrate, and then contacting the template DNA with a reaction mixture that effects the DNA sequencing reaction. In related aspects, the invention further provides a product of a DNA sequencing reaction effected by the above-described method, and a DNA sequence derived from the product of the DNA sequencing reaction.

In another aspect, the invention provides a method of verifying the sequence of template DNA in solution, wherein the solution has been, or is desired to be, contacted to a first substrate as part of a spatially addressable array, comprising: immobilizing the template DNA directly on a second substrate, wherein said template DNA is immobilized by contacting the second substrate with the solution of template DNA for time sufficient for the DNA to become immobilized, and then contacting said template DNA with a reaction mixture that effects said DNA sequencing reaction, wherein the composition of the template DNA solution to be contacted to said first and second substrates is essentially identical.

The invention further provides systems that advantageously utilize the capillary-based embodiments of the present invention to effect high throughput reaction. In one embodiment of this aspect of the invention, the system uses a capillary cassette comprised of a number of capillary tube segments arranged in parallel alignment. The tube segments extend through a substrate and are generally positioned with uniform spacing. The capillary cassette may be used both to meter reagents and as a reaction chamber in which the reaction is conducted.

The system of the present invention is useful for the preparation of sequencing reactions, but may also be used in highly parallel preparation of cell lysates, plasmid extraction, polymerase chain reactions, ligase chain reactions, rolling circle amplification reactions, screening compound libraries for drug discovery or compound activity, protein digestion/sequencing, ELISA, radioimmunoassays and other chemical or biochemical reactions or assays.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIG. 1 is a schematic of an integrated system for the preparation of cycle sequencing reaction products, which system can advantageously use the methods of the present invention;

FIG. 2 is a flow chart illustrating the steps in production of cycling reactions, the first step of which can advantageously be improved by use of the methods of the present invention;

FIG. 3A is a perspective view of a capillary cassette that is used in a high throughput embodiment of the present invention;

FIG. 3B is a perspective view of the capillary cassette of FIG. 3A inserted into a capillary cassette holder in a system for high throughput application of the methods of the present invention;

FIG. 3C is a flexible capillary cassette that advantageously can use the methods of the present invention;

FIG. 3D illustrates the capillary cassette of FIG. 3C bent to a curved orientation such that the capillary ends are in a curved pattern;

FIG. 3E is a microchip device containing channels, functionally equivalent to capillary tubes, for sample preparation, including the direct reversible immobilization of nucleic acid, according to the present invention;

FIG. 4A illustrates a dispense head for dispensing liquid from the capillary cassette of FIG. 3, for use in the present invention;

FIG. 4B shows an internal cross section of an air displacement dispense head of FIG. 4A;

FIG. 4C shows the dispense head of FIG. 4A with the dispense head closed;

FIG. 5A illustrates a top view of a centrifuge that can be used to dispense fluid from a capillary cassette of FIG. 3A;

FIG. 5B illustrates a cross-section of a rotor arm of FIG. 5A holding a swinging microplate bucket containing a capillary cassette inserted into a microtiter plate;

FIG. 6 shows a schematic of an air-based thermal cycling device with the capillary cassette and holder shown in FIG. 3B inserted into the temperature cycling device, for performing parallel reactions that advantageously can use the template capture and normalization methods of the present invention;

FIG. 7A shows an internal cross section of an air-based thermal cycler with integrated capillary cassette sealing membranes, which can advantageously be used with the template capture methods of the present invention;

FIG. 7B shows a perspective detail of the air-based thermocycler of FIG. 7A, with the lid raised to illustrate the chamber into which the capillary cassette is inserted;

FIG. 7C shows a cross section of the cassette compartment with the capillary cassette inserted into the internal chamber of the thermal cycler of FIG. 7A;

FIG. 8A is a front view of a capillary cassette wash station useful in high throughput performance of the methods of the present invention;

FIG. 8B is a side view of the capillary cassette wash station of FIG. 8A with the wash manifold lowered and the wash tank raised;

FIG. 8C is a further view of the capillary wash station of FIGS. 8A and 8B with the wash manifold raised and the wash tank lowered;

FIG. 8D is an interior cross-section of the wash manifold;

FIG. 8E is a schematic plumbing diagram of the wash station;

FIG. 8F is a top perspective view of the wash tank;

FIG. 9 shows a histogram of the percent success versus read length window for the sequencing analysis of example 1;

FIG. 10 is an electropherogram of the reaction products of example 2;

FIG. 11 shows a histogram of the percent success versus read length window for the sequencing analysis of example 3;

FIG. 12A shows a scanned gel image of electrophoretically separated PCR products prepared at full volume;

FIG. 12B show a scanned gel image of electrophoretically separated PCR products prepared at a nanoscale volume (500 nL);

FIG. 13 is an electropherogram of analysis of sequencing mixtures prepared by performing PCR at 500 nL volumes, a cleanup reaction at full volumes, followed by cycle sequencing reactions performed at 500 nL;

FIG. 14 is a graph comparing signal strength of an isothermal reaction for products prepared in tubes, capillaries, and capillaries using surface binding;

DETAILED DESCRIPTION OF THE INVENTION

Figure 15:
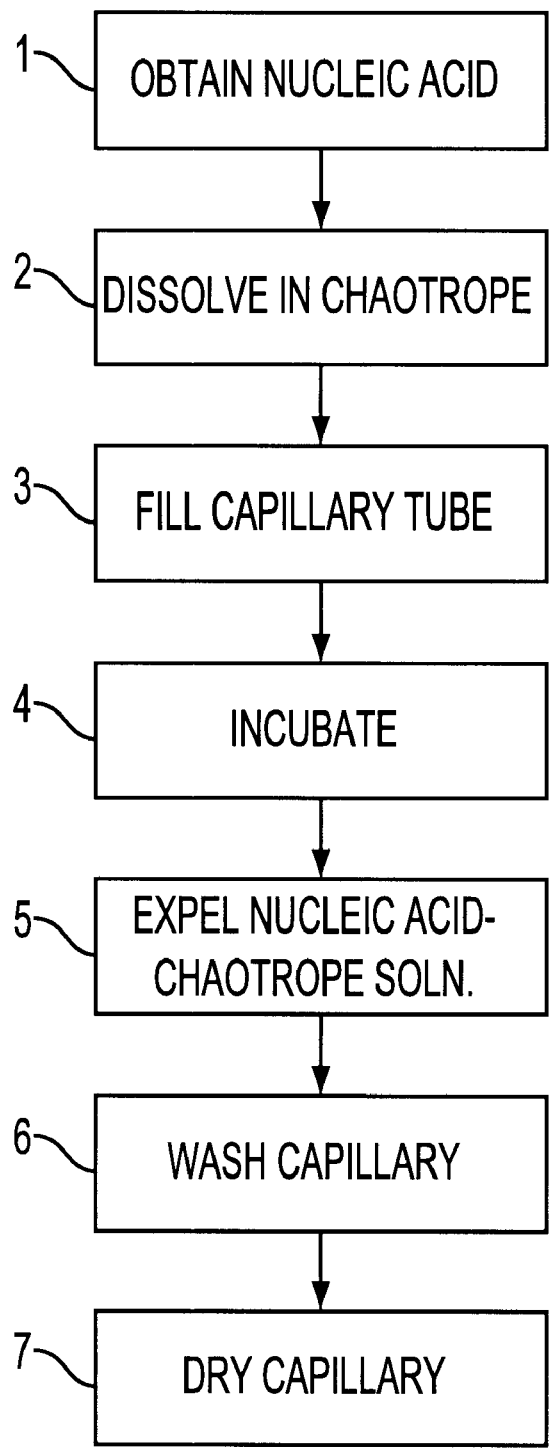
FIG. 15 is a flowchart explaining the methodology for preparing capillary tubes in which nucleic acid is reversibly directly immobilized.

In order that the invention herein described may be fully understood, the following detailed description is set forth.

The present invention is based, in part, upon the novel use of the saturable, yet reversible, binding of nucleic acids by certain materials to control the mass of nucleic acid delivered as template to a subsequent reaction, without a required antecedent determination of the concentration of nucleic acid in the solution from which the nucleic acid is to be captured. In particular embodiments, the internal surface of a capillary is used to effect nucleic acid capture, permitting nucleic acid template to be captured directly in the chamber in which subsequent reaction is to be performed.

ADVANTAGES OF THE PRESENT INVENTION

The present invention is described herein with particular reference to its use for performing DNA sequencing reactions, especially in the context of a high-throughput sample processing system employing capillary electrophoresis, for which the methods and apparatus of the present invention are particularly advantageous. However, it will be clear to the skilled artisan, as will be described in more detail below, that this invention can be used in the course of performing many types of biochemical and chemical reactions using DNA, as well as RNA, as the substrate.

As disclosed in detail below, the present invention provides methods for reversibly immobilizing nucleic acid directly on the inner surface of a reaction chamber, such as a glass capillary tube, or the functional equivalent thereof. After immobilization and other processing steps, the nucleic acid is ready to be used in a chemical, biochemical or enzymatic reaction performed inside the capillary tube. Alternatively, the nucleic acid can be eluted and expelled from the capillary so as to dispense a controlled amount of nucleic acid for subsequent use.

For successful analysis of DNA sequencing reactions using highly sensitive capillary electrophoresis systems, such as the MegaBACE™ system (Molecular Dynamics, Sunnyvale, Calif.), it is important to use consistent, predetermined amounts of template DNA in the reactions, so that the amount of template is neither too low nor too high. By employing capillary tubes with consistent DNA binding capacity, it is possible to "normalize" the amount of template DNA used across all reactions, thereby ensuring that all start with a similar quantity of template. Although normalization can be accomplished in other ways, use of capillary tubes results in dramatic savings of time by reducing the steps necessary to ensure consistency.

Although nucleic acid binding is an inherent property of glass surfaces, it will be appreciated that the capture surface can be modified to alter its binding capacity or binding selectivity. For example, for capturing non-modified DNA, major binding forces are hydrophobic forces, charge-charge (electrostatic) forces, and hydrogen bonding. Thus, to capture non-modified DNA, vinyl groups can be added to the capture surface by reaction in the solution phase, propyl amine groups can be added by CVD, other amines, preferably tertiary amines, can be added by known reactions to maximize the charge-charge interaction. In other alternatives, oligo d(T) can be covalently linked to aminated surface, increasing capture of poly(A) mRNA. A spacer of the general form $C_n$ can be added between the silicon surface and the functional groups. For each of these, the characteristics and/or binding capacity can be altered by changing the concentration of the functional groups.

An additional advantage of the present invention is that it is useful for reducing the number of processing steps associated with, and the quantity of nucleic acid and reagents needed for, carrying out a reaction with nucleic acid, especially in the context of a high-throughput sample processing system. For example, for a DNA sequencing reaction, it is necessary to combine template DNA with a reaction mixture comprising sequencing primer, DNA polymerase, dideoxynucleotides, dNTPs, buffers, salts and water, prior to performing thermal cycling that activates the reaction. Typically, this involves preparing a 20 $\mu l$ reaction by aliquoting the reaction mixture into a tube, followed by the addition of 200 ng template DNA. The pipet tip used to aliquot the DNA is typically discarded to avoid contamination of the DNA stock. The components are then mixed, thermal cycled and analyzed.

According to an embodiment of the present invention, a capillary tube is filled with a DNA solution, resulting in the reversible immobilization of 5 ng of the template inside the capillary. After several processing steps, the capillary is then filled with 500 nl of reaction mixture, which causes the template to elute from the inside of the tube into the mixture. The capillary is then sealed and thermocycled, with subsequent analysis of the reaction products by a high sensitivity capillary electrophoresis system. Because the capillary serves simultaneously as a pipettor that is filled by capillary action, and as a reaction chamber, it is unnecessary to separately aliquot, with dedicated pipetting systems, either template DNA solution, or the reaction mixture. It is only necessary to provide a stock of each into which the capillary is dipped to fill it. This saves processing steps and materials such as disposable pipettor tips. It also saves reagent that would otherwise be carried over during processing steps, and not introduced into a reaction.

It will also be apparent that a sequencing reaction performed in the capillary can be accomplished in only 1/10 to 1/40 of the reaction volume, and therefore 1/10 to 1/40 the cost for reagents. Collectively, these advantages result in reduced processing, increased speed, and reduced cost. In the design of high-throughput sample processing systems, capillaries, or functional equivalent thereof, can be arranged in parallel, in ways well known to those skilled in the art, to increase the number of reactions that can be processed simultaneously. The scale of the benefits enjoyed employing the various embodiments of the present invention disclosed herein grow in proportion to the number of samples processed.

Reversible Direct Immobilization of Nucleic Acid in a Reaction Chamber

Figure 16:
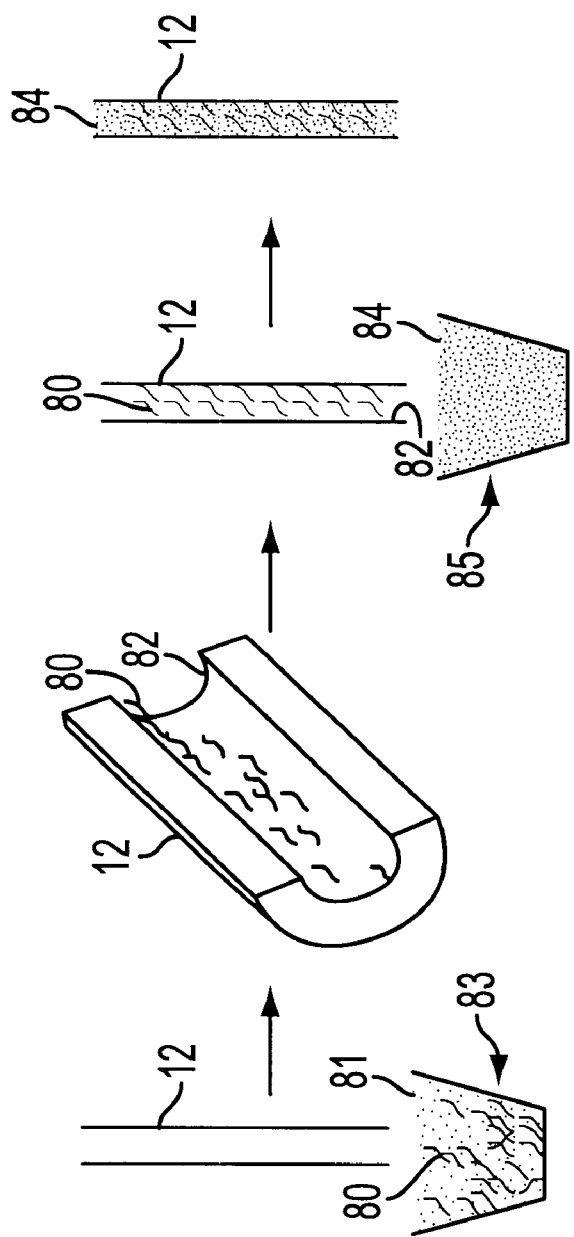
FIG. 16 illustrates an embodiment of the method of the present invention.

FIG. 15 is a flowchart, and FIG. 16 is a schematic that shows the steps associated with embodiments of the instant invention, whereby nucleic acid is reversibly immobilized to the inner surface of a reaction chamber, such as a glass capillary tube. Reaction chambers prepared in this way can then be used to carry out a sequencing reaction with nucleic acid, to effect another type of enzymatic or biochemical reaction with nucleic acid, or for dispensing a predetermined quantity of nucleic acid onto a substrate, such as a microtiter dish well, or into an analysis instrument, such as a capillary electrophoresis device.

With reference to FIG. 15, and FIG. 16, in step 1 the nucleic acid sample is prepared from a suitable source, after which, in step 2, the nucleic acid 80 is dissolved in a solution 81 containing chaotropic ions. In step 3, the reaction chamber is filled with the nucleic acid-chaotrope solution and incubated, in step 4, for sufficient time to allow reversible binding of the nucleic acid 80 to the inner surfaces 82 of the reaction chamber 12. In step 5, the nucleic acid-chaotrope solution is removed, followed by washing, step 6, and drying, step 7, of the reaction chamber. At this point the reaction chamber is useable. Part 12 refers to a capillary tube, or more broadly, a reaction chamber, including capillary tubes and structures equivalent in function thereto. Part 80 refers to DNA, or more broadly, nucleic acid, including DNA and RNA and derivatives thereof.

The process begins by obtaining nucleic acid, FIG. 15, step 1, from a suitable source. The nucleic acid may be deoxyribonucleic acid (DNA), ribonucleic acid (RNA) or derivatized forms of these molecules. Nucleic acids can be isolated and purified according to methods well known in the art (see Current Protocols in Molecular Bioloqy, John Wiley & Sons, Inc., 2000, Edited by Fred M. Ausubel et al., ISBN 0-471-50338-X) from a variety of living organisms or self-replicating systems that rely on living cells. Cells can be eukaryotic cells, including human and non-human mammalian cells, non-mammalian animal cells, plant cells and fungal cells. Additionally, eukaryotic cells can be free living single celled organisms, such as amoebae or other parasites. Cells can also be prokaryotic cells including bacteria and archaebacteria. Nucleic acids can also be obtained from viruses, including RNA and DNA viruses, and viruses that infect animal cells, plant cells, fungal cells, and bacterial cells. Nucleic acids can also be produced according to chemical synthetic methods well known in the art.

After obtaining template nucleic acid from the appropriate source, the nucleic acid, FIG. 16 80, is resuspended and/or dissolved into a solution containing a chaotropic agent, FIG. 15, step 2, and FIG. 16 82. The chaotropic agent is desirably at sufficiently high concentration (e.g., about 0.5 M to 8.0 M) to effect the reversible binding of the nucleic acid, but not so high as to cause the nucleic acid, or the chaotrope itself to precipitate out of the solution under all of the conditions to which the solution is subjected in carrying out the invention.

A chaotropic agent is a substance that affects the partitioning of molecules from a nonaqueous to an aqueous phase due to the disruptive effect that the substance has on the local structure of water. Chaotropic agents are salts of chaotropic ions, and are highly soluble in aqueous solutions. At sufficiently high concentration in aqueous solutions the chaotropic ions provided by such salts cause nucleic acids to lose secondary or tertiary structure, and double-stranded nucleic acids to melt (i.e., strand-separate). It is hypothesized that chaotropic ions have these effects by disrupting hydrogen-bond networks existing in water, causing the denatured form of the nucleic acids to be more thermodynamically stable as compared to the structure of more highly ordered structures (e.g. the double helix) that exist in a typical aqueous environment.

As described previously by Vogelstein et al., Proc. Natl. Acad. Sci. USA 76, 615–619 (1979) and by Chen and Thomas, Anal. Biochem. 101, 339–341 (1980), in the presence of a sufficiently high concentration of chaotropic ions (e.g. about 0.5 M to about 8.0 M), nucleic acids will reversibly bind certain substances, such as silica. The mechanism of nucleic acid binding to silica may involve chaotropic ion disruption of the water structure at the surface of the negatively charged silica, allowing a cation (e.g. $Na^+$ or $K^-$) mediated salt bridge to form between it and the negatively charged phosphate backbone of the nucleic acid strand. To effect nucleic acid silica binding, a chaotropic agent may be used singly or as a mixture of two or more chaotropes. The salt bridge is not a permanent bond and can be disrupted when the ionic concentration in the proximity of the bond is lowered. In this way, nucleic acid can be eluted from silica or similar material with water or other suitable low ionic strength aqueous buffer.

Chaotropic ions include guanidinium, iodide, perchlorate and trichloroacetate. Chaotropic salts include sodium perchlorate, potassium perchlorate, sodium bromide, potassium bromide, sodium iodide, potassium iodide, sodium thiocyanate, potassium thiocyanate, guanidine thiocyanate, sodium isothiocyanate, potassium isothiocyanate, guanidine hydrochloride, guanidine isothiocyanate, lithium chloride, sodium trichloroacetate, and potassium trichloroacetate. Other substances with chaotropic properties include dimethylsulfoxide (DMSO), urea, and the tetra-amine halides, including tetraethylamine chloride.

After dissolving the nucleic acid in the solution of the chaotrope, the nucleic acid-chaotrope solution, FIG. 16 83, is introduced into a reaction chamber, FIG. 15, step 3, and FIG. 16 12.

For the purpose of reducing the cost of reagents used to effect the sequencing reaction, the reaction chamber will typically be of very small volume, desirably from about 1–1000 nanoliters (nl), more desirably from about 10–500 nl, most desirably from about 100–500 nl.

In most circumstances, the reaction chamber is configured so that solutions can be introduced into it passively, by taking advantage of capillary action. Capillary action is the phenomenon by which the elevation of a liquid rises where it is in contact with a solid, such as the sides of a tube, and is most marked in capillary tubes, i.e., tubes of very small diameter. Capillary action depends on the forces created by surface tension and by wetting of the sides of the tube. If the forces of adhesion of the liquid to the solid (wetting) exceed the forces of cohesion within the liquid (surface tension), the liquid will rise up the tube, i.e., it will rise above the hydrostatic level. Alternatively, the solution can be introduced into the reaction chamber actively, such as by pumping using positive or negative atmospheric pressure.

It is simplest and most economical to take advantage of capillary action to fill the reaction chamber with the nucleic acid-chaotrope solution, in which case a capillary tube serves as the reaction chamber. If the bore of the capillary is of known and uniform areal cross section, then the volume of the tube is easily calculated, being linearly proportional to its length. Thus, a capillary tube reaction chamber of given total volume is obtainable by cutting the tubing to the desired length given by the calculation. In accordance with the laws of fluid dynamics however, care must be taken that the density of the solution is not so great, its surface tension so low, and the diameter of the tubing insufficiently small, that the column of solution cannot overcome gravity, and thereby fails to fill the tube.

During filling, one end of the tube is dipped into the nucleic acid-chaotrope solution, FIG. 16 83, that is usually provided in volume excess over the total volume of any tube to be filled. In this manner, the tube is filled in one step, reducing the chance of bubble formation at the inlet. The opposite end of the capillary must be open, or otherwise able to allow air to escape from the filling tube.

It is not obligatory that the outside of the reaction chamber approximate the form of a tall thin cylinder, as it does with a capillary tube. Rather, as will be apparent to the skilled artisan, the functional equivalent of a capillary tube can be manufactured in a variety of ways. Throughout the specification, the term capillary tube should be understood to represent not only that structure commonly referred to as a capillary tube, but also any structure that is functionally equivalent thereto. For example, a tunnel, channel or groove can be formed that is configured so that fluid can fill it by capillary action, or by the direct application of some force, e.g. positive or negative pressure, or centrifugal force. The tunnel, channel or groove can be formed mechanically, chemically, thermally, or by other means known to the skilled artisan. A channel or tunnel can be formed by removing material from a matrix, e.g., using a drill bit, laser, or chemical etching As illustrated in FIG. 3E, a groove or channel 78 in the surface of a substrate 72, such as a glass slide of any shape and dimension, can be cut with a saw, or formed by laser ablation or chemical etching to create a structure called a chip or microchip 70. For example, grooves in a silicon wafer can be formed by photolithographic methodologies known in the art, and grooves in glass slides can be etched using hydrofluoric acid.

If a groove or similar depression 78 is formed in the surface of a substrate 72, it will usually be advantageous to cover it with a cover 74 to form an enclosed space. Covering the groove or depression 78 ensures that there is maximal surface area for the fluid to interact with, thereby promoting the capillary action, minimizes the opportunity for contaminants to contact the reactants, and creates a vapor barrier to ensure that during any elevation in temperature of the reaction, such as during thermal cycling, the tendency of the reaction to vaporize is minimized.

Covers 74, which can be comprised of material identical to, or different from, that of the substrate 72 in which the groove is cut, can be applied using a variety of means known in the art. For example, the cover 74 can be glued to the substrate using an epoxy, cyanoacrylate or other type of glue. The cover can be welded by melting it and underlying material until they fuse, through the application of heat or light. The cover 74 can also be fixed in place mechanically, such as with a clamp, or even magnetically.

The material of which the reaction chamber is comprised is advantageously a material to which template DNA, or other nucleic acid, reversibly and saturably binds in the presence of a sufficiently high concentration of chaotropic ions. Frequently, the reaction chamber is comprised of glass, especially when configured as capillary tubing. High quality glass capillary tubing is readily available in a range of interior dimensions from a variety of manufacturers, including Polymicro Technologies (Phoenix, Ariz., USA).

If comprised of a fragile, hydrophilic material like glass, it may be advantageous to coat the outside of the capillary tubing with a polymer material, such as a polyimide. A polyimide coating provides a protective layer that protects the capillary tubing from abrasions and breaking by bending. Polyimide also creates a hydrophobic layer on the outer surface of the capillary which can help prevent the adherence of aqueous reaction mixtures when the capillary is filled by dipping it into a reaction mix; this helps prevent wastage of reagents. Other potential coatings are acrylates, silicones, fluoropolymers, and aluminum.

Many types of glass may be used including alkali-borosilicate glass, alumina-silicate glass, barium flint glass, barium-borate glass, borosilicate glass, borate glass comprising $B_2O_3$, germinate glass comprising $GeO_2$, chalcogenide glass, silicate glass comprising $SiO_2$, silica glass, fused silica glass, synthetic fused silica glass, quartz (crystalline $SiO_2$), fused quartz (amorphous $SiO_2$), doped synthetic fused silica (doped with trace elements such as germanium, fluorine, boron, phosphorous, and titanium), lanthanum glass, optical glass, phosphate glass, and soda-lime glass.

Alternatively, the reaction chamber can be comprised of a metal or metalloid, materials that, like glass, can be fashioned into capillaries or wafers. Suitable pure and alloyed metals include magnesium, aluminum, titanium, vanadium, chromium, manganese, iron, cobalt, nickel, copper, zinc, gallium, zirconium, niobium, molybdenum, palladium, gold, silver, cobalt, niobium, indium, rhodium, tin, steel, stainless steel, and bronze. Suitable pure and alloyed metalloids include silicon, germanium, arsenic, and gallium arsenide.

The reaction chamber can also be comprised of carbon in its multiple allotropes, including graphite, diamond, $C_{60}$ and related allotropes comprising, for example, nanotubes, or comprised of organic compounds such as plastic. For these materials, it may be necessary to derivatize the carbon or plastic in such a fashion as will support the reversible binding of nucleic acid to the plastic in the presence of chaotropic ions.

After the reaction chamber, such as glass capillary, FIG. 16 12, has been filled with nucleic acid-chaotrope solution 83, the solution is incubated for such time and under such conditions that at least a portion of the DNA in the solution reversibly binds to the inner surface, FIG. 16 82, of the chamber or tube, FIG. 15, step 4. In other embodiments, irreversible binding can be effected.

Without wishing to be bound with theory, it is believed, as discussed above, that if the inner surface is glass containing $SiO_2$ (silica), in the presence of a sufficiently high concentration of chaotropic ions the nucleic acid most likely forms salt-bridge type bonds with the silica via the phosphate backbone. Usually, binding is allowed to proceed at about room temperature (about 24° C.), but other temperatures may be chosen as is deemed appropriate, so long as the effectiveness of binding is not significantly hampered, and so long as neither the DNA nor chaotrope precipitates from the solution.

After the nucleic acid in the nucleic acid-chaotrope solution has had the opportunity to bind to the inner surface 82 of the reaction chamber or tubing, the solution containing unbound DNA and the chaotrope is then removed 5, the inner surface is washed 6 with washing solution, and then remaining traces of liquid from the wash solution is removed by drying 7.

The greater proportion of nucleic acid-chaotrope solution is removed from the chamber by a variety of means including application of positive or negative air pressure, or by centrifugation to expel the solution.

Washing is performed to purify the bound nucleic acid by removing excess, unbound nucleic acid, chaotropic agent, and any impurities that may have contaminated the nucleic acid. It is important to remove the chaotropic agent because these ions can severely interfere with most subsequent chemical and biochemical reactions, even at very low concentrations. Washing can be performed in a variety of ways. For example, a capillary tube can be filled by capillary action, after which the washing solution is expelled in similar manner by which the nucleic acid-chaotrope solution was removed. Alternatively, a reaction chamber can be filled and emptied by pumping of the wash solution. Sufficient volume of washing solution is used to essentially eliminate the presence of all contaminants. After washing, the wash solution is removed from the chamber or tube.

The composition of the washing solution is chosen so that it does not remove by elution any substantial portion of the nucleic acid that has become bound to the inner surface of the chamber or tubing, and is typically a solution of an alcohol with pure water. Suitable alcohols include the lower molecular mass alcohols methanol, ethanol and isopropanol. The concentration of alcohol is high enough that elution of nucleic acid minimized, and is preferably at least 50%, more preferably at least 60%, and most preferably at least 70% volume by volume. Typically, ethanol is used at concentration greater than about 70%–80% volume by volume.

The washing solution can also comprise a salt, preferably in the form of a buffer, such as an acetate buffer, or a tris-EDTA buffer (containing, e.g., 10 mM Tris-HCl and 1 mM ethylenediamine-tetraacetic acid (EDTA), pH 8.0). The salt can have the effect of buffering pH so that the pH is in the range of about 6.5–8.5, and also stabilizing the binding interaction between DNA and the inner surface of the chamber or tube during washing.

It is frequently desirable to remove essentially all traces of the liquid from any small volume of the wash solution remaining in the chamber or capillary tubing by drying. Although low concentrations of some components of the liquid, such as ethanol, tend not to significantly interfere with subsequent biochemical reactions, higher concentrations can interfere. Drying can be effected by subjecting the chamber or tube to a high enough vacuum so that the liquid vaporizes and is carried away. Alternatively, a dry gas, such as air, nitrogen or argon, can be forced at pressure through the chamber or tube to promote the evaporation of the liquid. The drying gas can be warmed to further promote evaporation.

After drying, the reaction chamber, now bearing reversibly immobilized nucleic acid, can be used immediately to perform a biochemical reaction with the nucleic acid, or stored, under appropriate conditions, for future use. Reaction chambers prepared according to the steps discussed above can be advantageously used to normalize the amount of a nucleic acid to be used in parallel reactions, dispense predetermined amounts of DNA or RNA onto a substrate, and to perform nanoscale DNA sequencing reactions, as well as many other types of reactions with DNA and RNA. However, as will be clear to the skilled artisan, these particular applications should not be seen as limiting the scope of uses to which such reaction chambers can be put.

Use of the Present Invention in an Automated System

Reaction chambers in the form of capillary tubes can be processed as illustrated in FIG. 15 and used singly, but it will frequently be advantageous to combine multiple capillary tubes in parallel fashion, so as to be able to increase sample throughput, particularly in an automated system. For this purpose, capillary tubes can be conveniently organized into a capillary cassette; the greater the density of capillary tubes per cassette, the greater the potential sample throughput. An apparatus, such as that described in copending U.S. application Ser. No. 09/577,199, can be used to automate the processing steps illustrated in FIG. 1, as well as any subsequent steps associated with carrying out reactions with the immobilized nucleic acid, including capillary filling, emptying, washing, drying, and or thermal cycling. Used in this way, the cassette becomes an automated, fixed-volume parallel pipettor, allowing all the capillary tubes to be filled simultaneously from the wells of a sample plate by capillary action.

Capillary cassette 15 is shown in FIG. 3A. The capillary cassette is comprised of a number of capillary tubes extending through a substrate 10. It is preferred that the capillary cassette have at least one row of eight capillary tubes and that the capillary tubes have equal spacing. The capillary cassette shown has substrate 10 with 96 capillary tubes arranged in an 8 by 12 array, with spacing of the tubes matching the spacing of the wells of a 96 well microplate.

The capillary tubes 12 extend through a substrate 10 and preferably are arranged in a uniform pattern. The capillary tubes are of equal length and extend through the substrate in a substantially parallel orientation such that each of the two opposing ends of the capillary tubes 12 are coplanar and the planes defined by the ends of the capillary tubes 12 are substantially parallel to the substrate 10. The spacing of the capillary tubes may be uniform and selected to match the center-to-center spacing of wells on a microplate. For example on a standard 96 well microplate the capillary tubes would be arranged with a 9 mm center to center spacing, on a 384 well microplate the capillary tubes 12 would be arranged with a 4.5 mm center to center spacing. Higher density capillary formats, compatible with 1536 well microplates or plates with even higher well density, should also be possible. The capillary tubes 12 are preferably secured within the substrate such that the length of capillary tubes 12 extending from one side of the substrate 10 are shorter than the length of the capillary tube on the opposite side of substrate 10. The length of the capillary tubes 12 on the shorter side of the substrate may be matched to the depth of wells in a microplate, such that the length of the shorter side is a shorter length than the depth of a well in a microplate. This feature enables the capillary cassette to be inserted into a microplate such that the substrate 10 rests against the top lip of the multiwell plate and the capillaries on one side of the substrate may extend into the multiwell plate without touching the bottom. For example, in a 96 well microplate the capillary tubes may be disposed on a substrate such that the shorter side of the capillary tube extending from the substrate may be inserted into wells in a microplate without the capillary touching the bottom of the well. This ensures that liquid dispensed into a well is clear of the capillary to prevent re-entering t he capillary.

The capillary cassette substrate 10 may be made of a fiberglass board or other rigid or semi-flexible material. The capillary tubes 12 may be inserted through evenly spaced holes in the substrate and secured with adhesive. In one embodiment, the length and width of the substrate are similar to the length and width of a standard 96 well microplate. This simplifies adapting automated systems designed for manipulation of microplates to handle the capillary cassette

Accurate Control and Normalization of the Quantity of Nucleic Acid to be Used in a Biochemical Reaction When undertaking to carry out a biochemical reaction with nucleic acid, it is often crucial for the success of the reaction that the amount of input nucleic acid be known with precision. This allows the experimenter to properly calculate the appropriate ratio of other reaction components, such as enzymes. For example, as discussed in the Background section, if too much template DNA is used in a sequencing reaction to be analyzed with a capillary electrophoresis system, poor quality sequencing data often results. Nucleic acid concentration in a stock sample is relatively easily determined by measuring light absorption at 260 nm, or measuring the amount of dye binding relative to standard curves. However, both these approaches use up a portion of the sample and neither approach is easy to implement in the context of a high-throughput sample processing system. Fortunately, the present invention is useful for precisely controlling the amount of nucleic acid to be used for a variety of applications.

If during the binding reaction occurring in the reaction chamber, the nucleic acid-chaotrope solution is allowed to stay in contact with the inner surface of the chamber or tube for sufficient time, and if the nucleic acid is at high enough concentration in the solution, it is possible to saturate the available binding sites on the inner surface of the chamber or capillary with nucleic acid. This is known as saturable binding. As long as the amount of nucleic acid in solution prior to incubation exceeds the binding capacity of the inner surface of the chamber, a fixed, maximal quantity of nucleic acid will be immobilized, regardless of the amount of nucleic acid initially in the solution. In this way, if the concentration of nucleic acid in solution exceeds a minimum, it is not necessary to know the actual concentration; the amount of nucleic acid bound will be determined solely by the binding capacity of the reaction chamber. Accordingly, if the nucleic acid in a capillary tube that was saturably bound is eluted into a known volume of liquid, the concentration and amount of nucleic acid in the liquid is knowable with a high degree of accuracy.

Thus, it is possible to use the present invention to obtain, or measure out, accurately known, small, consistent quantities of nucleic acid, based on the binding capacity of capillary tubes or other configurations of reaction chamber. For example, if is desirable to carry out a reaction using 10 ng of nucleic acid, it is only necessary to obtain a capillary tube, or other reaction chamber, with a total of 10 ng of nucleic acid binding capacity. Then, the capillary is filled with nucleic acid-chaotrope solution wherein both the nucleic acid and chaotrope are at sufficiently high concentration to support saturable binding in reasonable time. After the incubation, emptying, washing and drying steps are complete, the experimenter is confident that the capillary contains 10 ng of nucleic acid which can be eluted for dispensing, or left to reside in the capillary for future use.

Typically, the binding capacity, or amount of nucleic acid that can be saturably bound to the inner surface, is determined empirically. For example, a known amount of test nucleic acid is labeled with a radionuclide, such as $^{35}S$, $^{33}P$ or $^{32}P$, according to methods known in the art. After labeling, the specific activity of the labeled nucleic acid is determined to establish a ratio of disintegrations per minute per mass unit, or concentration unit of nucleic acid. The labeled nucleic acid is then dissolved in a solution containing chaotropic ions at a predetermined concentration. A standard reaction chamber, representative of a general supply, is then tested. For example, a predetermined length of glass capillary tubing is cut and filled with the labeled nucleic acid-chaotrope solution. After sufficient time for saturable binding to occur, the capillary is emptied and washed. Then, the amount of radioactivity retained inside the tube is measured, and, with knowledge of the specific activity of labeling, converted to an amount of nucleic acid. This factor can then be used to calculate the amount of nucleic acid that will be retained in any length of capillary tubing cut from the same lot, so long as similar conditions for binding are used in any subsequent experiment.

An advantage of using the present invention to accurately obtain a predetermined quantity of nucleic acid is to normalize quantities of nucleic acid for subsequent use. This advantage is especially significant if it is necessary to process many samples. For example, in the current state of the art, it is not practical, when preparing different template DNAs for sequencing, to ensure that the concentration of the templates is the same. Thus, according to prior methods it was necessary to normalize the different template DNA samples, by separately determining the DNA concentration in each prep, and diluting the DNA to the proper concentration for each and every sample. This is especially important for capillary electrophoresis because of the sensitivity of that technology to overloading of the capillaries with template DNA. The requirement for normalization of the template DNA added significant time and cost to obtaining high quality DNA sequence data using this system, or required that researchers accept increased failure rates.

However, the present invention allows very rapid normalization to minimize differences in starting template concentration. To normalize the different templates to a predetermined concentration it is only necessary to provide functionally equivalent capillary tubes (one for each template) with a known, saturable DNA binding capacity, and template DNA-chaotrope solution with sufficiently high concentration of both DNA and ions that all the DNA binding sites in the capillary become occupied within a reasonable period of time. After emptying and washing, all the capillaries will contain about the same quantity of template DNA, and are thus normalized.

As will be apparent to the skilled artisan, if it is not desirable to saturate all the possible nucleic acid binding sites inside a reaction chamber, it is possible to control the amount of nucleic acid that is reversibly bound. This is possible because the kinetics of the binding reaction depend on a number of variables, including nucleic acid concentration, average nucleic acid molecular size, solution pH, chaotropic ion concentration, the number of available binding sites on the inner surface of the reaction chamber and temperature. Thus, with empirical analysis, it is possible for the skilled artisan to establish binding conditions that result in the consistent, predictable, reversible binding of a predetermined quantity of nucleic acid that does not saturate all available nucleic acid binding sites inside a reaction chamber.

DNA Sequencing for Capillary Electrophoresis

The advantages of the present invention are beneficially applied to carrying out DNA sequencing reactions, particularly for analysis with highly sensitive capillary electrophoresis systems such as MegaBACE™. To use the present invention for DNA sequencing, template DNA must be immobilized in capillary tubes, or the functional equivalent thereof. Template DNA is that DNA for which the sequence of constituent bases is to be determined. Template DNA can be single stranded, or double stranded, wherein two complementary DNA strands are hybridized together, and knowledge of the sequence of one strand can be used to infer the sequence of bases in the other strand according to the rules of Watson-Crick base pair complementarity.

Template DNA is typically obtained directly from self-replicating genetic systems, grown in a host, into which the DNA fragment to be sequenced was cloned. Alternatively, the template can be obtained from any source by amplifying a particular DNA sequence using the polymerase chain reaction, or a functionally equivalent linear or exponential amplification process.

Self-replicating genetic systems include episomal elements, such as plasmids containing an origin of replication, or bacteriophage (e.g. lambda or M13), both of which can replicate inside bacteria, such as *E. coli*, after transformation or infection, respectively. Plasmids harboring template DNA are obtained by breaking open the bacteria in which they have replicated to sufficiently high copy number, and isolating the plasmid from the supernatant. Bacteriophage released into bacterial culture supernatant after lysing the host bacteria are collected, and the DNA isolated by breaking open the bacteriophage particles. It is also possible to grow episomal agents containing mammalian origins of replication in mammalian cells, followed by isolation of the DNA according to the Hirt method.

Due to the substantial difference in molecular mass between plasmid or other episomal DNA, as compared to genomic DNA, use of capillary tubes as reaction chambers offers a convenient method by which to rapidly purify plasmid DNA from contaminating genomic DNA when both are released after lysing bacteria or other type of cells. Briefly, a mixture of plasmid and genomic DNA is combined in solution of chaotropic ions. A capillary into which the plasmid is desirably immobilized is dipped into the solution. The plasmids, because of their small mass, easily pass into the bore of the capillary as it fills, thereby interacting with the glass walls to establish salt-bridges and become immobilized. In contrast the genomic DNA, being of extremely large molecular mass, is excluded from the small bore of the capillary, and is thus separated by size exclusion from the plasmids.

As mentioned, template DNA can also be obtained without the need for cloning steps by amplifying a DNA fragment directly from an appropriate source, such as a virus, a prokaryotic cell, including bacteria, or eukaryotic cell, including mammals, other animals, or plants.

After the template DNA, FIG. 16 80, is reversibly immobilized directly to the inner surface 82 of a glass capillary tube 12, in accordance with the methods of the present invention, the capillaries are filled with the sequencing reaction mixture 84 that effects the DNA sequencing reaction. The reaction is carried out according to techniques well known in the art, whereby the products of the DNA sequencing reaction are labeled with fluorescent dyes. Well established in the art is the Sanger dideoxynucleotide chain termination technique. Briefly, a primer complementary to sequence in the template DNA molecule is permitted to hybridize to the template. Then DNA polymerase extends the primer by reading the sequence of bases in the template, by adding dNTPs to the 3' end of the growing primer. However, dideoxynucleotide triphosphates that lack the hydroxyl group characteristic of the corresponding dNTP prevent the further addition of bases to the growing strand. As a result the chain terminates. The pattern of terminated chains in a chromatogram permits the experimenter to infer the sequence of bases in the template. The terminated reaction products are fluorescently labeled either by conjugating a fluorophore to the primer that is extended, or alternatively, by conjugating a fluorophore to all the dideoxy terminators that, when incorporated into growing DNA chain, result in termination of primer extension.

In recent years, use of energy transfer, dye-coupled fluorophore systems, comprised of a light acceptor dye and fluorescence emitter dye, have improved the performance of laser scanned sequencing systems. Each dideoxy terminator is labeled with two dyes. One of these dyes, fluorescein, absorbs light energy from incident laser light produced by the laser in the sequencing machine, and transfers the collected energy via radiationless energy transfer to an acceptor dye. Each of the four chain terminators, ddG, ddA, ddT, and ddC, have a different acceptor dye coupled with the fluorescein donor. The acceptor dyes, for example, rhodamine 110, rhodamine-6-G, tetramethyl rhodamine, and rhodamine X, then emit light at their characteristic wavelengths. The fluorescence is detected by the instrument allowing identification of which nucleotide caused the termination event. Use of the energy transfer system results in more efficient excitation of the acceptor dyes than direct excitation by the laser, resulting in greater sensitivity. As an alternative to fluorescently labeling the dideoxy terminators, it is possible to label the sequencing primer. If using this system, energy transfer dyes may be used as well by conjugating to the primer a donor dye and an acceptor dye. An example of a donor dye to be conjugated to a primer is 5-carboxy-fluorescein (FAM), and examples of acceptor dyes to be conjugated to primers are rhodamine 110 (R110) for cytosine, 6-carboxyrhodamine (REG) for adenine, N,N, N',N'-tetramethyl-5-carboxyrhodamine (TAMRA) for guanine, and 5-carboxy-X-rhodamine (ROX) for thymine. The energy transfer dye-coupled fluorophore system is discussed in greater detail in issued U.S. Pat. Nos. 5,688,648, 5,707,804, 5,728,528, 5,853,992, 5,869,255, and 6,028,190, all of which are herein incorporated by reference in their entireties.

The capillary, FIG. 16 12, containing the immobilized template DNA 80 is filled by capillary action by dipping it into a reservoir 85 filled with the reaction mixture. The reaction mixture 84 contains all the components at the appropriate concentration to effect the sequencing reaction, including water, salts, buffers, primer, DNA polymerase, dNTPs and dideoxy terminators. Without wishing to be bound by theory, at present it is hypothesized that as the aqueous mixture ascends the capillary, the immobilized DNA likely rehydrates. Furthermore, because the ionic strength of the salts in the mixture is relatively low, the salt-bridge causing the DNA to be immobilized is disrupted by the water molecules and the DNA is eluted from the inner surface of the capillary, and diffuses into the reaction mixture. Alternatively or in addition, the DNA desorbs during the thermocycling reactions. Whatever the mechanism, physical mixing of the DNA into the mixture is not necessary for performance of the reaction.

Once the capillary is filled, the ends are sealed to prevent vaporization of the liquid contained inside, followed by thermal cycling to activate multiple rounds of the sequencing reaction, so as to generate the fluorescently labeled product to be analyzed. Sealing of the capillary and thermal cycling may be effected in multiple ways, as will be apparent to the skilled artisan. If, as will often be the case, it is desirable to perform multiple sequencing reactions in parallel, the experimenter can use a high-throughput apparatus, such as that disclosed in the copending application U.S. Ser. No. 09/577,199, which is hereby incorporated by reference in its entirety. The disclosed apparatus provides means both for sealing multiple capillary tubes arranged into a cassette format, and for effecting thermal cycling of the sequencing reaction mixtures contained in the capillaries.

After the sequencing reaction is completed the reaction products are expelled from the capillary tubes, typically in preparation for analysis by capillary electrophoresis.

Typically, the reaction product is expelled onto a substrate, or into some form of holder for liquid, such as a well of a microtiter dish, from which a capillary electrophoresis system may sample the product for analysis. However the skilled artisan will recognize that it is possible for the reaction product to be expelled directly from the reaction capillary into the electrophoresis capillary. Reaction product may be expelled from the reaction capillaries by the application of centrifugal force, electrokinetically, by the application of positive or negative air pressure, or by other means known in the art.

Furthermore, the reaction product can be expelled onto a substrate adapted for other types of analytical process, such as a MALDI (matrix-assisted laser desorption/ionization) or SELDI (surface-enhanced laser desorption/ionization) substrate for mass spectrometric analysis.

During electrophoresis of the fluorescently labeled sequencing reaction products, a laser scans a window in the capillaries carrying the products and excites the fluorophores. Light emission by the fluorophores is captured and converted into intensity and light frequency data that is stored in a computer memory. After scanning and reading is complete, the computer assembles a chromatogram representing all the reaction products detected by the scanning system. The data in the chromatogram is processed by computer software that interprets the chromatogram to infer the sequence of nucleotide bases in the starting template DNA. The sequence output is then stored in a computer data file, either in random access memory or on a dedicated long term memory device, such as floppy disk, ZIP disk, JAZ disk, hard disk, CD-ROM, computer tape, etc. For the convenience of end users of the data, the computer file containing the sequence data can be stored on a computer server that can be accessed from remote client computers. When the file is transferred it is represented as a data signal associated with a carrier wave carried through copper or fiberoptic telephone lines, cable television lines, or by radio waves.

Once emptied, the capillary tubes are recycled for immobilization of new nucleic acid samples, such as DNA template to be sequenced. Recycling of the tubes requires washing to remove detrimental traces of the previous reaction, including reaction products, reaction mixture components and the immobilized nucleic acid.

Typically, the wash solution is an aqueous wash solution of low ionic strength such that any remaining immobilized nucleic acid will tend to be eluted and carried away. Double distilled water is effective. The wash solution may be heated to increase the effectiveness of washes, and the number of washes and/or volume of wash solution per wash cycle can be varied as necessary to maximize washing effectiveness. Capillaries can be filled with wash solution by capillary action and then emptied using the same methods by which reaction product is expelled. If washing is to be effected by electrokinetic pumping, then the wash solution must contain some minimum concentration of ions. Alternatively, a mechanical pump can be used to drive wash solution through the capillaries.

The washing can also be accomplished by a mechanical capillary cassette washer as disclosed in commonly owned and copending U.S. patent application Ser. No. 09/577,199, filed May 23, 2000, the disclosure of which is incorporated herein by reference in its entirety.

The design for a capillary tube washing device designed to wash multiple capillaries arranged into a cassette is disclosed in the copending application U.S. Ser. No. 09/577, 199, herein incorporated by reference in its entirety.

After the aqueous washes, an alcohol wash, usually comprising a high concentration of ethanol is used to remove most traces of water and other components of the wash solution. The capillaries are then dried, typically by drawing warm dry air through them, after which they are ready for storage or reuse.

For some applications, it is important that essentially no nucleic acid remain from a previous reaction in the capillaries. One example is PCR, whereby old residual template DNA could be exponentially amplified leading to contamination of a new reaction. In such cases, the recycling process can comprise steps effective at destroying traces of nucleic acid. Such means include filling the capillary with a solution containing an exonuclease and incubating for such time as is necessary to digest any nucleic acid. Other means include chemical degradation of the nucleic acid, such as by washing with highly acidic or basic solutions; contact with bleach; irradiating the capillary with ionizing radiation; or baking to high temperature. After destroying residual nucleic acids, the capillaries would typically be washed using standard solutions.

One application, though by no means the only one, whereby parallel processing using capillaries in cassettes will prove useful is the confirmation of the sequence of DNA, often PCR products, for high throughput de novo sequencing, such as for discovery of single nucleotide polymorphisms (SNPs). For SNP discovery, the methods and apparatus of the present invention make possible "deep" sequencing, in which the same gene or genetic locus is sequenced from a plurality of individuals, differences in the sequence identifying polymorphisms that exist in the sequenced population. Of these, some SNPs will be demonstrated to be associated with significant phenotypes, such as predisposition, presence, or progressive potential of disease.

Another application whereby parallel processing using capillaries in cassettes will prove useful is the confirmation of the sequence of DNA, often PCR products, intended to be spotted on to a substrate to create a microarray. Such microarrays are finding increased use in basic and applied research and are typically comprised of a rectangular array of spots of DNA on a glass slide, with a different, known DNA sequence at each spot. The experimenter then takes a labeled sample, either RNA or DNA and detects hybridization events between the labeled nucleic acid and the DNA spotted to the array. In this way, the experimenter can infer the identity and/or partial or complete sequence of the labeled nucleic acid.

To ensure the integrity of the data generated sing microarrays, it is necessary that the identity of the sequence of the spotted DNA be known with high confidence. Rearraying and other sample handling procedures introduce formatting errors that must be detected. Furthermore, PCR is often used to generate the DNA to be spotted. As is well known in the art, Taq and other thermostable polymerases introduce a certain number of erroneous base pairs per thousand as it amplifies the template. If errors have been introduced, they must be detected, and the amplified product discarded. Usually, this requires numerous processing steps separate from those associated with spotting the PCR product. However, use of an embodiment of the present invention greatly increases the efficiency of sequence determination and confirmation.

The DNA sample to be spotted is usually dissolved at a predetermined concentration in a solution comprising chaotropic ions, for example sodium thiocyanate. The DNA is so dissolved because it is to be immobilized to the surface of the glass microarray slide in a manner similar to that by which nucleic acid is immobilized inside capillary tubes. Typically the different DNA-chaotrope solutions are aliquoted into wells of 384-well capacity microtiter dishes for storage until ready to be spotted onto a microarray. Prior to spotting the dish is picked up by a robot associated with a automated spotting system and manipulated into a position whereby the spotting styli or pens can be dipped into multiple wells, usually 12, at one time.

The present invention can be adapted to sample and sequence the DNA in multiple wells of the same 384-well dish used as the DNA source for the spotting pens. It will be apparent that it can also be adapted to sample from dishes with more than 384 wells. Because the DNA to be sequenced is from the same sample to be spotted, numerous processing steps associated with sequencing the DNA from different samples are obviated. This results in substantial savings of time and material costs. According to this embodiment of the present invention, glass capillaries are arranged into a cassette in the same pattern and inter-capillary dimensions as that of the wells in one or more rows or columns of the dish. For maximal capacity, a total of 384 capillaries are arranged into a pattern with dimensions identical to that of the dish itself. Prior to spotting, the capillary cassette is filled with DNA-chaotrope solution (usually sodium thiocyanate) according to the methods of the present invention. After the DNA samples are immobilized and processed, they are sequenced. If any of the templates fails to give the correct sequence, the operator of the spotting apparatus knows not to spot that DNA, or if spotted, that data associated with hybridization at the corresponding spot is to an unwanted sequence and should be removed from the resulting data set.

Alternative Biochemical Reactions With Reversibly Immobilized Nucleic Acids

The present reaction mixture assembly may be used for assembly of numerous types of reactions. The same basic method used to assemble the PCR reaction mixture may be adapted to assembly of a cycle sequencing mixture, rolling circle amplification reaction mixture, enzymatic assays, chemical reactions, or other reaction mixtures.

Dispensing a Predetermined Quantity of a Nucleic Acid

As will be readily apparent, the experimenter is not obligated to carry out a reaction with the nucleic acid immobilized inside of a capillary tube. For a variety of reasons, it may be preferable to elute the immobilized nucleic acid from the inner surface of the capillary and either perform a reaction with it in a different reaction chamber, or to process the nucleic acid in some other way outside of the capillary. In such circumstances, it is possible to use the capillary as a pipettor to dispense a predetermined approximate mass of the nucleic acid in a fixed volume of liquid, and therefore at a predetermined approximate concentration, onto a substrate of the experimenter's choosing. To do so, the capillary is filled with elution fluid that elutes essentially all the reversibly immobilized nucleic acid. Thereafter, the solution of the elution fluid and nucleic acid is dispensed, usually onto or into a substrate. The substrate onto which the reaction mixture is transferred may be the wells of a multiwell microtiter plate, locations on a planar substrate, or wells that lead into an analytical chip. The reaction may also be dispensed into a solution for further chemical or biochemical reaction.

If multiple capillaries are arranged into a cassette, as described above, the cassette becomes a multichannel parallel pipettor, and it becomes possible to dispense a large number of normalized nucleic acid samples simultaneously. The dispensing can be into microtiter wells, microchips, and other chambers for further reactions. In addition, the nucleic acid can be dispensed directly into the reservoirs of a capillary array electrophoresis microchip or onto a MALDI or SELDI target, or onto or into a substrate adapted to be used in other analytical modalities.

Different methods may be used to expel or dispense liquid from capillary tubes. As will be appreciated by the skilled artisan, these methods can be employed to dispense not just an eluted nucleic acid solution, but also for removing the liquid from a filled capillary regardless of purpose, such as to remove reaction product after a reaction, or to remove washing solutions.

One method to dispense the contents of a single capillary tube or multiple similar capillaries arranged into a cassette format uses a centrifuge to dispense the fluid by centrifugal force. The centrifugal force is applied evenly to all of the capillaries in the capillary cassette such that capillaries independently dispense their contents onto a substrate situated below the orifice to the capillary from which fluid is expelled. If the substrate is a well of a microtiter dish, the dispensed liquid will be drawn by centrifugal force to the bottom of the wells. The design for a centrifuge and associated rotor and buckets to hold a cassette is disclosed in the copending application U.S. Ser. No. 09/577,199, herein incorporated by reference in its entirety.

A second method of dispensing the liquid contained in a capillary tube is through the use of an air displacement device. The design for an air displacement device designed to dispense the liquid contents of multiple capillaries arranged into a cassette is disclosed in the copending application U.S. Ser. No. 09/577,199, herein incorporated by reference in its entirety.

Alternatively, the contents of a capillary could be dispensed directly into a well, or sample port (FIG. 3E 76) of an analytical device (FIG. 3E 70), such as an electrophoresis chip. As shown in FIG. 3E, such an analytical chip would have an array of analytical lanes 78 in fluid communication with their respective sample inlets or ports 76. Multiple capillaries may be arranged into a cassette format such that the spacing of the capillaries matches the spacing of the sample inlets 76 in the chip. For example, a capillary cassette having 16 capillaries in two parallel rows of eight may dock with 16 wells in an analytical chip.

As an example, the capillary cassette illustrated in FIG. 3C includes capillaries 12 extending through flexible strip 11. Flexible strip 11 may be used alone or in combination with other such strips. The orientation of the capillaries in an essentially straight line may be altered by bending strip 11 to form an arc. FIG. 3D illustrates strip 11 bent to allow capillaries 12 to mate with input ports that are disposed on a substrate in a circular pattern. The liquid in capillaries 12 may then be electrokinetically injected or otherwise dispensed from capillaries 12 into ports 76 of an analytical chip 70 if an appropriate electrode array or other dispensing methods are used. Strip 11 may be positioned in the curved orientation by pressing strip 11 against a curved form, such as a curved metal block. This may be done by an automated strip mover incorporated into an automated sample preparation system.

The capillary cassette could be dispensed by air displacement or other dispensing means preferably selected to minimize splattering and bubble formation. Prior to dispensing the prepared reaction mixture into the wells 76 for analysis, a small amount of a diluent could be added to each analytical microchip well 76. When the capillary cassette is dispensed, the diluent will dilute the samples in the sample wells 76. The submicroliter volume reaction mixtures prepared in the capillary cassette, such as a DNA sequencing reaction product mixture, can readily be integrated with the analytical chip for sequencing or other analysis methods.

The elution fluid is preferably an aqueous solution of low ionic strength, more preferably water or a low ionic strength buffer at about a pH at which the nucleic acid material is stable and substantially intact, usually between pH 6.5 and 8.5. TE Buffer at 1×concentration (10 mM Tris-HCl, 1 mM ethylenediaminetetraacetic acid (EDTA), pH 8.0) and distilled or deionized water are particularly preferred elution solutions for use in the present invention. The low ionic strength of the preferred forms of the elution solution described above will tend to disrupt the salt-bridges established between the nucleic acid and the material comprising the inner surface of the capillary, ensuring that the nucleic acid is eluted into the solution. Other elution solutions suitable for use in the methods of this invention will be readily apparent to one skilled in this art.

According to the methods of the present invention, nucleic acid binding to the inner surface of he glass capillary tube is saturable. Under appropriate conditions, it is possible to control, with a high degree of accuracy, the quantity of nucleic acid immobilized inside any particular capillary. Thus, if the nucleic acid is eluted into an aqueous solution and dispensed, the concentration of the nucleic acid in the solution can be known, as well as the total quantity of nucleic acid in any particular volume of that solution. For example, if a capillary's binding capacity is 10 ng DNA, and this is eluted into 500 nl of elution fluid, the concentration of the solution is 0.02 grams per liter, with the molar concentration dependent on the molecular mass of the DNA molecules. If all 500 nl is dispensed, that droplet contains 10 ng DNA.

As will be understood by the skilled artisan, due to small variations among different capillary tubes, the amount of nucleic acid that can be immobilized and eluted, although highly consistent, is not identical between capillary tubes, or even between repeated use of the same tube. For this reason, the predetermined quantity or mass of nucleic acid eluted into the elution fluid is an approximate quantity or mass. Preferably, in this context, predetermined approximate mass shall mean that between similar capillaries, or repeated use of the same capillary, all other conditions being equal, the error between the mass expected to be immobilized or dispensed and actually immobilized or dispensed is not greater than 10%, more preferably 5%, more preferably 2%, and most preferably not more than 1% error.

Usually, the dispensing function of the present invention will be utilized by immobilizing a saturating quantity of nucleic acid in a particular capillary and dispensing the entire volume. Thus, to control the quantity and concentration of dispensed nucleic acid, the experimenter will choose a capillary with a predetermined binding capacity and volume. However, as discussed above, the experimenter can empirically determine conditions under which a predetermined non-saturating quantity of immobilized nucleic acid is bound. Accordingly, using these conditions, a non-saturating predetermined quantity of nucleic acid can be immobilized and then eluted from a capillary, allowing the experimenter to dispense any given amount of nucleic acid at will.

Under both circumstances, where a capillary has reversibly bound a predetermined quantity of nonsaturating, or saturating nucleic acid, if the experimenter, using methods familiar to the skilled artisan, controls the amount of nucleic acid-elution fluid expelled from the capillary, then knowledge of that volume permits dispensing precise amounts of nucleic acid. For example, controlled amounts of the fluid can be expelled by mechanical pumping, or electrokinetic pumping.

The following examples illustrate uses of the methods of the present invention, and are representative of the many different types of biochemical or enzymatic reactions that can be effected with the disclosed methods. These reactions include 1) dye-primer DNA sequencing, 2) dye-terminator DNA sequencing, 3) PCR amplification, 4) PCR amplification, enzymatic purification, and DNA sequencing, and 5) a general enzymatic reaction. The following examples are offered by way of illustration and not by way of limitation.

EXAMPLE 1

Dye-primer DNA Sequencing Analyzed by Capillary Electrophoresis

The color-specific primers were based on the M13 −40 FWD primer (5'-FAM-GTTTTCCCAGT*CACGACG-3' (SEQ ID NO:1), with 5-carboxyfluorescein (FAM) as the donor dye, and a termination-specific fluor attached to the indicated thymine (T*) as the acceptor dye. The thymine was labeled with FAM for ddC-terminated reactions (C-FAM), 6-carboxyrhodamine for ddA reactions (A-REG), N,N,N',N'-tetramethyl-5-carboxyrhodamine for ddG reactions (G-TMR), and 5-carboxy-X-rhodamine for ddT reactions (T-ROX). A master mix for 100 dye-primer sequencing reactions was prepared by combining 65 $\mu$L reaction buffer (220 mM Tris-HCl, pH 9.5, 33.2 mM $MgCl_2$), 100 $\mu$L dye-primer solution (either 1 $\mu$M T-ROX, 1 $\mu$M G-TMR, 0.5 $\mu$M A-REG, or 0.5 $\mu$M C-FAM), 100 $\mu$L of the corresponding deoxy- and dideoxynucleotide mix (0.94 mM DATP, dCTP, dTTP, 7-deaza-dGTP, with 3.1 $\mu$M dideoxynucleotide), 10 $\mu$L of enzyme (32 units/pL ThermoSequenase), and 225 $\mu$L filtered demonized water. This solution was aliquoted into a 96-well reagent plate prior to mixing with template DNA. The general mixing scheme required the use of two capillary cassettes and a 384-well "mix plate." The first capillary cassette (transfer cassette) was dipped in a solution of template DNA (20 ng/$\mu$L M13mp18), and then inverted onto the top of a 384-well "mix plate" with the short ends of the capillaries inserted into the wells. The inverted transfer cassette and mix plate were placed inside a bench top centrifuge. A balance plate was added to balance the rotor and the centrifuge brought to 3,000 ×g for 5 seconds. The centrifugation uniformly dispensed the contents of the transfer cassette into individual wells of the 384-well plate. After the centrifuge step, the transfer cassette was transferred to the capillary cassette washer 410 for cleaning, and the mix plate was used for a subsequent centrifuge step for reagent addition.

To add reagents, a second capillary cassette (the reaction cassette), was dipped into the wells containing sequencing reagents (prepared as described in the preceding paragraph) and inverted over the same wells of the same 384-well plate. The reaction cassette and mix plate were placed in the centrifuge, spun at 3,000×g for 5 seconds, and removed from the centrifuge. At this point each well contained 500 nL of template DNA and 500 nL of sequencing reagents to form the final reaction mixture. The second capillary cassette (used to add reagents) was then dipped into the 1 µL mixture contained in the mix plate, filling the capillaries of the reaction cassette with 500 nL.

The capillary cassette was inserted into the internal chamber of an air-based thermal cycler, as described herein in FIGS. 7A–C, where the ends of the capillary segments are sealed by depressing the ends of the capillaries against deformable membranes 264a and 264b. After 30 cycles of 95° C. for 2 seconds, 55° C. for 2 second, and 72° C. for 60 seconds, the thermal cycler was opened, removing the ends of the capillaries from contact with the deformable membranes. The capillary cassette was removed and placed on top of a 96-well "pooling plate" with the short ends of the capillaries inserted into the wells. The capillary cassette and mix plate were placed into a centrifuge, with a balance plate. The reaction products were dispensed by centrifugal force (~2500×g) into a microtiter plate containing 40 µL of 80% isopropyl alcohol. After an initial reaction, the capillaries were washed as described herein. After the four dye-primer reactions had been performed in four individual capillary cassettes and the four sets products pooled into the wells of the 96 well pooling microtiter plate, the samples were subsequently centrifuged at 3000×g for 30 minutes. The alcohol was decanted by a gentle inverted spin, and the samples were resuspended in 5 µL of ddH$_2$O for electrokinetic injection and analysis by MegaBACE™ capillary array electrophoresis.

Analysis of the DNA sequencing fragments was performed with MegaBACE™, a 96-capillary array electrophoresis instrument (Molecular Dynamics, Sunnyvale, Calif.) using scanning confocal laser-induced fluorescence detection. Separations were performed in 62 cm long, 75 um I.D., 200 µm O.D. fused-silica capillaries with a working separation distance of 40 cm. Electroosmotic flow was reduced by Grignard coupling of a vinyl group to the capillary surface and acrylamide polymerization. The capillaries were filled with a fresh solution of 3% linear polyacrylamide (LPA) (MegaBACE™ Long Read Matrix, Amersham Life Sciences, Piscataway, N.J.) which was pumped through the capillaries under high pressure from the anode chamber to individual wells of a 96-well buffer plate contained in the cathode chamber. Each well was filled with 100 µL of Tris-TAPS running buffer (30 mM Tris, 100 mM TAPS, 1 mM EDTA, pH 8.0). The matrix was equilibrated for 20 minutes followed by pre-electrophoresis for 5 minutes at 180 V/cm. Prior to sample injection, the cathode capillary ends and electrodes were rinsed with double distilled water (ddH$_2$O) to remove residual LPA prior to sample injection.

DNA sequencing samples were electrokinetically injected at constant voltage from a 96-well microtiter plate according to the specified conditions; one preferred injection condition for 500 nL samples is 40 seconds of injection at an applied voltage of 2 kV. After injection, the capillary ends were rinsed with water, the buffer plate was placed in the cathode chamber, and the electrophoresis run was commenced. Separations were typically for 120 minutes at 8 kV. Computer controlled automation of the instrument and data collection was performed using LabBench software (Molecular Dynamics, Sunnyvale, Calif.). Specific injection and run conditions were tailored to the reaction mixture to be analyzed.

The reproducibility of the described method for sub-microliter dye-primer cycle sequencing is shown in FIG. 9. This histogram shows the percent of samples in different read length bins and shows that the method is highly reproducible. Over 80 percent of the sequenced DNA inserts had read lengths over 600 bases. Overall, this plate of 96 samples yielded 55,000 high quality "Phred 20" bases, with an average read length of 605 bases.

EXAMPLE 2

Dye-primer DNA Sequencing Analyzed by a Capillary Electrophoresis Microchip

In another analysis example, dye-primer reactions performed in the same capillary cassette were analyzed by direct injection into a 16 channel microfabricated "chip-based" analyzer described in detail in S. Liu, H. Ren, Q. Gao, D. J. Roach, R. T. Loder Jr., T. M. Armstrong, Q. Mao, I. Blaga, D. L. Barker, and S. B. Jovanovich, Proc. Natl. Acad, Sci. USA, 5-00. The 16-channel chip is formed by bonding two glass wafers, the top wafer has 50 um deep by 100 um wide channels etched into it by standard microfabrication methods. The pattern etched has a combination of two 8-channel groups, each with a common anode reservoir Sixteen cathode reservoirs were evenly spaced at 4.5-mm intervals in a line, as were sixteen sample and sixteen waste reservoirs. The reservoirs were formed by the drilled access holes through the top etched wafer. Sixteen 250-µm long twin-T injectors were formed by the offset of channels from the sample and waste reservoirs joining the main separation channel. The distance between adjacent channels (center-to-center) was 600 µm in the detection region. The two alignment holes were used to align the chip to the detector.

In this example, a dye-primer reaction terminated by ddT was performed as described and dispensed into the sample wells of a microchip containing 1.5 µL of ddH$_2$O. Sample injection was performed by applying voltages of 50 and 10 volts respectively to the waste and cathode reservoirs, typically for 60 s, while the sample and anode reservoirs were grounded. Separations were carried out immediately after sample injection by applying 2,000 volts to the anode reservoir, 140 volts to sample and waste reservoirs, while grounding the cathode reservoir. The corresponding separation field strength was ca. 227 V/cm. The laser-induced fluorescence was collected, digitized, and processed into the electropherogram shown in FIG. 10. The electropherogram demonstrates microchip analysis of the reactions performed in the described capillary cassette system.

EXAMPLE 3

Dye-terminator Cycle Sequencing with Alcohol Precipitation Purification

Dye-terminator cycle sequencing was demonstrated using the capillary cassette system and alcohol precipitation for cleanup prior to capillary array electrophoresis. In this example, the sequencing reaction mix was prepared by mixing 400 µL of sequencing reagents (Dynamic ET terminator kit, Amersham Pharmacia Biotech, Part 81600) with 100 µL of 5 pmol/µL of M13 –21 FWD primer (5'-TGT AAA ACG ACG GCC AGT-3' (SEQ ID NO:2)). The reaction mix was distributed in 5 µL aliquots to a 96-well "reagent" plate. Mixing of template DNA and sequencing reagents was performed in the same series of steps described in Example 1, using a transfer cassette was used to transfer 500 nL of DNA samples and a reaction cassette to transfer 500 nL of sequencing reagents from the reagent plate to the wells of the mix plate. This same reaction cassette was then filled by capillary action with the template/reagent mixture.

The capillary cassette was transferred to the air-based thermal cycler where the capillaries were sealed between the deformable membranes within the thermal cycler. Thermal cycling was achieved with 30 cycles of 95° C. for 2 seconds, 55° C. for 2 seconds, and 60° C. for 60 seconds. After the thermal cycling, the cassette was removed from the cycling chamber and the contents of the capillaries dispensed by centrifugal force (3000×g) into a 96-well plate containing 40 µL of 80% ethanol. The samples were centrifuged at 3000×g for 30 minutes. The alcohol was decanted by a gentle inverted spin, and the samples were resuspended in 5 µL of ddH$_2$O for electrokinetic injection and analysis by MegaBACE™ capillary array electrophoresis. The cleanup of dye-terminator reactions by alcohol precipitation, the reproducibility of the technique, and the application to "real-world" templates is represented as a histogram of percent success versus read length in FIG. 11. FIG. 11 demonstrates excellent read lengths and success rates with M13 subclone inserts prepared from a subclone library of a mouse bacterial artificial chromosome.

EXAMPLE 4

Dye-terminator Cycle Sequencing with Size-exclusion Purification

In another example, dye-terminator reactions were performed in 500 nL capillaries as described in Example 3, and the reaction products dispensed into 15 µL of ddH$_2$O by centrifugal force. The 15 µL samples were transferred to a filter plate containing 45 µL of hydrated Sephadex G-50. The samples were centrifuged through the Sephadex matrix at 910×g for 5 minutes and the fluent collected in a clean 96-well injection plate. The samples were electrokinetically injected without further dehydration or processing into MegaBACE™. For 16 samples, an average read length of 650 bases was obtained demonstrating the compatibility of sub-microliter dye-terminator sequencing with size-exclusion purification.

EXAMPLE 5

Pcr Amplification of Plasmid Insert DNA

The present technology uses the disclosed system for the PCR amplification of insert DNA (e.g. subclone inserts from a DNA library). The PCR reaction mixture was prepared by mixing 5 µL of 10 µM of M13 –40 FWD primer (5' GTT TTC CCA GTC ACG AC 3' (SEQ ID NO:3)) and 5 µL of 10 µM –40 REV primer (5' GGA TAA CAA TTT CAC ACA GG 3' (SEQ ID NO:4)) with 25 µL of 10×GeneAmp buffer, 15 µL of 25 mM MgCl$_2$, 5 µL of AmpliTaq Gold, 2.5 µL of 1 mg/mL bovine serum albumin (BSA), and 67.5 µL of ddH$_2$O. This mix was aliquoted in equal volumes to sixteen 0.20 mL tubes.

The reaction was initiated by mixing template DNA with the PCR cocktail using the two-capillary cassette and mix-plate method described. The transfer cassette was dipped into the glycerol stock solutions of a subclone library and dispensed by centrifugal force into the wells of a 384-well plate. A second "reaction" cassette was used to transfer 500 nL of PCR cocktail to the same wells by centrifugal force.

The capillaries of the reaction cassette were subsequently dipped into the combined mixture of template DNA and PCR reagents, filling the capillaries by capillary action. Amplification was effected by placing the capillaries into the cycling chamber and thermally cycling with an activation step of 95° C. for 12 minutes followed by 30 cycles of 64° C. for 4.5 minutes and 95° C. for 5 seconds.

The PCR products were analyzed by agarose gel electrophoresis and compared with the same subclones amplified by full volume (25 µL) reactions performed in 0.20 mL tubes. Nanoscale capillary cassette samples were dispensed into 4.5 µL of ddH$_2$O by centrifugal force. Equivalent volume aliquots of full volume reactions were transferred manually using a low volume pipettor. To each 5 µL sample, 1 µL of 6×loading dye was added and the sample quantitatively transferred to the wells of an agarose gel. Agarose gel electrophoresis was performed using a 0.7% agarose gel with 1×Tris-acetate-EDTA buffer, pH 8.0. Samples were separated for 40 minutes at 15 V/cm, stained with Sybr Green II (Molecular Probes, Eugene, Oreg.), and imaged using a two-dimensional fluorescence scanner (FluorImager, Molecular Dynamics, Sunnyvale, Calif.). The scanned gel image is shown in FIGS. 12A and 12B. It can be seen that samples prepared at full volume (FIG. 12A) and 500 nL volume (FIG. 12B) have the same molecular weight distribution. This example demonstrates nanoscale sample preparation can be used for PCR reactions and that the products can be analyzed by traditional macro-scale analysis methods such as agarose gel electrophoresis.

EXAMPLE 6

PCR Amplification and Cycle-Sequencing

A preferred mode of preparing cycle sequencing samples using the present invention is to prepare nanoscale PCR samples in the capillary cassette and related instrumentation, perform macroscale ExoI/SAP reactions, and then perform the cycle sequencing in the capillary cassette and related instrumentation. Nanoscale PCR template preparation for DNA sequencing was demonstrated by performing PCR amplification from glycerol stock subclones. Glycerol stock subclones were PCR amplified in the capillary cassette and related hardware as described in Example 5. After PCR amplification, the contents of the capillaries were dispensed by centrifugation into the wells of a 96-well plate containing 4.5 µL of 7.5 mU of shrimp alkaline phosphatase (SAP) and 37.5 mU of exonuclease I (ExoI). The PCR products and ExoI/SAP solution were allowed to incubate at 37° C. for 5 minutes to digest the unincorporated primers and to dephosphorylate the unincorporated nucleotides. After an initial incubation, the enzymes were deactivated by heating the solution to 72° C. for 15 minutes.

The ExoI/SAP treated PCR products were aliquoted to a fresh 384-well mix plate with a transfer capillary cassette and centrifugal dispensing. An equal aliquot of dye-terminator sequencing reagents were added to the 500 nL of purified PCR products using another capillary cassette, the reaction cassette, and centrifugal dispensing. The capillaries of the reaction cassette were then filled by dipping the capillary cassette into the 1 µL reaction mixture. The template was amplified according to Example 3, dispensed into 40 µL of 80% ethanol and purified as described. Analysis of the sequencing reactions was performed by MegaBACE™ using electrokinetic injection. Portions of six base called sequencing electropherograms from subclone templates prepared by nanoscale PCR amplification from glycerol stock solutions and by nanoscale cycle sequencing are shown in FIG. 13. By performing PCR in a capillary cassette and subsequently transferring the reaction mixture to a microplate, the present system allows a simplified transition from nanoscale (less than 1 μL volumes) to greater than nanoscale reaction volumes. The present system also allows a simplified transition from macroscale (more than 1 μL volumes) to nanoscale reaction volumes, as shown by utilizing the Exo I/SAP reactions for cycle sequencing in the capillary cassette.

EXAMPLE 7

Isothermal Enzyme Performed in Sub-microliter Capillary Cassette

The use of the described system for performing enzyme reactions was demonstrated with a fluorogenic enzymatic assay of β-galactosidase hydrolysis of βP-D-β-galactosidase to the fluorophore resorufin. The β-galactosidase catalyzed hydrolysis of resorufin-β-D-galactosidase (RBG) was performed within the capillaries of a 96-capillary cassette and in control full volume reactions in which β-Gal hydrolyzes RBG.

A stock solution of 35 μM RBG was prepared in 5 mL of buffer (100 mM Tris-HCL, 20 mM KCl, and 2 mM $MgCl_2$) to 5 mg of RBG, vortexing vigorously, and filtering the solution through a 0.40 micron filter and then adding an equal volume of buffer. A dilution curve of RBG was then prepared from the stock solution. To each 10 μL of RBG solution prepared in 0.20 mL tubes, 200 ug of β-galactosidase was added and after briefly mixing, filled into a capillary cassette by capillary action. The cassette was placed in air cycler and after 2 minutes at 37° C., the capillary cassette was removed and the contents centrifuged out of the capillaries into a 384-well scan plate containing 5 μL of 1 M sodium carbonate. The wells of the scan plate were subsequently filled with 50 μL of $ddH_2O$. In parallel, the 0.2 mL tubes were incubated at 37° C. for 2 minutes and the ful volume reactions stopped by adding 1 M sodium carbonate. A control aliquot from the enzyme reactions performed in the 0.20 mL tubes was added to the scan plate.

Solid-phase capture of the β-galactosidase was also demonstrated with this system by simply filling the cassette with a 20 μg/mL solution of β-galactosidase to bind to the capillary surface followed by removing the excess liquid and drying the cassette using the described cassette wash-manifold. After β-galactosidase binding the capillaries were filled with RBG solution by capillary action. The reaction was performed for 2 minutes at 37° C. and analyzed by dispensing into 1 M sodium carbonate, and diluting with water in the scan plate.

Once all three sets of reactions (full volume, capillary cassette, and capillary cassette with solid phase capture) had been added to the scan plate, the plate was read by a fluorescent plate reader (Typhoon, Molecular Dynamics, Sunnyvale, Calif.). The results of the standard curve performed in 0.2 mL tubes (tube rxn), a reaction performed in the capillary cassette without solid phase capture (capillary reaction), and in the capillary cassette with solid phase capture (capillary with binding reaction) are summaries in FIG. 14. FIG. 14 shows the expected signal versus substrate concentration for the tube reactions, and data points of signal for the pre-mixed enzyme reaction performed in the capillary cassette, and for the capillary-binding β-galactosidase assay.

This example serves to illustrate the compatibility of the described system for performing a range of general enzyme activity and inhibition assays. In addition, it demonstrates that solid phase capture can be applied to proteins and enzymes as well as DNA. Finally, it shows the described system can be applied to isothermal reactions.

EXAMPLE 8

Template purification

This example demonstrates the effectiveness with which the methods of the instant invention can be used to purify template DNA of contaminants that interfere with sequencing reactions and acquisition of high quality sequence data.

Figure 17A:
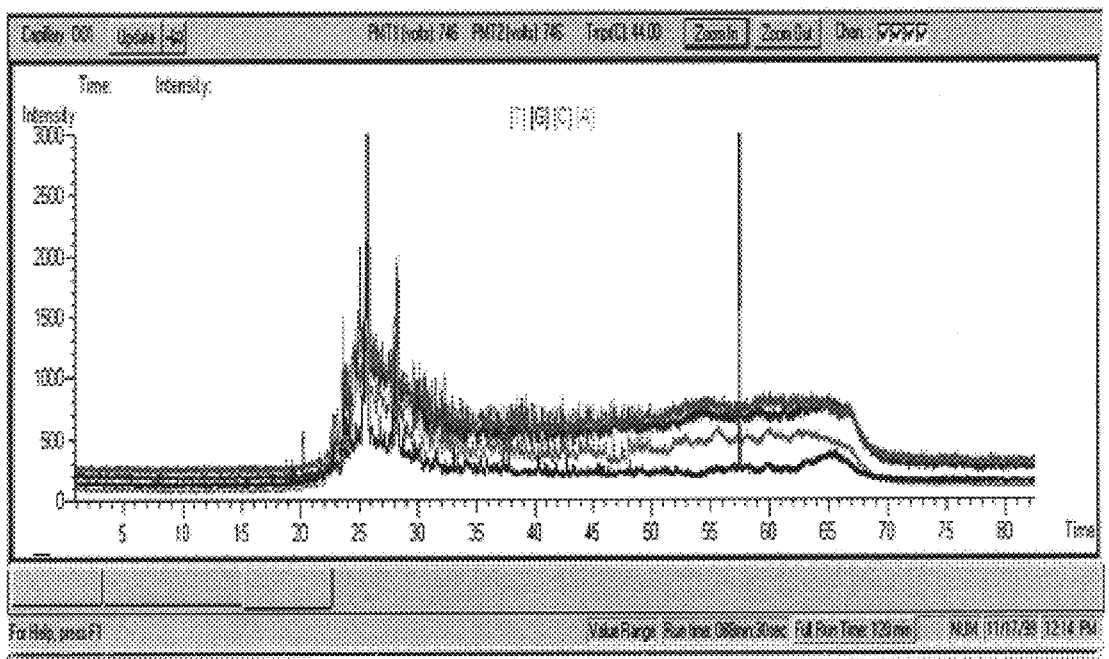
FIG. 17A shows the results of sequencing PCR products mixed with the reaction mixture prior to sequencing.
Figure 17B:
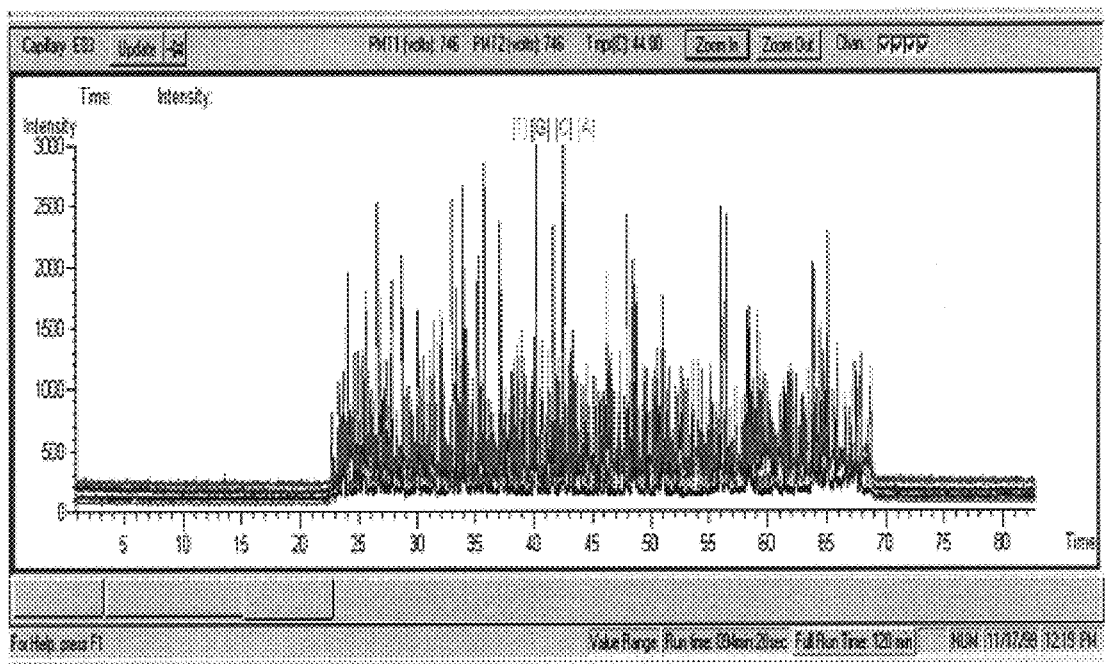
FIG. 17B shows the results of first mixing the PCR template with sodium thiocyanate, binding the DNA to the inner surface of the capillary, washing the DNA with 80% ethanol, followed by sequencing.

Template capture cleanup of PCR products as DNA sequencing template using direct reversible binding to the inner surface of a fused-silica capillary tube. A 500 nl volume sequence reaction, using the ET dye-terminator cycle sequencing method was carried out in a 150 μm inner diameter capillary tube and analyzed on MegaBACE™ using a 2 kV, 30s injection. FIG. 17A shows the results of sequencing PCR products mixed with the reaction mixture prior to sequencing. FIG. 17B shows the results of first mixing the PCR template with sodium thiocyanate, binding the DNA to the inner surface of the capillary, washing the DNA with 80% ethanol, followed by sequencing.

Nucleic Acid Normalization Examples

The following examples demonstrate the usefulness and effectiveness of the methods of the present invention for normalizing the quantity of nucleic acid directly and reversibly immobilized inside capillary tubes.

EXAMPLE 9

Template Normalization Effect for M13, Plasmid, and PCR Product DNA

Figure 18:
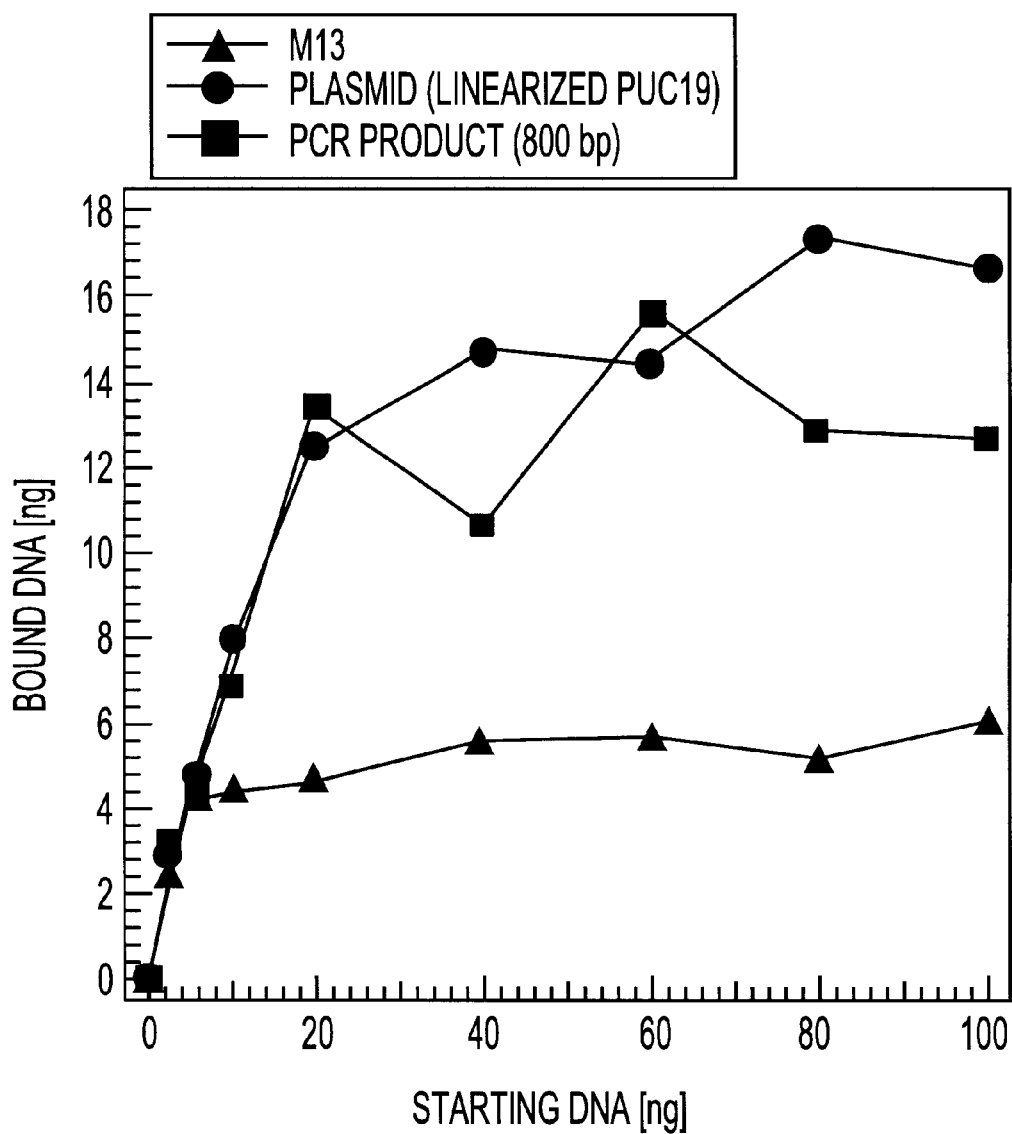
FIG. 18 represents the retained mass of DNA following a template capture protocol.

FIG. 18 represents the retained mass of DNA following a template capture protocol. The amount of DNA bound remains constant above 40 ng starting template for M13 (▼), plasmid (●), and PCR product (■).

Template DNA was prepared by a restriction digest of M13mp18 and PUC19 DNA to form linear single and linear double stranded DNA respectively. These templates, along with a 800 bp PCR product (standard amplification conditions) were end labeled with $^{32}p$ using [γ-32P]ATP and T4 polynucleotide kinase. The labeled DNA was seeded into unlabeled template of the same type and a calibration curve was generated for the seeded DNA solution. Template binding was performed by mixing stock DNA with 10 M sodium thiocyanate and loading into 500 nl fused-silica capillaries. After 10 minute incubation and 80% ethanol washing, the capillaries were placed in scintillation fluid and quantified. FIG. 18 shows definitive normalization for three sources of template DNA.

EXAMPLE 10

Template Capture Normalization Effect on Read Length

Figure 19:
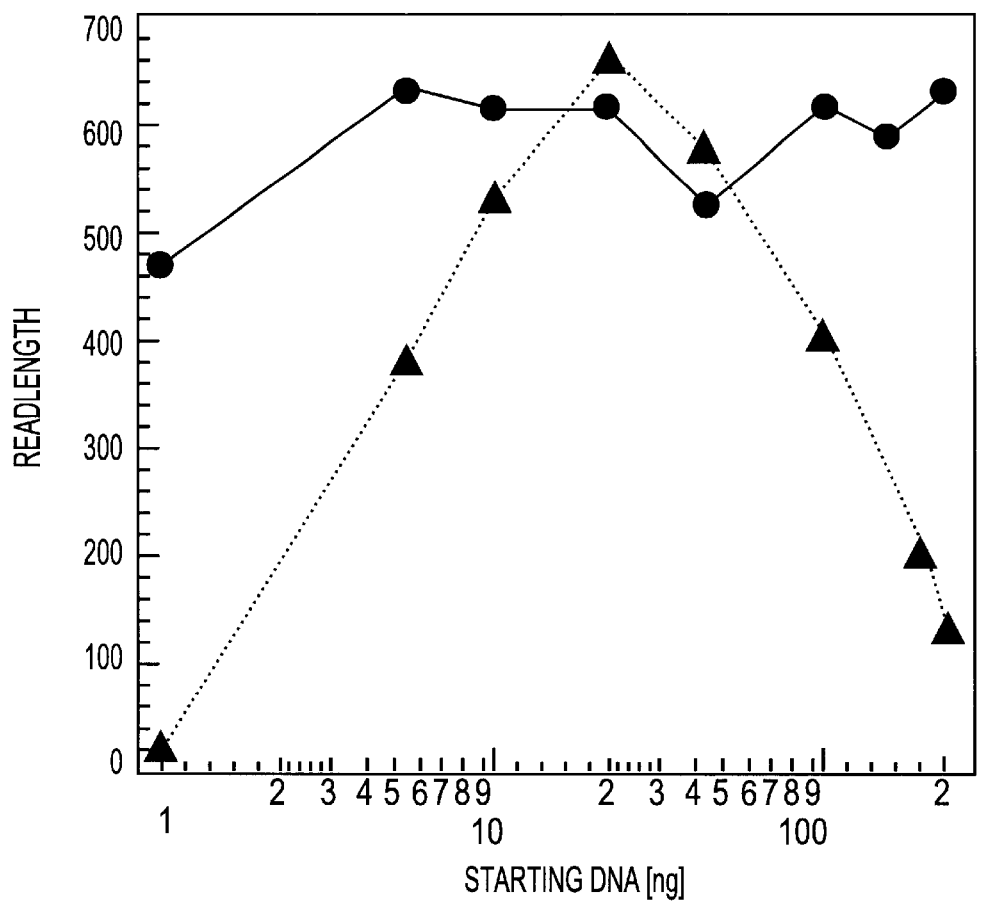
FIG. 19 shows a plot of read length versus starting DNA mass for samples prepared by premixing DNA and sequencing reagents (▼) compared to samples prepared by template capture (●)

FIG. 19 shows a plot of read length versus starting DNA mass for samples prepared by premixing DNA and sequencing reagents (▼) compared to samples prepared by template capture (○). The normalization effect is highlighted by a nearly constant read length obtained for the template capture samples, whereas for premixed samples, template overloading and reduction in read length occurs above 20 ng starting DNA.

Template binding was performed by mixing stock M13mp18 DNA with 10 M sodium thiocyanate and loading into 500 nL fused-silica capillaries. After 10 minute incubation and 80% ethanol washing, the capillaries were placed filled with ET terminator premixed with M13–40FWD sequencing primer. Premixed reagents were prepared in a 10 µl volume and loaded into clean sample preparation capillaries. The air-based cycle sequencing was performed as previously described followed by ethanol precipitation and MegaBACE™ analysis at 2 kV, 30 second injection, 8 kV, 120 minute run time.

EXAMPLE 11

Template Capture Polymerase Chain Reaction with Normalization

Figure 20:
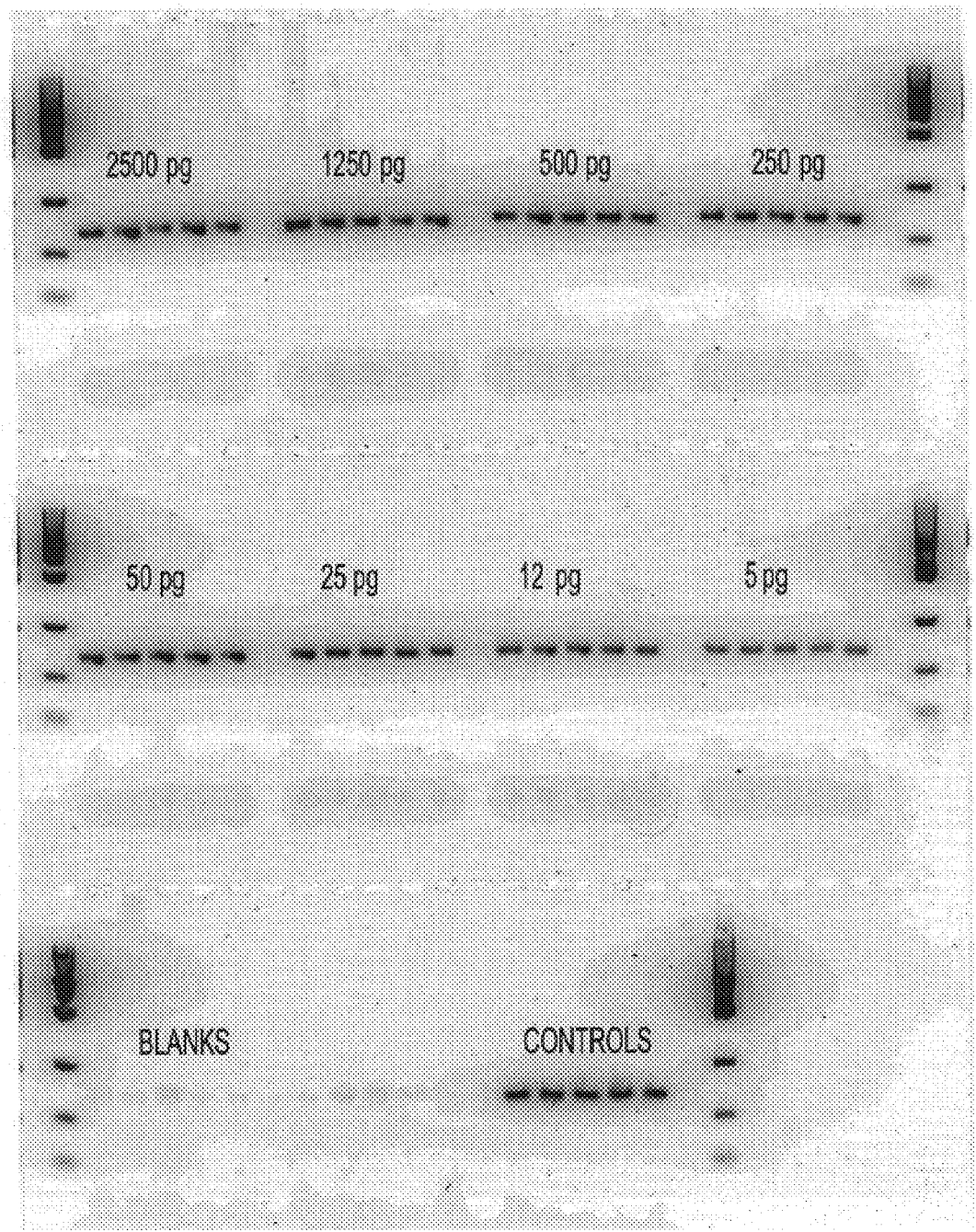
FIG. 20 shows products of PCR reactions after template binding of the indicated starting amount o M13mp18, electrophoresed through a 1.5% agarose gel, stained with SYBR Green dye and imaged with a Fluorimager apparatus.

PCR reactions were performed after template binding of indicated starting amount of M13mp18. Standard PCR amplification reactions with M13 –100 FWD and M13 –400 REV primers were performed in 500 nl capillary cassette with 10 s at 95° C., 10 s at 55° C., and 120 s at 72° C. Reaction products were dispensed by centrifuge into loading buffer, and transferred to a 1.5% agarose gel. The products were stained with SYBR Green dye and imaged with a Fluorimager apparatus, as shown in FIG. 20.

EXAMPLE 12

Figure 21:
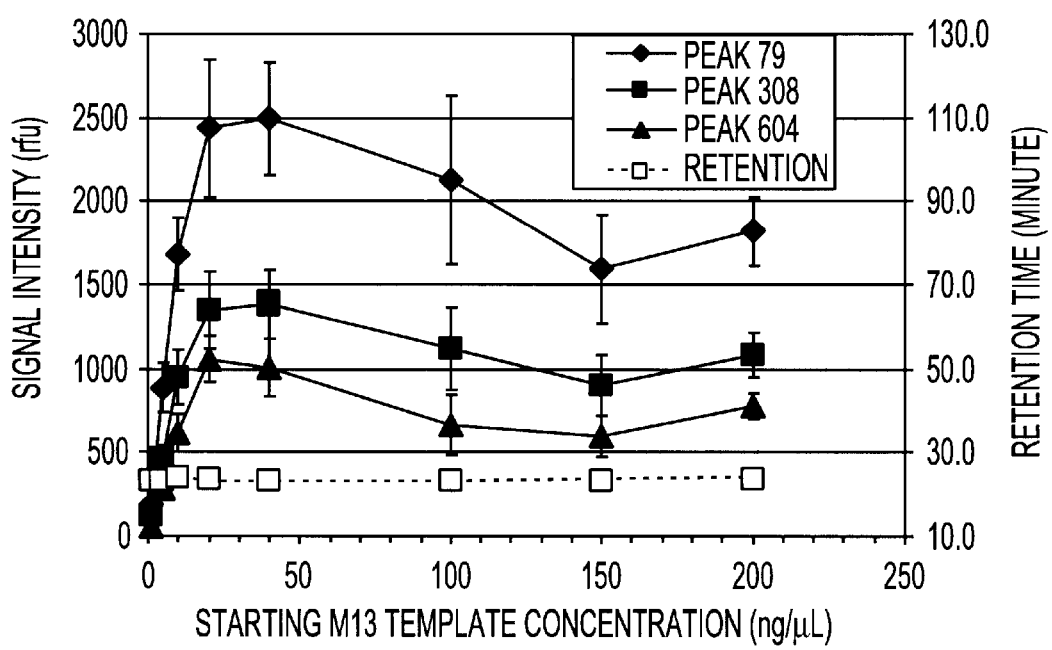
FIG. 21 represents the relative signal intensity obtained with increasing template concentration.

Template Capture Normalization Effect on Peak Height and Migration Time and Peak Height and Migration Time for Pre-mixed Samples Template capture normalization effect on peak height and migration time. FIG. 21 represents the relative signal intensity obtained with increasing template concentration represented by the intensity of peak 79, peak 308, and peak 604 (ddT-terminated peaks early, middle, and late in the electrophoresis chromatogram). The peak intensity increases to 40 ng/µl and levels off, confirming by peak height the normalization effect and saturation level of the template capture technique. The migration time of the first peak is relatively constant across template concentrations.

Figure 22:
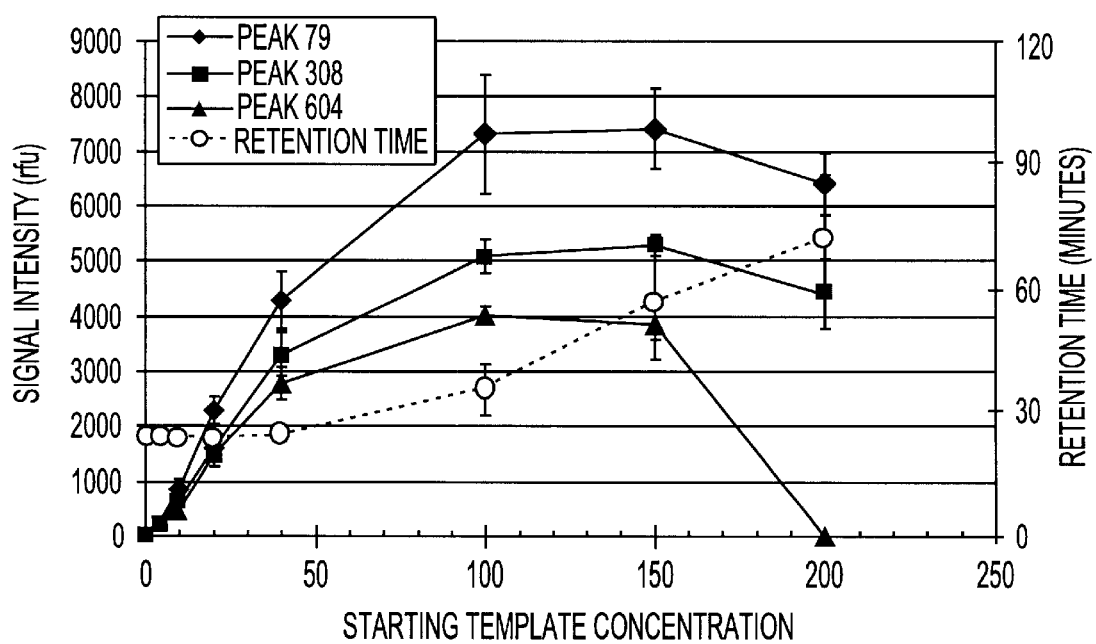
FIG. 22 represents the relative signal intensity obtained with increasing template concentration, showing peak height increasing with increasing template concentration.

Peak height and migration time for pre-mixed samples. FIG. 22 shows peak height increasing with increasing template concentration, reaching a maximum due to overloading of the sequencing sample. An excess of template DNA inhibited the electrokinetic injection, reducing the current in the sample run, consequently increasing the migration time of the sample through the capillary.

EXAMPLE 13

Nanoscale Direct Cycle Sequencing from Glycerol Stocks of Clone

Figure 23A:
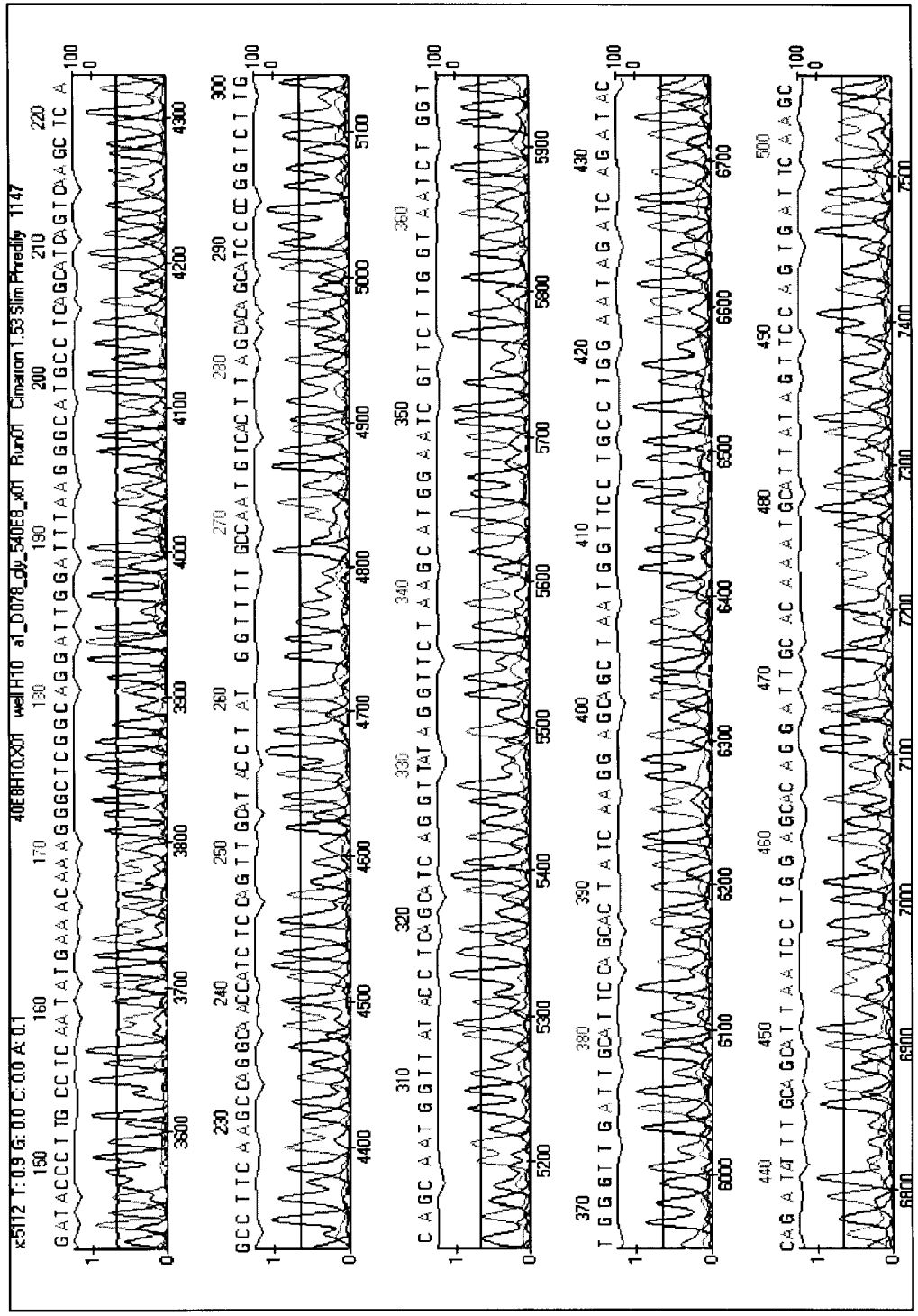
FIGS. 23A and 23B show a trace that had a Phred 20 score of 561 bases obtained by nanoscale direct cycle sequencing from glycerol stocks.
Figure 23B:
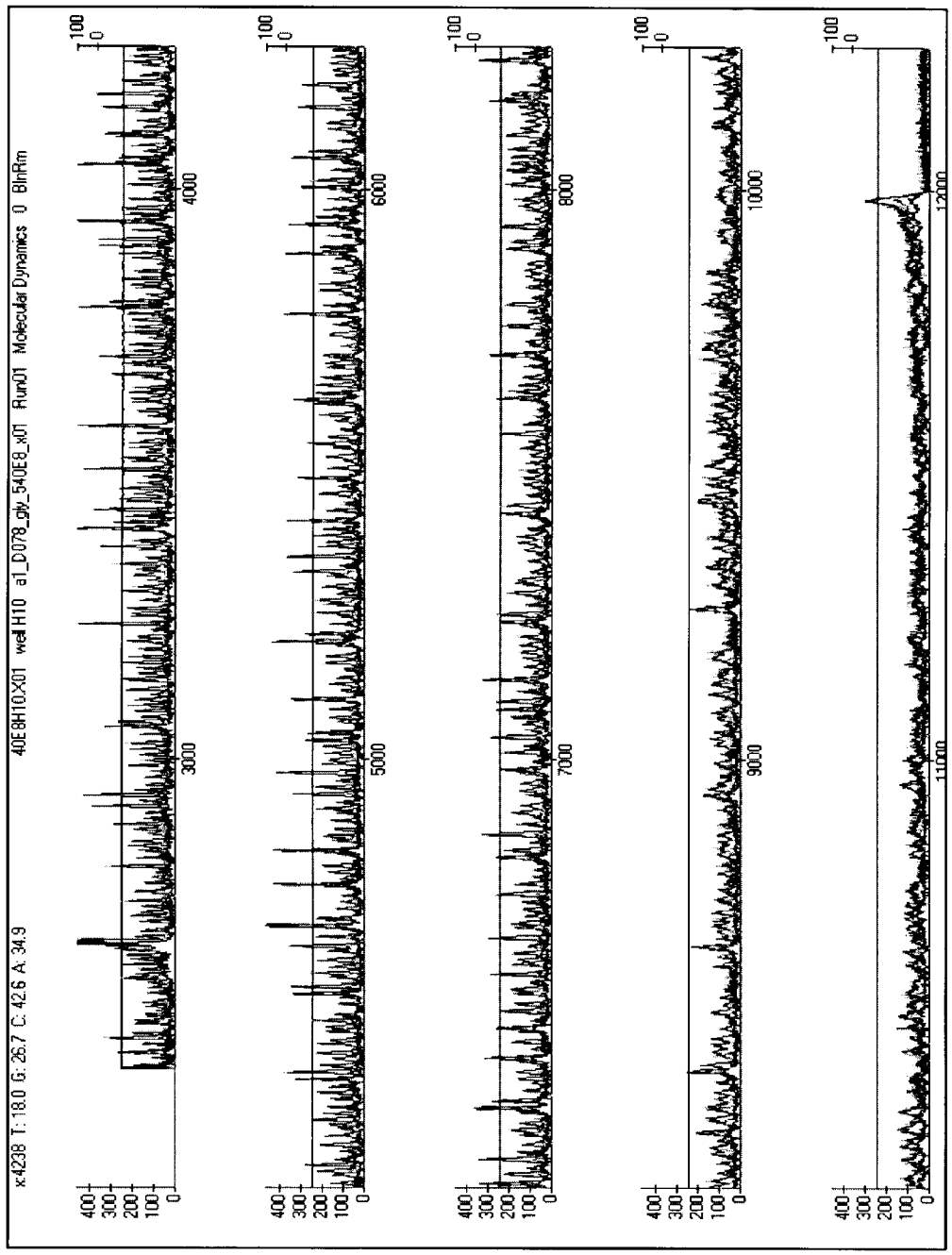

Sample preparation for DNA sequencing could be simplified if some of the many steps involved in preparing sequencing samples from cloned DNA in bacterial cells could be eliminated. Typically for capillary electrophoresis analysis, bacterial cells are grown and lysed, PCR amplification is performed, followed by ExoI/SAP cleanup and then cycle sequencing. The instant invention provides a method to simplify the workflow by cycle sequencing directly from glycerol stocks of clones. Equal volumes of glycerol stock and 10 M NaSCN were pulled into a 96 channel 500 nl capillary cassette. A five minute binding was performed at 60° C. in the air cycler disclosed in the copending application U.S. Ser. No. 09/577,199, herein incorporated by reference in its entirety. The capillary cassette was washed with an 80% ethanol rinse and dried with flowing nitrogen in the capillary cassette washer disclosed in the copending application U.S. Ser. No. 09/577,199. The cassette was then filled by capillary action with a 1:4:5 mixture of primer, ET terminator premix and water and cycled in the air cycler. The cycling protocol was for ET terminators as described in Example 1, above. The samples were ethanol precipitated by being dispensed by centrifugation (3220 g for 30 minutes at 4° C.) into a microtiter plate containing 80% ethanol. After decanting and 30 seconds of inverted spinning at 50 g to remove ethanol, the samples were resuspended in 5 ul water. The samples were then injected into MegaBACE™ with a 2 kV, 30 second injection followed by a 8 kV, 140 minute separation. The data were analyzed with Sequence Analyzer software (Molecular Dynamics) and then processed to determine Phred 20 base calling scores. FIGS. 23 A and B show a trace obtained by this method that had a Phred 20 score of 561 bases. This example demonstrates the application of the instant invention to direct sequencing from frozen glycerol stocks of bacteria. It will be apparent to the skilled artisan that this method can be applied to the sequencing of bacterial colonies grown on agar plates, or similar solid growth media, regardless whether the plates are fresh or desiccated.

EXAMPLE 14

Genotyping with Nanoscale Single Base Extensions of Nucleic Acids

The instant invention can be applied to perform nanoscale genotyping reactions.

Single-base extension (SBE) reactions were performed in the 96 channel capillary cassette. The single base extension analysis consists of the single base extension of a DNA primer that terminates immediately before the base to be interrogated. PCR reactions of 25 ul were prepared containing 5 ng/ul of genomic human DNA, 1 µM of forward and reverse primers, buffer, $MgCl_2$ and AmpliTaq Gold. The PCR cycling was 96° C. for 12 min, 35 cycles of 94° C. for 20 sec, 60° C. for 20 sec, and 72° C. for 30 sec, followed by 72° C. for 2 min. An Exo I/SAP cleanup was performed by adding 9 units of SAP and 45 units of Exo I to the 25 µl of PCR products. The reaction was incubated at 37° C. for 45 min and then the ExoI/SAP enzymes denatured by heating to 95° C. for 15 min.

For full volume control reactions, 9 µl of SBE premix containing fluorescently labeled dideoxyterminators, a DNA polymerase, buffer solution and 1 µl of 2 µM primer was added to 10 µl of the ExoI/SAP treated PCR products. For reactions in the 500 nl capillary cassette, samples were loaded by capillary action.

The single base extension reactions were performed by 25 cycles of 96° C. for 10 sec, 50° C. for 5 sec, 60° C. for 30 sec. The thermal cycling was carried out in either MJ Research tetrads (a type of thermal cycling machine) for the full volume controls, or for the capillary cassette samples, in the air cycler disclosed in the co-pending application U.S. Ser. No. 09/577,199, herein incorporated by reference in its entirety. The samples were dispensed into water and injected into MegaBACE™ for analysis.

Figure 24:
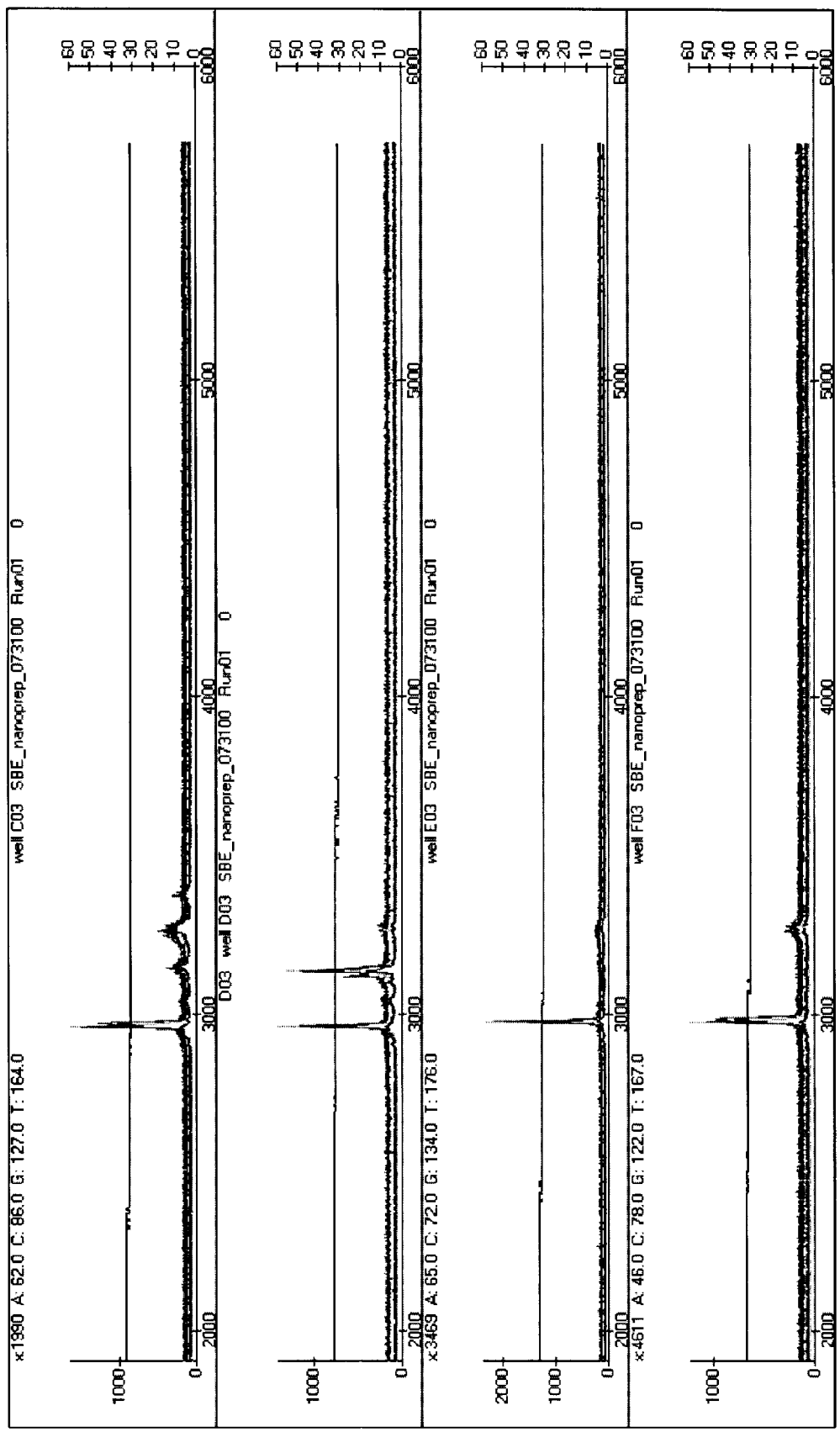
FIG. 24 are MegaBACE™ traces from four nanoscale single base extension reactions, without template capture, demonstrating heterozygosity in trace 2.

FIG. 24 demonstrates that the capillary-based reactions could correctly identify single nucleotide polymorphisms. Traces 1, 3, and 4 were obtained from samples homozygous at the interrogated base. Trace 2 was obtained from a sample heterozygous at the interrogated base and demonstrates that allelic polymorphism can be detected using nanoscale reactions. Signal is essentially the same as that obtained with the full volume reactions.

The entire process, from PCR to SBE, was accomplished using the capillary cassette.

Template capture in the capillary, as described in this application, is used in an improved version of this nanoscale single base extension reaction and provides even better results.

It will also be apparent to the skilled artisan that single base extension of messenger RNA using reverse transcriptase and fluorescently-labeled ribonucleotides permits genotyping using mRNA as an alternative to genomic DNA.

EXAMPLE 15

Nanoscale Genotyping with Amplified Fragment Length Polymorphism

The methods of the instant invention can be used to perform AFLPs (amplified fragment length polymorphism) in nanoliter volumes. To perform AFLP reactions, genomic DNA is digested with pairs of restriction enzymes. The fragments are either ligated to a linker and amplified to amplify fragments of a certain length, in a certain orientation, as determined by the two restriction enzymes used, or alternatively, amplified by PCR directly using degenerate primers. The amplified fragments are analyzed by capillary electrophoresis. The AFLP analysis method is used to generate a "representation" of a genome, also called an amplicon, with variable fragments as well as constant ones. The amplicon is used to assess the diversity of populations of organisms or to make genome maps in organisms where little sequence and marker information is available.

EXAMPLE 16

Nanoscale Genotyping with Direct Display Analysis

The methods of the present invention can be used to perform direct display analysis in nanoliter volumes. To perform direct display analysis reactions, complementary DNA is digested with pairs of restriction enzymes. The fragments are either ligated to a linker and amplified to amplify fragments of a certain length, in a certain orientation depending on the two restriction enzymes used, or alternatively, amplified by PCR directly using degenerate primers. The amplified fragments are analyzed by capillary electrophoresis. The direct display analysis method is used to generate a "representation" of a transcriptosome, with variable fragments as well as constant ones. Direct display analysis is used to assess the quantitative change in the level of expression between organisms, or differences due to environmental or physiological effects.

EXAMPLE 17

Nanoscale Genotyping by Microsatellite Analysis

The methods of the present invention can be used to perform genotyping by microsatellite analysis in nanoliter volumes. To perform genotyping by microsatellite analysis reactions, genomic DNA is PCR amplified with marker panels such as PE Applied Biosystems Linkage Mapping Sets. For example, 96 human samples are analyzed with respect to panels of 12 genotypes in about 30 minutes using a four-color analysis. Three of the colors are used with four primer sets, while the fourth color provides internal size standards.

PCR set-up and thermocycling is performed as recommended by the manufacturer of the primer panel.

An example of a polymerase chain reaction mixture is as follows:

| Ingredient | Volume |
|---|---|
| 10X Gold Buffer | 1.50 µl |
| MgCl$_2$ (25 mM) | 1.50 µl |
| dNTPs Mix (2.5 mM) | 1.50 µl |
| Primer mix | 1.00 µl |
| AmpliTaq Gold | 0.12 µl |
| Sterile distilled water | 1.38 µl |
|  | 7.00 µl |
| DNA (5 ng/µl) | 8.00 µl |
|  | 15.0 µl per well |

The primer mix contains both forward and reverse primers, each at a final concentration of 5 µM.

An example of a thermal cycler program is as follows:

| Temp | Time | Cycle No. |
|---|---|---|
| 95° C. | 12 mins | 1 cycle |
| 94° C. | 15 sec | |
| 55° C. | 15 sec | |
| 72° C. | 30 sec | 10 cycles |
| 89° C. | 15 sec | |
| 55° C. | 15 sec | |
| 72° C. | 30 sec | 20 cycles |
| 72° C. | 10 mins | 1 cycle |

Pooling

Sealed PCR sample trays are stored at −20° C.

Initially, 1 µl of each PCR product is pooled, after which the final volume is brought up to about 15 to 20 µl with water. Then, samples are dialyzed. Dialysis is done in 0.1×TE for 15 minutes, after which the pooled PCR samples are loaded into the MegaBACE™.

Loading.

Samples are prepared for loading into the MegaBACET™ as follows:

| Ingredient | Volume |
|---|---|
| Desalted PCR pools | 2.00 ul |
| ET400-R Size Standard | 0.25 ul |
| Formamide loading solution | 2.75 ul |
| Total loading volume | 5.00 ul |

EXAMPLE 18

Nanoscale Enzymatic Reactions with Nucleic Acids

The present invention is advantageously applied to performing nanoscale enzymatic reactions with nucleic acids in nanoliter volumes. The nucleic acids are immobilized in a reaction chamber, such as a glass capillary, prepared according to the methods of the instant invention. The capillaries are filled with reaction mixtures that comprise one or more of different enzymes, such as a restriction enzyme.

A typical restriction enzyme digest is performed in a total volume of 20 µL that includes 0.2 to 1.5 µg of substrate DNA and a 2–10 fold excess of restriction enzyme over DNA. Reaction buffer, enzyme, water, and DNA are mixed in a reaction tube and incubated at 37° C. for 1 to 4 hours. According to the instant invention template DNA is bound to the inner surface of a capillary tube. Then, a premix of restriction enzyme (e.g. Hind III) in a 1×KGB buffer (100 mM potassium glutamate, 25 mM Tris-acetate, pH 7.5, 10 mM magnesium sulfate, 50 µg/ml bovine serum albumin, and 1 mM β-mercaptoethanol) is drawn into the capillary by capillary action. The reaction is incubated at 37° C. for an allotted time, after which the contents are dispensed in gel-loading buffer for agarose gel sizing, or into a solution containing 10 mM EDTA.

Other reactions comprising different enzymes are also possible. These enzymes include, but are not limited to methylation enzymes, DNA-dependent DNA polymerase enzymes, terminal transferase enzymes, RNA-dependent DNA polymerase enzymes, DNA-dependent RNA polymerase enzymes, phosphatase enzymes, kinase enzymes, exonuclease enzymes, such as S1, or mung bean nucleases, other nuclease enzymes, ribonuclease enzymes, or DNA or RNA ligase enzymes. For most of these reactions, control over the ratio of nucleic acid to enzyme is crucial to the success of the reaction process.

Use of the present application beneficially reduces the error associated with concentration dependent enzymatic reactions with nucleic acids, as well as reducing the consumption of valuable enzymes. Furthermore, through washing, use of the methods of the present invention is effective for eliminating residual ions, such as ammonium acetate, EDTA, and lithium chloride, and other contaminants, such as polysaccharides that interfere with enzymatic activity.

EXAMPLE 19

Direct Sequencing from a Microarray Spotting Plate

To ensure the integrity of the data generated using microarrays, it is necessary that the identity of the sequence of the spotted DNA be known with high confidence. PCR is often used to generate the DNA to be spotted, and as is well known in the art, Taq and related thermostable polymerases introduces a certain number of erroneous base pairs per thousand as it amplifies the template. If errors have been introduced they must be detected, and the amplified product or data therefrom discarded. Usually, this requires numerous processing steps separate from those associated with spotting the PCR product. However, use of an embodiment of the present invention greatly increases the efficiency of sequence confirmation.

Confirmation of the sequence of a series of microarray spotting samples was achieved, using the methods of the present invention, as follows.

Microarray spotting samples were prepared from PCR products, average of 500 bp, from human genomic DNA template. The products were purified using standard guanidinium hydrochloride glass-filter plate processing and mixed with an equal volume of 10 M sodium thiocyanate. Samples were arrayed in a microtiter plate ("spotting plate") for subsequent spotting onto the microarray slide.

To confirm the PCR product sequence and positional arrangement on the microarray hybridization slide, sequencing reactions were performed by dipping the ends of a 96-capillary cassette into the spotting plate and binding the DNA to the inside surface of the capillary. After a wash step with 80% ethanol, the capillaries were filled with sequencing mix containing buffer, polymerase, dye-labeled dideoxynucleotides, and sequencing primer at 1×concentration. After thermal cycling (30 cycles at 95° C. for 5 s, 55° C. for 5 s, and 60° C. for 60 s), the sequencing reactions were purified by ethanol precipitation and analyzed by MegaBACE™.

In this example, 60 samples yielded confirmatory sequence, with an average read length of 335 bases (450 bp maximum). By directly sequencing from the same preparation and source as was spotted on the array, we resolved ambiguities in position or identity of the PCR product.

EXAMPLE 20

Direct Sequencing of PCR Products Without Preliminary Removal of PCR Nucleotides and Primers The methods of this invention have been used to simplify the purification of PCR products prior to sequencing. Typically, an enzymatic purification of the PCR product using exonuclease I (ExoI) and arctic shrimp alkaline phosphatase (SAP) to remove primer and excess dNTPs is required prior to cycle sequencing. Because template binding is size dependent, however, the unincorporated primers and remaining nucleotides can instead be removed from the template by differential binding of the template to the capillary, followed by removal of nucleotides and primer by washing. This approach obviates enzymatic cleanup of the PCR product and greatly simplifies the overall workflow.

As a demonstration, 96 PCR products of M13 DNA containing a mouse subclone insert were directly sequenced without enzymatic purification after PCR amplification.

The PCR amplification reactions were performed using M13 templates containing a subclone insert (ca. 2000 bp) of mouse genomic DNA. The M13 templates had previously been prepared by polyethylene glycol precipitation and detergent salvation (Thermomax), diluted 200 fold and rearrayed into a 96-well microtiter plate.

A 2 µL aliquot of this solution was transferred to a PCR amplification mix prepared with 2.5 µL 10×GeneAmp buffer, 0.2 µL of 25 mM each dNTPs, 0.5 µL of 10 µM M13 −40FWD (GTT TTC CCA GTC ACG AC (SEQ ID NO:1)), 0.5 µL of 10 µM M13 −40REV primer (GGA TAA CAA TTT CAC ACA GG (SEQ ID NO:4)), 1.5 µL of 25 mM magnesium chloride, 0.5 µL of 5 U/µL AmpliTaq polymerase, and 17.3 µL water. After mixing and sealing the plate, the reactions were thermally cycled at 95° C. for 10 s, 55° C. for 10 s, and 72° C. for 2 minutes for thirty cycles. After PCR amplification, a 5 µL aliquot was removed and mixed with 5 µL of 10 M sodium thiocyanate in a separate 96-well plate.

The capillaries of a 96-capillary cassette were dipped into the chaotrope-PCR product mixture, thus filling the cassette. After a 5 minute incubation at 60° C., the residual chaotrope, unbound buffer components and DNA were removed with an 80% ethanol wash applied by pulling the ethanol through the capillaries under vacuum. After drying the inside surface with a 1 minute flow of air, the capillaries were dipped into a sequencing mixture containing a 1×solution of ET terminator reaction mix and forward sequencing primer, M13 −21FWD (TGT AAA ACG ACG GCC AGT (SEQ ID NO:2)).

Cycle sequencing was performed by sealing the ends of the capillaries in the air-thermal cycle. The reaction was cycled 30 times at 95° C. for 5 s, 55° C. for 5 s, and 60° C. for 60 s. The cycle-sequencing products were dispensed into a microtiter plate containing 40 µL of 80% ethanol using centrifugal force. After a 30 minute centrifugation at 3000× g, the alcohol was decanted, the pelleted DNA resuspended in 5 µL of ddH2O, and the samples were analyzed by MegaBACE™.

For these 96 samples, an average read length of 550 bases was achieved with 83% pass rate and a sum of 44000 bases. This procedure has been repeated for over 5000 samples with demonstration of improvements over full-volume and enzymatically purified reactions.

All patents, patent publications, and other published references mentioned herein are hereby incorporated by reference in their entireties as if each had be en individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:
1. A method of obtaining substantially the same quantity of nucleic acid from a first and a second sample, comprising:
saturably binding nucleic acid from said first sample directly on an inner surface of a first capillary tube by contacting said inner surface with a solution comprising a nucleic acid and a chaotropic agent for a time sufficient for the nucleic acid to become saturably bound to said inner surface; and
saturably binding nucleic acid from said second sample directly on an inner surface of a second capillary tube by contacting said inner surface with a solution comprising a nucleic acid and a chaotropic agent for a time sufficient for the nucleic acid to become saturably bound to said inner surface,
wherein said inner surfaces of said first and second capillary tubes are capable of saturably binding substantially the same quantity of nucleic acid from each of said first and second samples, respectively.
2. The method of claim 1, wherein the quantity of nucleic acid saturably bound to the inner surfaces of said first and second capillary tubes differs by less than about 10%.

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: M13-40 FWD Primer

<400> SEQUENCE: 1
gttttcccag tcacgacg                                             18

<210> SEQ ID NO 2
<211> LENGTH: 18
<212> TYPE: DNA
<213> ORGANISM: Artificial Sequence
<220> FEATURE:
<223> OTHER INFORMATION: M13-21 FWD Primer

<400> SEQUENCE: 2
tgtaaaacga cggccagt                                             18

<210> SEQ ID NO 3
<211> LENGTH: 17
<212> TYPE: DNA
<213> ORGANISM: Artificial Sequence
<220> FEATURE:
<223> OTHER INFORMATION: M13-40 FWD Primer

<400> SEQUENCE: 3
gttttcccag tcacgac                                              17

<210> SEQ ID NO 4
<211> LENGTH: 20
<212> TYPE: DNA
<213> ORGANISM: Artificial Sequence
<220> FEATURE:
<223> OTHER INFORMATION: M13-40 REV Primer

<400> SEQUENCE: 4
ggataacaat ttcacacagg                                           20

3. The method of claim 1, wherein said binding steps are effected substantially contemporaneously.

4. The method of claim 1, wherein said second capillary tube is the same capillary tube as said first capillary tube, and wherein said binding steps are effected iteratively.

5. The method of claim 1 further comprising, prior to said binding steps, the step of size-selecting a nucleic acid to be saturably bound.

6. The method of claim 1 further comprising, after said binding steps, the step of using the nucleic acid of either of said first or second capillary tubes in an enzymatic reaction.

7. The method of claim 1 wherein the saturably bound nucleic acid of either of said first or second capillary tubes is DNA.

8. The method of claim 7 further comprising, after said binding steps, the step of using the DNA of either of said first or second capillary tubes in an enzymatic reaction.

9. The method of claim 8 wherein said enzymatic reaction is a DNA sequencing reaction.

10. The method of claim 1, wherein either of said first or second capillary tubes comprises glass.

11. The method of claim 1, wherein said capillary tubes are present in an array.

12. The method of claim 11, wherein said array comprises at least 8 capillary tubes.

13. The method of claim 11, wherein said array comprises at least 16 capillary tubes.

14. The method of claim 11, wherein said array comprises at least 96 capillary tubes.

15. The method of claim 1 wherein said chaotropic agent is selected from the group consisting of:

urea, sodium perchlorate, potassium perchlorate, sodium bromide, potassium bromide, sodium iodide, potassium iodide, sodium thiocyanate, potassium thiocyanate, guanidine thiocyanate, sodium isothiocyanate, potassium isothiocyanate, guanidine hydrochloride, guanidine isothiocyanate, lithium chloride, sodium trichloroacetate, dimethylsulfoxide, tetra-amine halides, tetraethylamine chloride, and potassium trichloroacetate.

16. The method of claim 1 further comprising the step of removing the solution, wherein said removing step occurs after said contacting step.

17. The method of claim 16 further comprising the step of washing the inner surface of either of said first or second capillary tubes, wherein said washing step occurs after said removing step.

18. The method of claim 17 further comprising the step of drying the inner surface of either of said first or second capillary tubes, wherein said drying step occurs after said washing step.

19. A method of performing an enzymatic reaction in a capillary tube using a normalized quantity of a nucleic acid, comprising:

performing said enzymatic reaction in a capillary tube using a normalized quantity of said nucleic acid, said nucleic acid having been saturably bound from an excess thereof directly on an inner surface of said capillary tube by contacting said inner surface with a solution comprising a nucleic acid and a chaotropic agent for a time sufficient for the nucleic acid to have become saturably bound to said inner surface; and said excess of nucleic acid having been removed therefrom.

20. The method of claim 19 further comprising the step of introducing into said capillary tube an enzymatic reaction mixture after said excess of nucleic acid has been removed therefrom.

* * * * *